(12) United States Patent
Wynne et al.

(10) Patent No.: US 7,771,793 B2
(45) Date of Patent: Aug. 10, 2010

(54) FUNCTIONAL POLYMERS VIA SURFACE MODIFYING AGENTS, AND METHODS FOR POLYMERIC SURFACE MODIFICATION

(75) Inventors: Kenneth Joseph Wynne, Midlothian, VA (US); Biao Duan, Richmond, VA (US); Steven Grunzinger, Tokyo (JP); Umit Makal, Strongsville, OH (US); Pinar Kurt, Richmond, VA (US); James Wynne, Alexandria, VA (US)

(73) Assignees: Virginia Commonwealth University, Richmond, VA (US); The United States of America as represented by the Secretary of the Navy, Washington, DC (US)

( * ) Notice: Subject to any disclaimer, the term of this patent is extended or adjusted under 35 U.S.C. 154(b) by 1256 days.

(21) Appl. No.: 11/290,803

(22) Filed: Dec. 1, 2005

(65) Prior Publication Data

US 2006/0154083 A1 Jul. 13, 2006

Related U.S. Application Data

(63) Continuation-in-part of application No. 10/882,238, filed on Jul. 2, 2004, now Pat. No. 7,396,590.

(60) Provisional application No. 60/485,494, filed on Jul. 9, 2003.

(51) Int. Cl.
*B05D 1/00* (2006.01)

(52) U.S. Cl. ............................ 427/401; 427/445; 528/44
(58) Field of Classification Search .................. 427/401, 427/445; 528/44
See application file for complete search history.

(56) References Cited

U.S. PATENT DOCUMENTS 5,589,563 A 12/1996 Ward et al.

(Continued)

FOREIGN PATENT DOCUMENTS

WO WO 02/057340 7/2002

OTHER PUBLICATIONS

Fujiwara T. et al.; "Synthesis and Characterization of Novel Amphiphilic Telechelic Polyoxetanes";Macromolecules; 36; 2003; pp. 9383-9389 Wynne K. et al.: "Biocital Polymers Via Polymeric Surface Modifing Additives"; Department of Chemical Engineering and Deparment of Microbiology and Immunology, VCU; pp. 1-2.

(Continued)

*Primary Examiner*—Thao T. Tran
(74) *Attorney, Agent, or Firm*—Whitham Curtis Christofferson & cook, PC

(57) ABSTRACT

Polymers, and particularly conventional commodity bulk polymers, are modified to have a surface activity of interest using a surface modifying polymer that includes a moiety that favors migration to the surface of the bulk polymer together with a moiety provides the activity of interest (e.g., biocidal, wettability modifying (hydrophobic or hydrophilic), resistance to radiant energy, providing a functional group for functionalizing the surface, etc.). The surface modifying polymer is combined with the bulk polymer, and, due to the presence of the moiety that favors migration, concentrates primarily on the surface of the bulk polymer such that the moiety that provides the activity of interest is located primarily on the surface of the bulk polymeric article which is produced. Advantageously, only a minimal amount (such as, e.g., about 2 weight %) of polymeric surface modifier is needed. Being able to achieve desired properties (such as biocidal activity, wettability modification, etc.) without needing much polymeric surface modifier is highly advantageous.

8 Claims, 25 Drawing Sheets

U.S. PATENT DOCUMENTS

| | | |
|---|---|---|
| 5,637,772 A | 6/1997 | Malik et al. |
| 5,807,977 A | 9/1998 | Malik et al. |
| 6,037,483 A | 3/2000 | Malik et al. |
| 6,127,507 A | 10/2000 | Santerre |
| 6,469,177 B1 | 10/2002 | Worley et al. |
| 6,479,623 B1 | 11/2002 | Malik et al. |
| 2005/0084683 A1 | 4/2005 | Wynne |
| 2005/0282997 A1 | 12/2005 | Ward et al. |

OTHER PUBLICATIONS

Wynne K et al.: "Surface Properties and Morphologies of Polyurethanes via Amphiphilic Polyoxetane Telechelics"; Department of Engineering, VCU; pp. 1-2.

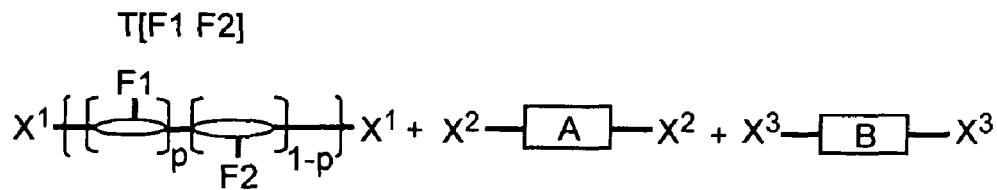
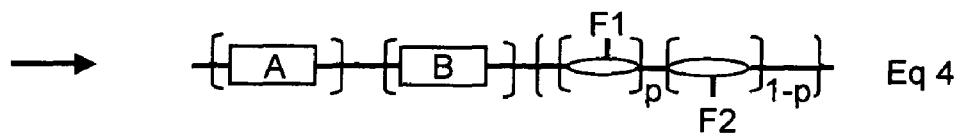 Eq 4
ABT[F1 F2] PSM containing soft block T[F1 F2]
*Figure 5C*
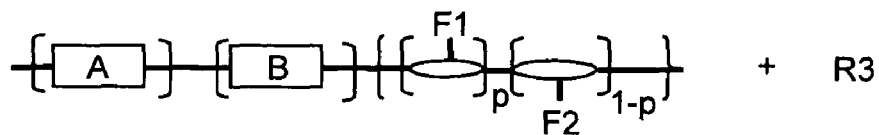 + R3
Eq 5
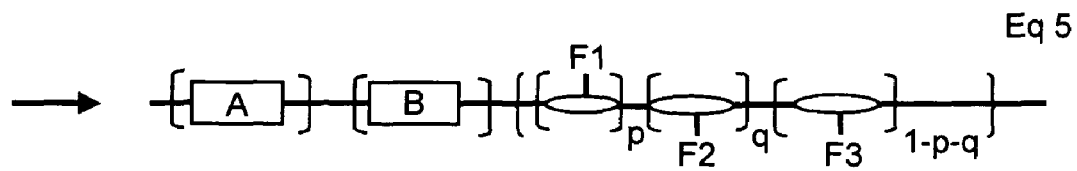
ABT[F1 F2 F3] PSM containing soft block T[F1 F2 F3]
*Figure 5D*

ABT[F1 F2] PSM containing both soft block T[F1 F2] mole fraction $n_1$, and soft block S with mole fraction $n_2$.  Eq 6

100% films

| | Contact angle (°) | |
|---|---|---|
| | Adv. | Rec. |
| PTMO/MDI/BD | 91 | 48 |
| (ME2Ox homo)/MDI/BD | 91 | 55 |
| (ME2Ox-ran-3FOx)/MDI/BD | 99 | 52 |
| (ME2Ox-ran-5FOx)/MDI/BD | 100 | 50 |
| (ME3Ox homo)/MDI/BD | 93 | 32 |
| (ME3Ox-ran-3FOx)/MDI/BD | 104 | 39 |
| (ME3Ox-block-3FOx)/MDI/BD | 106 | 56 |

2% SMA Soft segment — XPS

| | 100% Bulk Calculated F | 2% SMA Observed F |
|---|---|---|
| ME3Ox-ran-3FOx | 10.3 | 13.8 |
| ME3Ox-block-3FOx | 12.0 | 21.1 |
| ME7Ox-ran-3FOx | 5.8 | 14.6 |
| ME7Ox-block-3FOx | 8.6 | 21.2 |

Figure 10

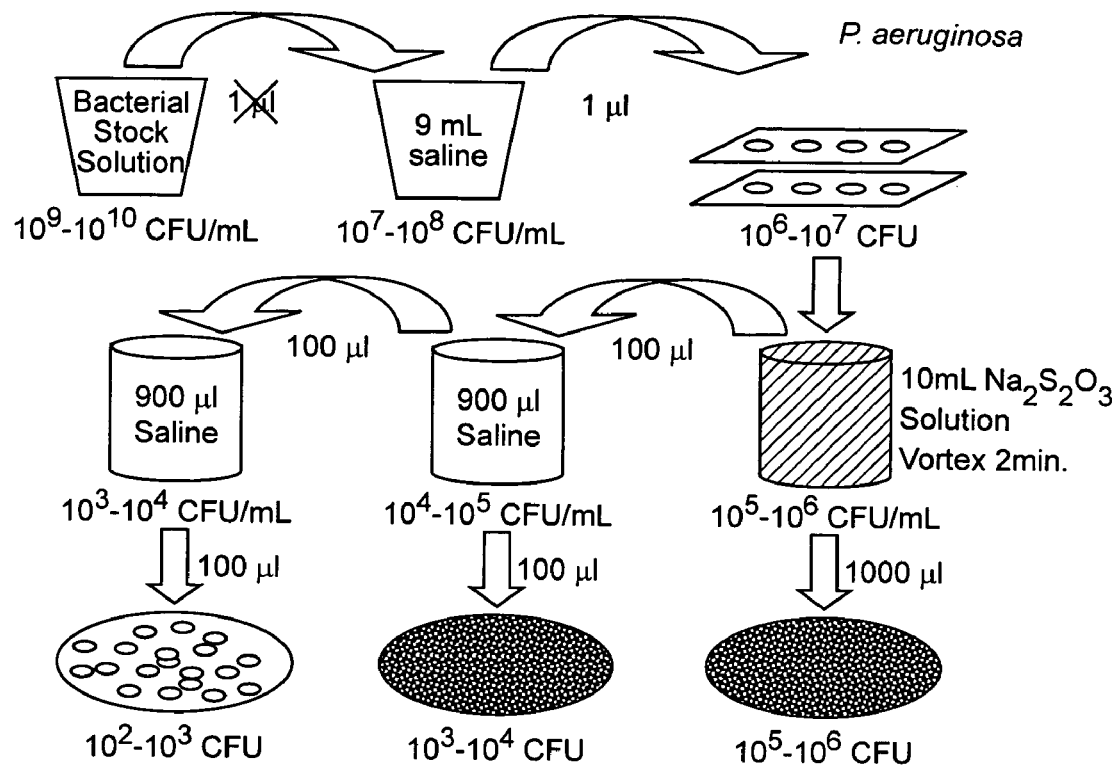
Figure 13
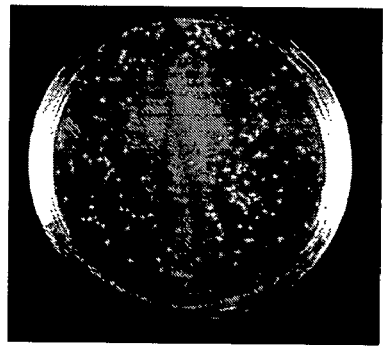
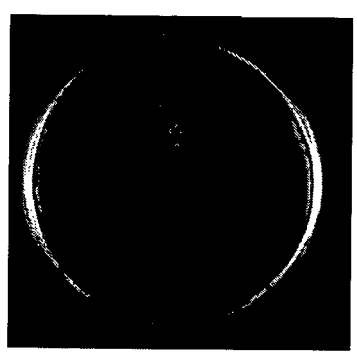
PU Control
> 400 cfu's
98% PU, 2% Biocidal SMA
0 cfu's
Result: Modified AATCC-100 test
• Coating: 98% PU, 2% Biocidal SMA
• Killed all bacteria present (30 min)
• Minimum of 99.9% or 3.6 log reduction
Figure 14

Copolymerization of ME2Ox and FOx monomers via BF$_3$-OEt$_2$ catalyst system at 0 C in methyene chloride

| Sample Name | Monomer feed ratio | | | [Monomer]/co-catalyst[a] | Polymers | | | | |
|---|---|---|---|---|---|---|---|---|---|
| | ME2Ox | 5FOx | 7FOx | | ME2Ox/FOx | $D_P$[b] | Equiv. MW[b] | $M_n$[c] (/10)$^3$ | $M_w/M_n$[c] |
| M-1 | 1 | - | - | 5.5 | - | 12.4 | 2540 | 3.4 | 2.7 |
| M-2 | 1 | - | - | 11 | - | 16.9 | 3450 | 3.6 | 3.2 |
| M-3 | 1 | - | - | 22 | - | 18.6 | 3810 | 3.0 | 2.1 |
| M-4 | 1 | - | - | 33 | - | 18.2 | 3710 | 3.3 | 2.2 |
| M5F-1 | 0.5 | 0.5 | - | 5.5 | 0.53/0.47 | 16.8 | 3680 | 4.0 | 2.6 |
| M5F-2 | 0.5 | 0.5 | - | 11 | 0.54/0.46 | 17.9 | 3910 | 4.8 | 2.8 |
| M5F-3 | 0.5 | 0.5 | - | 22 | 0.53/0.47 | 20.8 | 4570 | 4.7 | 1.9 |
| M5F-4 | 0.5 | 0.5 | - | 33 | 0.52/0.48 | 20.6 | 4520 | 4.8 | 1.9 |
| F-1 | - | 1 | - | 5.5 | - | 20.1 | 4720 | 8.7 | 2.4 |
| F-2 | - | 1 | - | 11 | - | 27.3 | 6390 | 11.6 | 2.1 |
| F-3 | - | 1 | - | 22 | - | 31.9 | 7470 | 11.8 | 1.9 |
| F-4 | - | 1 | - | 33 | - | 36.8 | 8620 | 12.9 | 2.0 |
| M7F-1 | 0.5 | - | 0.5 | 22 | 0.55/0.45 | 18.6 | 4550 | 5.3 | 2.2 |
| M7F-2 | 0.67 | - | 0.33 | 22 | 0.66/0.34 | 14.9 | 3440 | 4.5 | 1.9 |

[a] Monomer to co-catalyst (1,4-butanediol) molar ratio, [BF$_3$-OEt$_2$]/[1,4-butanediol] = 2.2 (constant)
[b] Determined by $^1$H-NMR end group analysis
[c] Determined by GPC

| Telechelic polymers | Endgp (10⁻³) | GPC molecular weight(10⁻³) | | | cyc% | DSC Tg | DSC Tc/Tm | MDSC Tg¹ |
|---|---|---|---|---|---|---|---|---|
| | | Mn | Mw | (Pd) | | | | |
| PTMO | 2.2 | 3.7 | 6.8 | 1.9 | 20 | ? | ? | -78.1 |
| 3FOx homo | 7.1 | 13.9 | 21.6 | 1.5 | | -47.6 | - | -47.4 |
| 5FOx homo | 7.5 | - | - | - | | -45.9 | - | - |
| 7FOx homo | - | - | - | - | | -54.6 | - | - |
| ME2Ox homo | 3.8 | 3.0 | 6.3 | 2.1 | | -68.0 | - | - |
| ME2Ox/3FOx (1/1) | 3.8 | 2.3 | 7.5 | 3.2 | | -57.7 | - | - |
| ME2Ox/5FOx (1/1) | 4.6 | 4.7 | 8.9 | 1.9 | | -58.1 | - | - |
| ME2Ox/7FOx (1/1) | 4.5 | 7.5 | 12.6 | 1.7 | | -56.9 | - | - |
| ME2Ox/7FOx (2/1) | 3.4 | 6.1 | 9.6 | 1.6 | | -58.5 | - | - |
| ME3Ox homo | 3.0 | 0.7 | 3.2 | 4.6 | | -75.8 | - | -74.2 |
| ME3Ox/3FOx (1/1) | 3.1 | 1.6 | 4.3 | 2.6 | | -63.9 | - | -61.8 |
| ME3Ox-block-3FOx(2/3) | 4.2 | 1.6 | 4.1 | 2.6 | 12 | -61.8 | - | -59.7 |
| ME3Ox-block-3FOx(2/1) | 1.9 | 0.8 | 3.5 | 4.5 | 9 | -70.7 | - | -69.0 |
| ME7Ox homo | 3.2 | 1.0 | 2.7 | 2.7 | | -71.8 | -52/-16 | - |
| ME7Ox/3FOx (1/1) | 5.8 | 2.4 | 5.1 | 2.1 | | -66.9 | -30/-16 | - |
| ME7Ox-block-3FOx(2/3) | 5.2 | 3.2 | 5.2 | 1.6 | | -64.8 | -28/-13 | - |
| ME7Ox-block-3FOx(2/1) | 3.5 | 1.9 | 4.5 | 2.4 | | -70.5 | -48/-16 | - |
| ME2Ox homo + 5FOx homo | - | - | - | - | | - | - | - |
| ME3Ox homo + 3FOx homo | - | - | - | - | | -64/-45 | - | -69.8/-57.9 |

| Polyurethanes | sswt% | molecular weight(10⁻³) | | | DSC Tg¹ | DSC Tg² | MDSC Tg¹ | MDSC Tg² |
|---|---|---|---|---|---|---|---|---|
| | | Mn | Mw | Pd | | | | |
| PTMO/MDI/BD | 64 | 37.5 | 142.9 | 3.8 | ? | ? | -70.3 | 56.6 |
| (ME2Ox homo)/MDI/DB | 50 | - | - | - | (?) | 49.7 | - | - |
| (ME2Ox/3FOx (1/1)/MDI/DB | 74 | - | - | - | 38.8 | (?) | - | - |
| (ME2Ox/5FOx (1/1)/MDI/DB | 74 | - | - | - | -41.8 | (?) | - | - |
| (ME2Ox/5FOx (1/1)/MDI/DB | 45 | - | - | - | - | - | - | - |
| (ME3Ox homo)/MDI/DB | 63 | 7.8 | 14.1 | 1.8 | -43.8 | (?) | -36.8 | 129.9? |
| (ME3Ox/3FOx (1/1)/MDI/DB | 73 | 9.1 | 24.3 | 2.7 | -41.2 | (?) | -36.8 | ? |
| (ME3Ox-b-3FOx(2/3)/MDI/DB | 68 | 7.4 | 15.2 | 2.1 | -41.9 | (?) | -38.4 | 65.1 |
| (ME7Ox homo)/MDI/DB | 69 | 6.5 | 10.0 | 1.6 | -55.9 | (?) | - | - |
| (ME7Ox/3FOx (1/1)/MDI/DB | 58 | 6.0 | 10.1 | 1.7 | -46.4 | - | - | - |
| (ME7Ox-b-3FOx(2/3)/MDI/DB | 66 | 6.3 | 12.3 | 2.0 | -44.4 | - | - | - |
| (3FOx homo)/MDI/DB | 71 | 13.4 | 43.1 | 3.2 | - | - | -39.9 | 59.9 |
| (Mix.ME3Ox + 3FOx)(1/1)/MDI/BD | 70 | 7.9 | 16.0 | 2.0 | - | - | -59.3/-42.5 | ? |

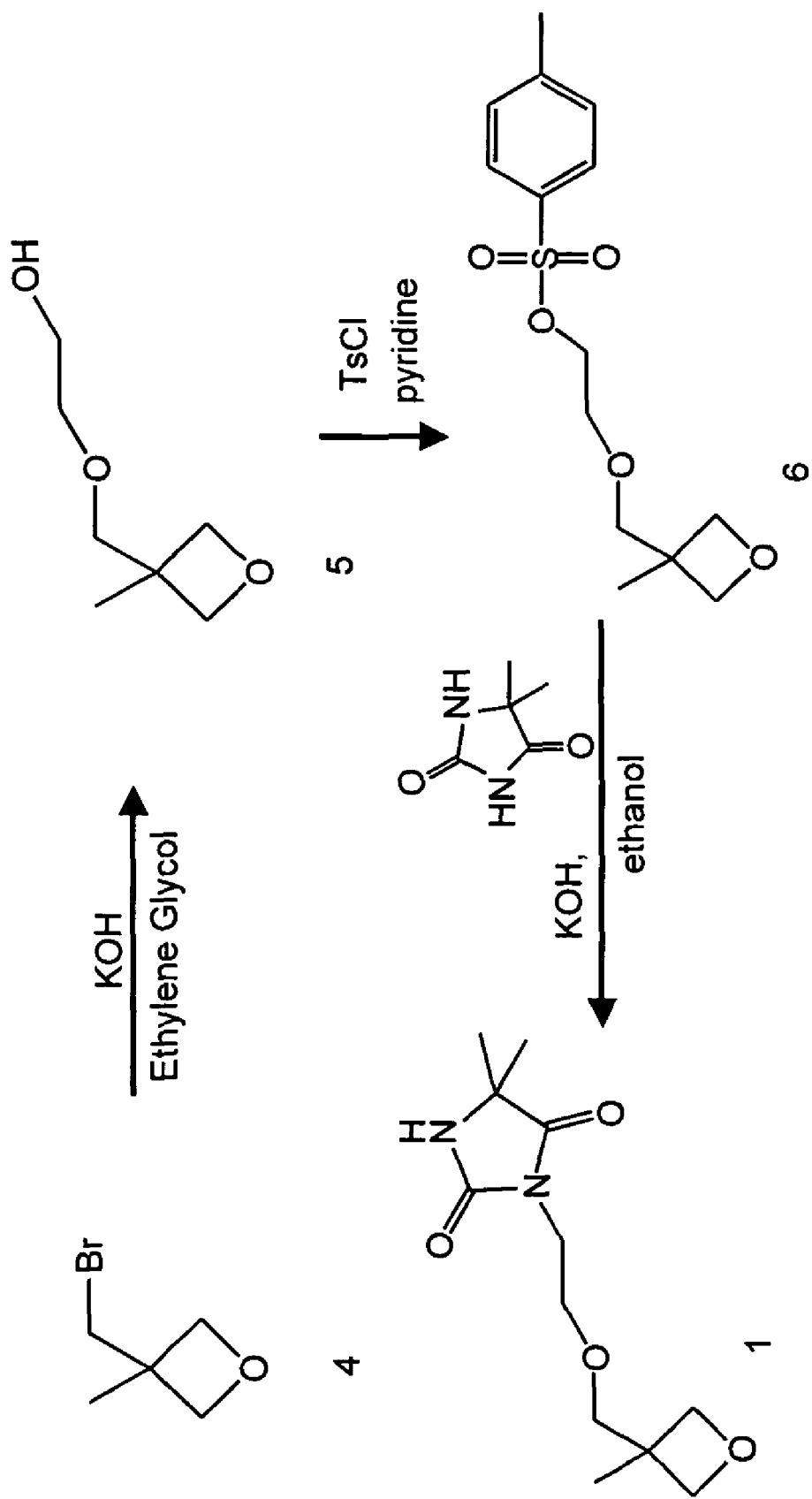
Figure 17. Synthesis of the new monomer Hy4Ox.

Preparation of ME2Ox:hexylammonium butoxymethyl telechelic 13 from precursor bromobutoxy-ME2Ox telechelic 12

Preparation of ME2Ox:hexylammonium butoxymethyl telechelic 15 from precursor bromobutoxy-ME2Ox telechelic 14

Preparation of ME2Ox:dodecyl ammonium butoxymethyl telechelic 16 from precursor bromobutoxy-ME2Ox telechelic 14

| Telechelic | Mn (10³ g/mole) | Tg (°C) |
|---|---|---|
| P(N611E1Ox) | 2.4 | -24 |
| 10 | 13 | N/A |
| 11 | 13.8 | -27 |
| 12 | 8.4 | -48 |
| 13 | 8.7 | -40 |
| 14 | 8.0 | -57 |
| 15 | 8.7 | -17 |
| 16 | 9.2 | N/A |

Calculation of number average molecular weight by ¹HNMR and glass transition temperatures of telechelics obtained by modulated DSC Characterization data for HMDI-BD(wt%)/P(Hy4Ox:MOx) polyurethanes.

| | $M_w{}^a$ (g/mol) | $M_w/M_n$ | Hard Block[b] (wt%) | $T_g$ (°C)[c] Onset | Inflection | End | Phase[d] Mixing (wt%) |
|---|---|---|---|---|---|---|---|
| HMDI-BD(52.5)/P MOx (PU-A) | $1.1 \times 10^5$ | 2.1 | 52.5 | −38.1 | −33.3 | −29.3 | 18.1 |
| HMDI-BD(54.0)/P(Hy4MOx-8:92) (PU-B) | $5.0 \times 10^4$ | 1.3 | 54.0 | −9.5 | 24.6 | 51.2 | 59.3 |
| HMDI-BD(56.7)/P(Hy4MOx-16:84) (PU-C) | $2.2 \times 10^4$ | 2.5 | 56.7 | −15.3 | 13.0 | 33.8 | 53.8 |
| HMDI-BD(51.1)/P(Hy4MOx-39:61) (PU-D) | $7.9 \times 10^3$ | 2.9 | 51.1 | 12.9 | 26.5 | 41.4 | 40.7 |
| HMDI-BD(49.7)/P(Hy4Ox) (PU-E) | $6.9 \times 10^3$ | 2.3 | 49.7 | 64.5 | 72.9 | 78.1 | 82.9 |

(a) Molecular weight and polydispersity (GPC)
(b) Estimated error for hard-block content is ± 2.4wt%
(c) $T_g$ (DSC)
(d) Estimated errors for phase mixing ± 5.0 (HMDI-BD(52.5)/P(MOx) and HMDI-BD(49.7)/P(Hy4Ox)) or ± 20

*Figure 22*

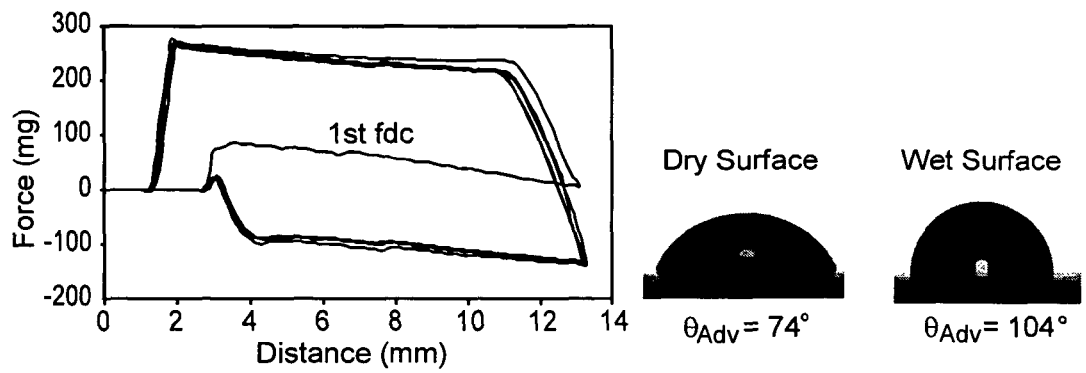
*Figure 24A*
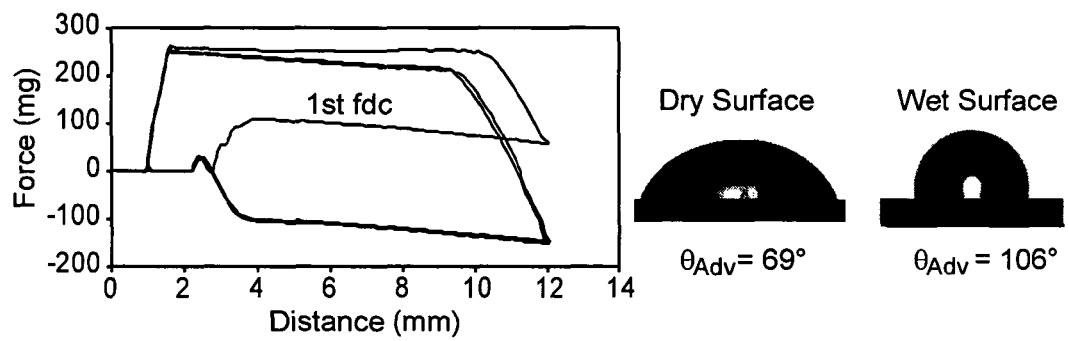
*Figure 24B*
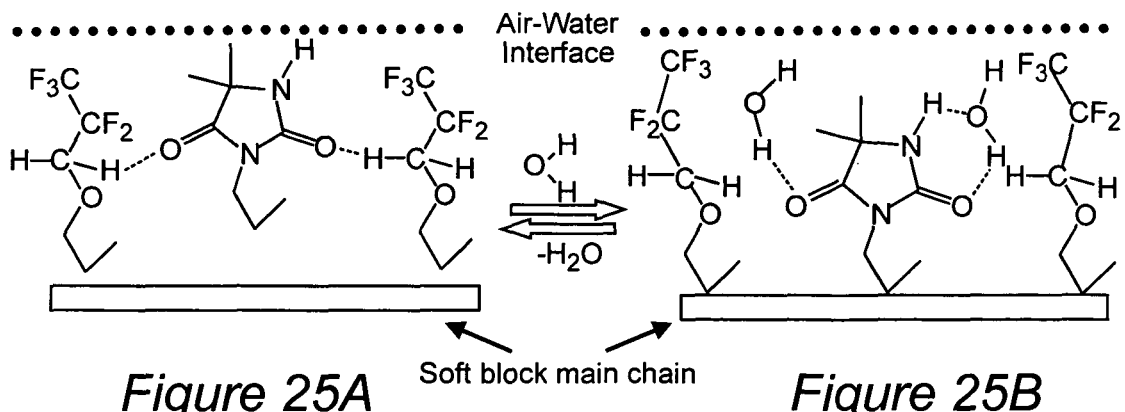
*Figure 25A*      Soft block main chain      *Figure 25B*

Force vs distance curves and dynamic contact angles for bulk IPDI-BD-PTMO coating doped with 10wt % PU-2: Co-Soft Block : [PEO]1-[3FOx:BrOx-1:2]1 with 5,5-dimethylhydantoin (~55% substitution of C-Br by Hy.); Hard Block : IPDI - BD (40%), solvent cast film from THF dried @60C, 4 Torr overnight.

Structure of H₁₂MDI(30%)-BD-P(N611E1Ox)

Structure of H₁₂MDI(40%)-BD-11(0.25)

Structure of HDI(20%)-BD-13(0.125)

Structure of $H_{12}$MDI(40%)-BD-15(0.25)

Structure of MDI(30%)-BD-15(0.25)

Structure of MDI(30%)-BD-16(0.25)

US 7,771,793 B2

FUNCTIONAL POLYMERS VIA SURFACE MODIFYING AGENTS, AND METHODS FOR POLYMERIC SURFACE MODIFICATION

CROSS-REFERENCE TO RELATED APPLICATIONS

This patent application is continuation-in-part of 10/882,238 filed Jul. 2, 2004 now U.S. Pat. No. 7,396,590, which claims benefit of U.S. Provisional Application 60/485,494 filed Jul. 9, 2003, and the complete contents of those applications are herein incorporated by reference.

GOVERNMENT INTERESTS

This invention was made using grants from the U.S. Government, particularly NSF (523279), DARPA (528979), and the government may have certain rights under the patent.

BACKGROUND OF THE INVENTION

1. Field of the Invention

The present invention generally relates to a method for modifying the surface of conventional commodity polymers, including without limitation polyurethanes, polyesters, polyethers, polyamides, polyimides, etc.

2. Background

Surface modification of a polymeric article is performed or attempted for a number of different reasons. For example, it may be desirable to have a bulk polymer that has a surface that is modified to better accept a paint or dye, or to have a surface that imparts a property such as resistance to chemical or radiant energy damage.

A number of different methods have been developed for modifying the surfaces of a polymer. Many of these methods involve post processing of the article. For example, the polymeric article may be exposed to a plasma, or a plasma processing step followed by grafting of compounds to the surface of the polymer. Also, the polymeric article might be subjected to a chemical or radiant energy exposure to alter the surface. It is known to combine a fluorinated polymer with a conventional polymer to get the surface-concentrated fluoropolymer. (Ji, Q.; Kang, H.; Wang, J.; Wang, S.; Glass, T. E.; McGrath, J. E., Surface characterization of fluorinated oxetane polyol modified polyurethane block copolymers, Polymer Preprints, 2000, 41, 346-347, Kim, Y. S.; Lee, J. S.; Ji, Q.; McGrath, J. E., Surface properties of fluorinated oxetane polyol modified polyurethane block copolymers, *Polymer*, 2002, 43, 7161-7170.) It is known that combining a fluorinated group with a UV absorbing chromophore surface-concentrates the chromophore. (Vogl, O.; Jaycox, G. D.; Hatada, K., Macromolecular design and architecture, Journal of Macromolecular Science-Chemistry, 1990, 27, 1781-1854.) It is known that combining a perfluorohexyl group with a fullerene surface-concentrates the fullerene at a styrene air interface. (Chen, W.; McCarthy, T. J., Adsorption/migration of a perfluorohexylated fullerene from the bulk to the polymer/air interface, Macromolecules, 1999, 32, 2342-2347.)

Certain work has occurred thus far on polymeric surface modifiers (PSM). Chen, W.; McCarthy, T. J., *Macromolecules* 1999, 32, 2342-2347; Ho, T.; Wynne, K; *J. Polym. Adv. Tech.* 1994, 6, 25-31; Ward, R. S.; White, K. A.; Hu, C. B., in *Biomedical Engineering*; Planck, H., Egbers, G., Syre, I., Eds.; Elsevier Science Publishers: Amsterdam, 1984.

Surfaces have been made hydrophobic using PDMS PSMs. Ho, Wynne, supra; Ratner, B. D., Yoon, S. C., Kaul, A., Rahman, R., in *Polyurethanes in biomedical engineering II*; Planck, H., Syre, I. Dauner, M., Egbers, G., Eds., Elsevier, New York, 1986; Vol. 3, pp. 213-229; Tezuka, Y., Fukushima, A., Matsui, S., Imai, K., *Journal of Colloid and Interface Science*, 1986, 114, 16-25. Surfaces have been made hydrophobic and oleophobic with fluorinated PSMs. Malik, A. A., Carlson, R. P., Aerojet General Corporation: US, 1997, p. 20; Thomas, R. R., Anton, D. R.; Graham, W. F., Darmon, M. J., Sauer, B. B., Stika, K. M., Swartzfager, D. G., *Macromolecules* 1997, 30, 2883-2890; Thomas, R. R., Ji, Q., Kim, Y. S., Lee, J. S., McGrath, J. E., *Polyurethane* 2000 *Polymer Division Abstracts* 2000; Thomas, R. R., Anton, D. R., Graham, W. F., Darmon, M. J., Stika, K. M., *Macromolecules* 1998, 31, 4595-4604. In this work, the modifying soft block usually consists of a single repeat as typified by polydimethylsiloxane PSMs where the repeat unit is [—(CH$_3$)$_2$SiO—] (see Ho, Wynne, supra) or surface modifiers derived from semifluorinated oxetane monomers that yield telechelics having a 3,3' substituted 1,3-propylene oxide repeat, for example, [—CH$_2$C(CH$_3$)(CH$_2$OCH$_2$CF$_3$)CH$_2$O—] (see Kim, Y. S., Lee, J. S., Ji, Q., McGrath, J. E., *Polymer* 2002, 43, 7161-7170).

There has been work regarding oxetane monomers. Synthesis of fluorinated oxetanes is disclosed in U.S. Pat. No. 6,037,483 to Malik, et al. ("Polymers and prepolymers from mono-substituted fluorinated oxetane monomers") and U.S. Pat. No. 5,807,977 to Malik et al. ("Solvent-free process for the preparation of mono-substituted fluorinated oxetane monomers"). There has been work regarding synthesis of polyurethanes containing fluorinated oxetanes (having a 3,3' substituted 1,3-propylene oxide repeat). See Kim et al. (2002), supra.

Also mentioned as background are the following:

U.S. Pat. No. 6,479,623 to Malik, Archibald, Carlson, Wynne and Kresge, issued Nov. 12, 2002, titled "Amorphous Polyether Glycols based on bis-substituted oxetane copolymers."

PCT Int. Application No. WO 2001-US44556 20011128, by Patel, Mohajer, Twomey, Mares and Nelson, Honeywell Int. Inc., "Polymeric additives and polymeric articles comprising the additive."

PCT Int. Application No. WO1994-US5999, by Sastri, Mohajer, Young, Boyle, Allied Signal Inc., "Polydiorganosiloxane-modified polymer and its preparation."

SUMMARY OF THE INVENTION

It is therefore an object of the invention to provide polymeric articles or coatings, and methods of making polymeric articles or coatings, where the polymeric article has a surface phase having an activity of interest.

According to the invention, there is provided a methodology for preparing polymer articles or coatings which have a surface phase with an activity of interest. It is understood that a telechelic is an oligomeric or polymeric material with reactive groups usually at the chain ends and may also be called a macromonomer. In the methodology, a surface active telechelic or polymer is prepared which includes at least one or more functional segmers which provide an activity of interest (e.g., biocide, bioactive, UV protective, hydrophobic, hydrophilic, conducting, etc.). When combined with bulk polymer, the surface active segmers act as chaperones to bring the functional segmers to the surface of the polymeric article during processing (e.g., creation of a coating, extruding, etc.). In one embodiment, the surface modifying additive consists of one or more telechelics that contain fluorinated surface-active segmers and functional segmers or one or more polyurethanes comprised of conventional hard block forming units (diisocyanates and diols and/or diamines) and soft blocks that contain fluorinated surface-active segmers and functional segmers. The surface-active segmers bring the functional segmers to the surface and together these segmers constitute the functional surface-active soft block of the surface modifiers (SMs). To demonstrate a specific embodiment in a broad range of possible functional SMs, biocidal SMs have been prepared by preparing polyurethane SMs comprised of isophorone diisocyanante/butane diol hard blocks and soft blocks comprised of fluorinated segmers (surface active) combined with biocidal moieties (function) in soft blocks. After activation, these SMs effectively kill pathogen challenges on contact demonstrating the efficacy of the SM concept. Additional examples demonstrate that SMs confer unusual wetting behavior on the substrate polymer. Such tailored change may find use in biomaterials, filters, cosmetics, and other areas where surface properties such as feel and capability to attract moisture are important. It is understood in the context of this patent, that the terms telechelic and macromonomer are used interchangeably. Furthermore, it is understood that when a statement is made such as "telechelic in the polyurethane" that the terminal reactive groups present on the telechelic are no longer present but changed to appropriate functionality by virtue of incorporation (e.g, a urethane group if reaction occurs between an alcohol group on the telechelic with an isocyanate on the hard block).

Advantageously, a desired chaperoning function may be achieved using a minimal amount of PSM. Also advantageously, it has now been shown that surface activity can be achieved in the case of a co-segment M Ox (where M=a methoxy terminated ethylene oxide side chain) without needing a fluorinated segment. Being able to use very little of a surface active segmer while providing the desired surface activity is advantageous, because the co-segment lowers the glass transition temperature of the soft block and may thereby make the functional segment more effective.

In a preferred embodiment, the invention provides a method of producing a polymeric article or coating with a surface active property, comprising the steps of: forming a surface active polymer or telechelic having at least a segmer which enables an activity of interest (such as, e.g., a segmer which comprises an alkylammonium moiety; a segmer which is present on a soft block (such as, e.g., a soft block containing no fluorinated segment; etc.); and combining said surface active polymer with said bulk polymer to produce a polymeric article having the surface active polymer concentrated primarily on the surface of said bulk polymer (such as, e.g., a polymeric article or coating having a combination function selected from the group consisting of biocidal activity and contraphilic activity). Preferably, in this inventive production method, a polymeric article or coating is produced with adding a minimal amount of surface modifier of not more than 5 weight %, with about 2 weight % being a preferred example of a minimal amount of surface modifier.

The invention in another preferred embodiment provides a polymeric article or coating, comprising: a bulk polymer phase (such as, e.g., a bulk phase including polyurethane); and a surface active phase (such as, e.g., a surface active phase including polyurethane; a surface active phase that comprises less than 10 percent by weight of said polymeric article or coating; a surface active phase that comprises about 0.1-3 percent by weight of said polymeric article or coating; etc.) present at a surface, said surface active phase comprising a surface active polymer or soft block having at least a segmer which enables an activity of interest (such as, e.g., biocidal activity; altering surface wettability) of said bulk polymer; providing an indicator (such as, e.g., a color change indicator, fluorescence indicator, phosphorescence indicator, chemiluminescence indicator, etc.); a modifiable leaving group; conductivity; etc.), with preferred examples of such inventive polymeric articles or coatings being those in which said surface active polymer and said bulk polymer are both polyurethanes; and, polymeric articles or coatings lacking a fluorinated segment. Preferably, only a minimal amount (such as, e.g., preferably less than about 5 weight %, such as about 2 weight %) of PSM is included in these inventive polymeric articles or coatings. In the inventive polymeric articles and coatings, there may be an identity of monomeric units in said bulk polymer phase and said surface active phase. In a preferred example, both the bulk polymer phase and the surface active phase include polyurethane in an inventive coating or polymeric article. Examples of the segmer which enables an activity of interest are, e.g., a segmer that includes a hydantoin or hydantoin like moiety; a segmer that includes a dye; a segmer that includes a moiety that converts to siliceous functionalization in the presence of moisture (such as, e.g., a moiety —OSi(OR)$_3$ where R is a hydrolysable group (such as, e.g., methoxy, ethoxy, propoxy, trifluoroethoxy, acetoxy, etc.); a segmer that includes a biocidal moiety; a segmer that includes a bioactive moiety; a segmer that includes an alkylammonium moiety; etc.

In another preferred embodiment the invention provides a contraphilic polymeric material which is hydrophilic when dry and hydrophobic when wet, wherein the contraphilic polymeric material has a delta-theta of at least about 10 degrees (preferably, a delta-theta of at least about 20 degrees, more preferably a delta-theta of at least about 25 degrees, even more preferably a delta-theta of at least about 30 degrees), wherein delta-theta means difference between initial contact angle when dry (hydrophilic) and a contact angle when wet (hydrophobic).

In another preferred embodiment, the invention provides a method of making a contraphilic polymeric material, comprising: processing a bulk polyurethane with a minimal amount (such as, e.g., about 2 weight %, and preferably not more than about 5 weight %) of contraphilic polymeric surface modifier (PSM).

The invention provides, in another preferred embodiment, a polymer material or coating comprising: an isophorone diisocyanate/butane diol hard block; and soft blocks comprised of at least biocidal moieties.

Also, the invention in a further preferred embodiment provides an oligomeric or polymeric detergent or surfactant, comprising at least two of: oleophilic groups, hydrophilic groups and fluorous groups.

The invention in another preferred embodiment also provides novel monomers (such as, e.g., a monomer Hy4Ox, 5,5-dimethyl-3-(2-((3-methyloxetan-3-yl)methoxy)ethyl)-imidazolidine-2,4-dione, and a monomer MOx, 3-methoxymethyl-3-methyloxetane) and novel telechelics, such as, e.g., a telechelic copolymerized from Hy4Ox and MOx. The telechelics of this invention may be used, e.g., to make novel antimicrobial PSMs.

The invention in another preferred embodiment also provides polyurethanes containing Hy4Ox-MOx telechelics.

In other preferred embodiments, the invention provides: a polyurethane surface modifier comprising (a) a segmer comprising a C12 alkyl ammonium and (b) a segmer comprising Me2Ox; and, a polyurethane surface modifier comprising (a) a segmer comprising a C12 alkylammonium and (b) a segmer comprising 3FOx.

BRIEF DESCRIPTION OF THE DRAWINGS

The foregoing and other objects, aspects and advantages will be better understood from the following detailed description of a preferred embodiment of the invention with reference to the drawings, in which:

FIG. 5C is a schematic flow diagram showing generation of polyurethane PSMs, and new PU PSMs may be prepared by using the method of FIG. 5C.

FIG. 5D is a schematic flow diagram showing incorporation of a desired functionality into the soft block of a PSM.

FIG. 10 shows AFM images in combination with contact angle and XPS data which demonstrate the phase separated nanoscale morphology of MDI/BD/(ME3Ox-block-3F)(1:1), PU-2 shown in FIG. 9f is conferred at a 2% loading level to conventional MDI/BD(36)/PTMO polyurethane.

FIG. 13 shows a schematic representation of the AATCC-100 test discussed in Example 5 for demonstrating biocidal activity.

FIG. 14 shows bacterial challenge (E. coli) results obtained using the SMA modified bulk polymers of the present invention.

FIG. 16 is Table 5, Copolymerization of ME2Ox and FOx monomers via BF$_3$—OEt$_2$ catalyst system at 0° C. in methylene chloride. This same Table 5 that was included in the parent application, without a figure number.

FIG. 16A is Table 7, which is discussed herein regarding Example 3 and synthesis of telechelics. This same table was included in the parent application, without a figure number.

FIG. 17 is a reaction scheme showing synthesis of the new monomer Hy4Ox.

FIG. 22 is a table of characterization data for HMDI-BD (wt %)/P(Hy4Ox:MOx) polyurethanes.

FIG. 24 shows DCA force versus distance curves and goniometer drop profiles for PU-2 (A); and PU-6 (B).

FIG. 25 shows a proposed reaction mechanism for contraphilic wetting.

FIG. 27 is discussed in Example 9 herein.

FIG. 28 is discussed in Example 10 herein.

DETAILED DESCRIPTION OF A PREFERRED EMBODIMENT OF THE INVENTION

Figure 1:
FIG. 1 is a schematic generalized representation of a surface active modifier and bulk substrate.

The general concept of a surface modification contemplated by the present invention is shown in FIG. 1. The objective is to modify the surface of a coating or molded object, referred to generically as a polymeric article 10 to include a surface domain 12 which has a property of interest without affecting the bulk properties in the bulk domain 14.

The invention generally relates to polymeric additives that act to modify the surface properties of conventional commodity polymers. This is achieved by synthesis of polymeric surface modifiers (SMs or PSMs), sometimes referred to as surface modifier additives (SMAs) with a structure that favors migration to the surface of a bulk polymer. In particular, the surface-philic character of the SMs depends on the presence of a functional block, which is preferably a "soft block" or flexible chain segment that contains a surface-active segmer and a functional segmer. The approach leverages the general tendency of soft blocks to surface segregate, the presence of surface active groups such as fluorinated groups (inclusive of fully fluorinated or semifluorinated groups [e.g., —$(CH_2)$n$(CF_2)$mF, —$(CH_2)$n$(CF_2)$mH where n is typically 1-10 and m is typically 1-12] in the soft segment, and the synergistic combination of surface-philic soft blocks with a multiplicity of surface active groups. Fluorinated groups have been mentioned, but it should be appreciated that fluorinated groups are not required in all inventive embodiments.

Figure 2:
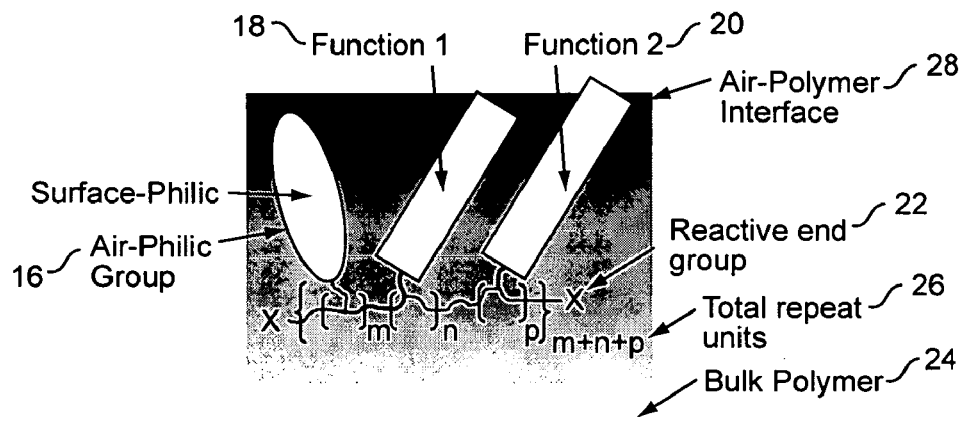
FIG. 2 is a schematic representation of a surface active functional soft block.
Figure 4:
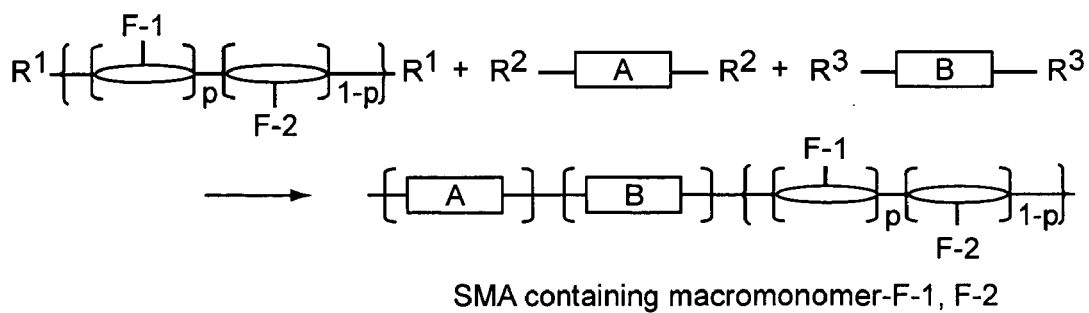
FIG. 4 is a schematic flow diagram representation showing the incorporation of the macronomoner of FIG. 3 into a polymer to form a surface modifying additive (SMA) polymer which contains the macromonomer.

A general structure for such a soft block is shown in FIG. 2. The exact embodiment will depend on the commodity or bulk polymer chosen for modification. In particular, an air philic group 16, such as a semifluorinated group, is combined in the soft block with one or more functional moieties 18 and 20 shown for exemplary purposes as function 1 and function 2, respectively. The telechelic may have reactive end groups 22 which may polymerize with monomers for the purpose of incorporation into an SMA as shown in FIG. 4. The telechelic block is itself preferably a polymer where the number of repeat units 26 m+n+p is preferably more than one for each unit, and most preferably ranging between 2 and 200 for each unit. The functional soft block may be used alone or incorporated in a segmented copolymer to effect the preparation of a new kind of SM. The SM is added to a commodity polymer or "base" polymer that has desired bulk properties. The resulting blend is represented schematically in FIG. 1. The SM determines the surface properties by virtue of concentration of the SM at the surface, or air-polymer interface 28 as shown in FIG. 2, during ordinary processing conditions such as coating or extrusion.

There are two general ways that an SM may be employed. One is literally as an additive. That is, the SM is added to some substrate system such as a liquid or solid coating composition. A second way is to spray or coat an extremely thin film on an already formed object such as a filter (e.g., the SM alone or with the bulk polymer are sprayed or coated onto the surface of a filter with the SM migrating to the surface of the coating). In either case, the combination of properties provided by the soft block structure illustrated in FIG. 2 will assure that the function of interest will be surface concentrated.

The SM of this invention is generated in different ways. One method starts with the synthesis of monomers with suitable functions, the polymerization of monomers to co-macromonomers (co-telechelics), and the generation of an SM by incorporating the co-macromonomers into a polymer. A second method involves the modification of an SM polymer to generate the desired functional SM.

Figure 3:
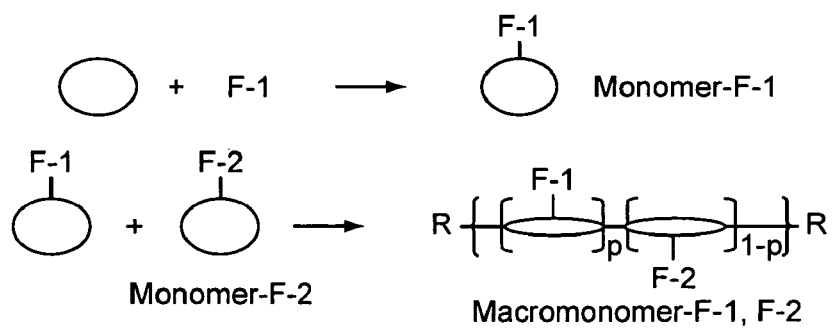
FIG. 3 is a schematic flow diagram showing monomer modification by introducing functional groups, and copolymerizing to form a telechelic.

With reference to FIGS. 3 and 4, the circle represents a cyclic monomer substrate; R or $R^1$ preferably represents a reactive functional group introduced in ring opening polymerization such as the hydroxy group —OH or amino group —$NH_2$; P is the mole fraction of monomer containing function F1; A and B are polymer forming moieties such as isocyanates and alcohol terminated chain extenders (reactive groups $R^2$ and $R^3$), respectively, for polyurethane formation for example, isocyanates and amine terminated chain extenders for polyurethane urea formation for example, or only monomer or polymer "A" might be needed (e.g., a dicarboxylic acid) for ester formation, for example.

With reference to FIG. 3, the SM may be generated by synthesizing monomers F1 and F2 (F2 may itself be synthesized by similar procedures used for F1), and then copolymerizing the monomers. This creates a macromonomer having F1 and F2 functions, and the macromonomer itself may be a soft block or polymer. In a preferred embodiment, the macromonomer is incorporated into (e.g., polymerized with or grafted on, etc.) another polymer at either or both of its end groups R to form the desired SM. See, for example, the creation of a copolymer with monomers A and B and the macromonomer containing F1 and F2 in FIG. 4. In the present invention, either F1 or F2 must be a segmer which preferentially migrates to the surface of a polymer during casting, extrusion, coating, etc. Once formed, the macromonomer (FIG. 3) and/or polymer containing the macromonomer (FIG. 4) which separately or together are the surface modifiers (SM) is mixed (typically 2% by weight or less) into a desired base polymer to give a solid with a modified surface as shown in FIG. 1.

Figure 5:
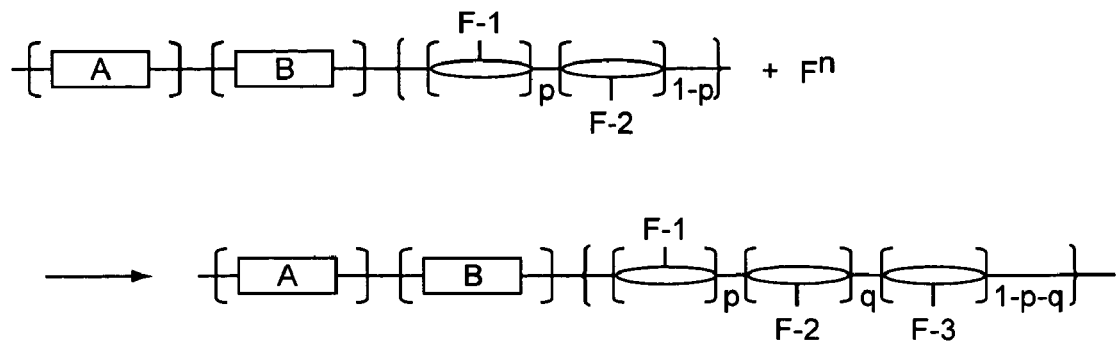
FIG. 5 is a schematic flow diagram showing the subsequent modification of the SMA of FIG. 4 to introduce a desired functionality.

FIG. 5 shows an existing SM containing macromonomer (e.g., a polymer containing A, B, and soft block containing F1 and F2) being modified to include a desired functionality F3. Here, a desired functionality F3 is introduced by reaction of an existing SM with Fn to give a new SM polymer. Supposing that Fn reacts with F2 to give F3, the reaction may be complete, in which case q is zero. However, if Fn reacts with F2 to give F3, the reaction may be incomplete, in which case q is finite and the macromonomer (SM polymer) contains three functional repeat units F1, F2, and F3. Examples of Fn include pre-biocidal moieties such as 5,5-dimethylhydantoin, hydrophilic groups such as polyethylene oxide moieties (e.g., $CH_3O(CH_2CH_2O)$n-, where n=0-15), alcohols (such as —$(CH_2)$nOH), or where n=1-0); and/or amines, such as —$(CH_2)$n$NH_2$, where n=1-10), chromophoric groups, alkylammonium groups (that may have biocidal character) such as (—$NH_2(CH_2)$nH—)$^+$, where n=1-20, and combinations ("libraries") of these groups to generate surfaces with specialized properties such as wetting behavior, response to acidic and/or basic conditions or selective detection of target molecules, and/or biocidal activity.

Another example of Fn is a group that has protected functionality such as a —$Si(OR)_3$ group (where, for the alcoxy groups, R=—$(CH_2)$nH, where n=1-5, and includes Me, Et, isopropyl, propyl, etc.), and acetato, and other hydrolysable groups). By "protected" is meant that upon exposure to a suitable reagent, a chemical change takes place that produces a new kind of functionality. In the case of —$Si(OR)_3$, exposure to moist air or mild acid produces the —$Si(OH)_3$ group which is hydrophilic and can undergo a crosslinking reaction to produce a siliceous domain by well known condensation reactions releasing water. This importance of this approach is that a —$Si(OH)_3$ group would normally not migrate to the air polymer interface as it is a high energy group that prefers to remain in the bulk.

The functional group F2 (or F3) could be a trimethylsilyl or similar group such as an oligosiloxane (—$(CH_2)_n$[$Si(Me_2)O$]m$SiMe_3$). This cotelechelic may have some unusual combination of hydrophobic/oleophobic behavior as surface active groups such as semifluorinated groups (F1) are oleophobic and hydrophobic, but groups such as trimethylsilyl (or oligosiloxane) are only hydrophobic (but not oleophobic).

In testing the new approach to surface functionalization contemplated by this invention, the C—Br group has been introduced as a model functionality, and is described in detail in Example 1. Another group of macromonomers containing $CH_3O(CH_2CH_2O)n$- has been prepared to test the surface modified additive approach of the present invention, and is described in detail in Examples 2 and 3. Examples 1, 2 and 3 fall into class I described by FIG. 3 (co-monomers→cotelechelic→polyurethane SMA with cotelechelic-derived soft block). Examples 4 and 5 describe a "reaction on polymer" approach as described in FIG. 5.

Figure 6:
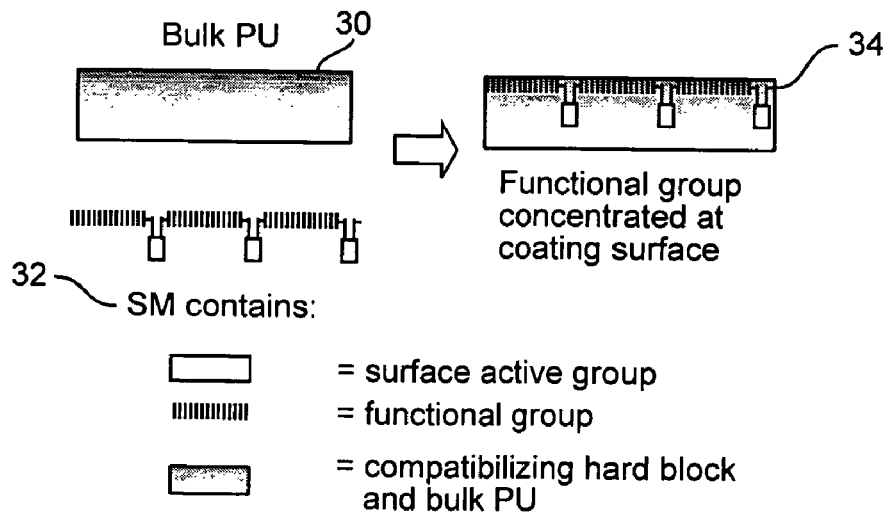
FIG. 6 is a schematic representation of a polyurethane surface modifier.

In one embodiment, the SMs can be polyurethanes. Polyurethanes (PU) are used in a variety of applications, and are an excellent model for the general application of the present invention because of their broad use and robust character. The general scheme for polyurethane surface modifiers is shown in FIG. 6, where a bulk polyurethane 30 is combined with a surface modifier 32 which contains an active group, a functional group, and a compatibilizing hard block to yield a product 34 with a functional group concentrated at the coating surface. In this specific embodiment of the general concept, surface active (chaperone) and functional groups are incorporated into the soft block. This approach takes advantage of both surface concentration of soft blocks and surface-philicity of fluorinated groups. Further details are provided in Examples 4 and 5.

Figure 7:
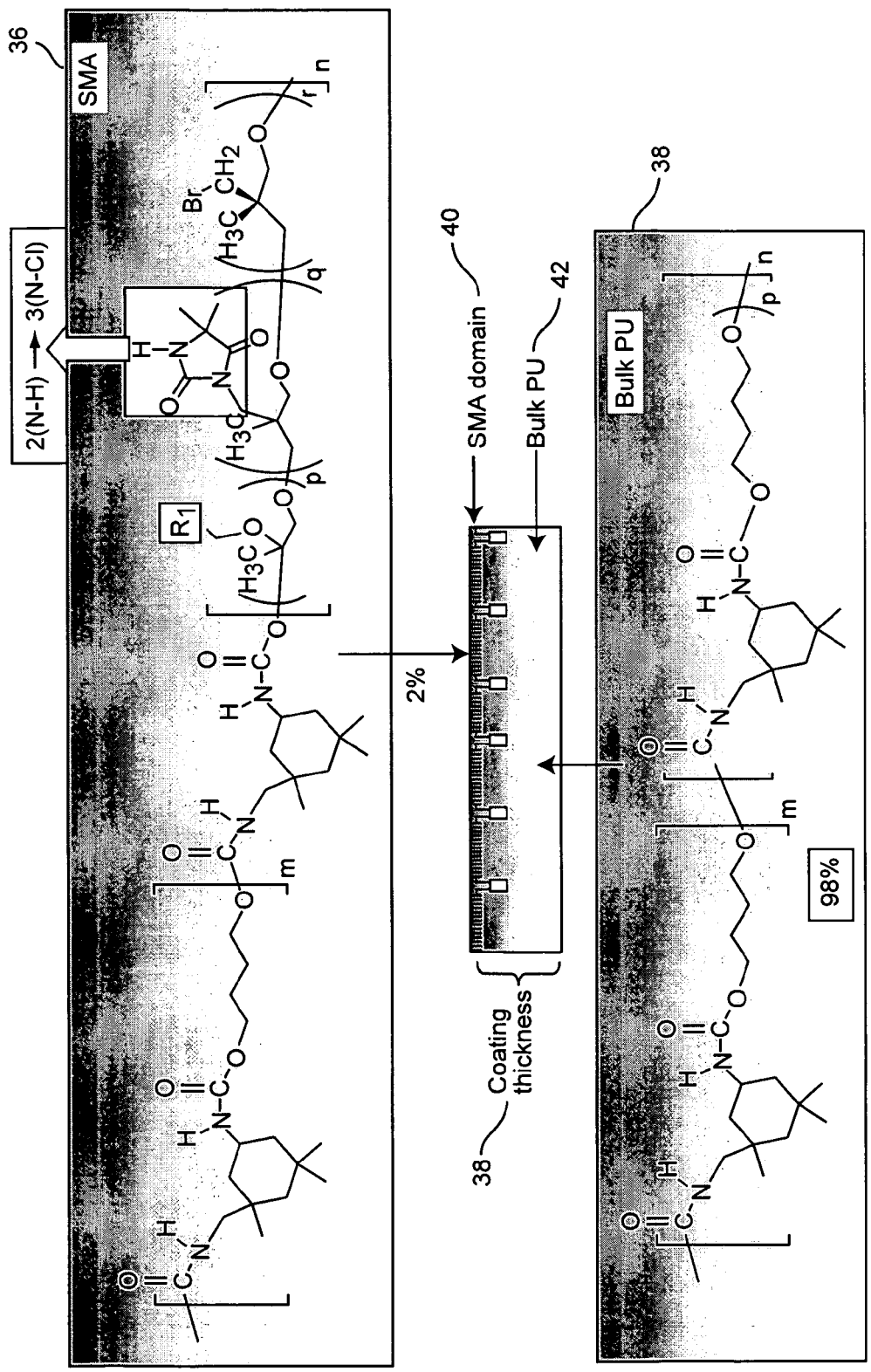
FIG. 7 is a schematic diagram showing surface functionalization via the inventive SMA approach illustrated by the addition of 2% gen-1-SMA (PU-SMA 2) to and IPDI/BD/PTMO polyurethane (PU-1), where the conversion of near surface amide to a chlorimide SMA-Cl, is highlighted in a box at the top.

The specific functionality incorporated in the soft block in Example 1 is a reactive —C—Br group. In Examples 2 and 3, a hydrophilic ethylene oxide moiety is introduced. In Example 4, a hydantoin, 5,5-dimethylhydantoin is introduced, which confers on the surface of the SMA itself unusual wetting behavior. In Example 5, the surface-concentrated pre-biocide depicted in FIG. 7 is reacted with bleach to generate surface concentrated, biocidal chloramide function. However, it should be understood that a wide variety of functionalities (that is groups other than the F3 (FIG. 5) prebiocidal hydantoin group) could be used in the practice of this invention including without limitation the groups noted above.

In order to obtain surface-active telechelics bearing reactive groups, co-telechelics containing semifluorinated and bromomethyl groups can be prepared. 3-bromomethyl-3-methyloxetane (BrOx) is readily available and offers a reactive group for subsequent derivitization. Co-polymerization of BrOx with 3FOx (—$CH_2CF_3$) and 5FOx (—$CH_2CF_2CF_3$) is contemplated in this exemplary process. Using the FOx/BrOx telechelics, polyurethanes were prepared employing isophorone diisocyanate (IPDI)/butane diol (BD) hard blocks. Most work was done using a 40% hard block polyurethane IPDI-BD(40%)-3FOx/BrOx(1:1), where 40% is percent hard block and 1:1 signifies the mole ratio of 3FOx to BrOx. Example 1 provides details.

As described in Example 5, the pre-biocidal functional group 5,5-dimethylhydantoin (Hy) was introduced into by a "reaction on polymer" carried out in dimethyl formamide (DMF). FIG. 7 shows the resulting SM 36 as IPDI-BD-(3FOx/BrOx/HyOx)(1:0.3:0.7) where HyOx is a substituted oxetane segmer containing the hydantoin moiety. This was combined with bulk polyurethane 38 (conventional IPDI-BD-PTMO-2000 (40% hard block) polyurethane) at 2 wt % SM 36, 98 wt % bulk polyurethane 38 mixture. The coating 38 thus formed included an SM domain 40, and a bulk polyurethane domain 42. Evidence for the surface concentration of 2% SM-98% polyurethane came from Wilhelmy plate analysis and biocidal activity.

It will be understood that the concentration of the SM in the polymeric article or coating to be formed can vary depending on the application. It will typically constitute 10% or less by weight, and most preferably 0.1-3 weight percent of the polymeric article or coating. Even lower percentages may be adequate depending on the application and the SM composition and processes. Some SMs are more efficient surface concentrators than others.

As will be discussed below, this invention can be employed to make a biocidal SM such that a polymeric article or coating formed according to the invention has an underlying bulk polymer domain and a surface domain having a SM with biocidal activity. This might, for example, be especially useful in the hospital or clinic setting wherein gloves, countertops, examining tables, surgical equipment and tools, devices such as catheters, wall paper, surfaces of computer keyboards, cellphones and pagers, and cabinetry can have polymer coating that provides a biocidal activity. The biocidal activity may also be useful in other settings such as schools and offices where large numbers of people are gathered. The biocidal activity may be useful in modifying air filters, by, for example, applying a microcoating on the filter material or creating the filter from the SM and bulk polymer mixture, so as to not only trap pathogens or agents but to inactivate them.

It should be understood that the invention can be used to impart a surface domain to a bulk polymer where the surface domain has a variety of other desired activities. For example, in automobile applications it may be desirable to apply a polymer coating where the surface domain repels water or corrosive agents. This would require forming an SM with functional group segmers that make the surface of the polymer coating more repellant to water (e.g., combining both fluorinated groups (F1) with trimethylsilylated (or oligosiloxane) groups (F2) as noted above might be used. Conversely, in paper or sign making applications where it is desirable to accept dyes, colorants, paints, or the like, the SM would be formed with functional group segmers that make the polymer coating more hydrophilic (e.g., hydrophilic groups such as polyethylene oxide moieties (e.g., $CH_3O(CH_2CH_2O)n$-, where n=0-15), alcohols (such as —$(CH_2)nOH$), or where n=1-10); and/or amines, such as —$(CH_2)nNH_2$, where n=1-10) and their derived ammonium salts (as —$(CH_2)nNH_3^+$, where n=1-10), chromophoric groups, alkylammonium groups such as (—$NH_2(CH_2)nH)^+$, where n=1-20, and combinations ("libraries") of these groups to generate surfaces with specialized wetting behavior properties.

As another example, it may be desirable to provide a means for functionalizing the surface of the polymer with leaving groups (e.g., Br) such that the surface could be derivitized with compounds of interest. In this instance, the invention may allow the formation of diagnostic chips that have DNA, RNA, amino acids, amino acid sequences, or other biological materials of interest bonded to the surface of a polymer coating by way of interaction with the functional leaving group.

As yet another example, the surface of a polymer can include a functional segmer which enables a fluorescent, phosphorescent, chemiluminescent, or color change reaction to occur when the functional segmer is in contact with a particular agent. This property would find sensing/detection utility in diagnostic devices, as well as in applications such as signs and displays. In still another application of the invention, fiber optics can be extruded where the surface of the optic includes the surface-active agent, which thus encircles the core. For example, in the fiber optic application, the surface modifier might prevent UV or other radiant energy from transmission to the core or, by virtue of interaction with the evanescent surface wave might act as an optical sensor/detector.

In the exemplary case of a biocidal SM [FIG. 7, Example 5], the SM was prepared via the method shown in FIG. 5, wherein "A" and "B" together represent a hard block in a polyurethane (PU) derived from isophorone diisocyanate (A) and butane diol (B). The low Tg block is a copolymer where F1 is a fluorinated group (3-FOx) and F2 is a bromomethyl group. In this case, not all the bromomethyl groups are replaced by biocide precursor 5,5-dimethylhydantoin (F3) so that the resulting SM has three repeat units (F1, the fluorinated group, F2, the unreplaced bromomethyl groups, and F3, the pre-biocidal moiety 5,5-dimethylhydantoin). The resulting SM has been added to a base polyurethane, treated with bleach to generate the biocidal N—Cl group (N-halamine) and tested against several pathogens. N-halamines are discussed in detail in U.S. Pat. No. 6,469,177 to Worley, which is herein incorporated by reference. As discussed in detail in Example 5, in 30 min exposure, 99.999% or >5.2 log reduction of *Pseudomonas aeruginosa* was observed against a suitable control. This sets a minimum for biocidal activity as no surviving bacteria were found after exposure to the SM modified PU. Similar results were obtained for *Staphylococcus aureus* and *E. coli*.

The synthesis and characterization of nonionic detergents is well known. Such molecules have an amphiphilic structure. That is, one end of the molecule may be hydrophilic, while the other end is oleophilic. Molecules that have one hydrocarbon end one poly(ethylene oxide) end are examples. The bifunctional telechelics described herein may find use as polymeric nonionic detergents. For example, the block telechelics described in Example 2 have a fluorocarbon end (hydrophobic, oleophobic) and an oligomeric ethylene oxide end (hydrophilic). Such architecture is uncommon. This architecture would mediate between fluorocarbon-like and water-like phases. For example, such a detergent might be useful in emulsifying materials that are insoluble in water, supercritical $CO_2$, or other solvent. Such a structure could prevent phase separation between immiscible polymers.

Even the random copolymer may be useful as a nonionic detergent because of the extreme difference solubility parameter between fluorinated substituents (that can be widely varied) and hydrophilic side chains (that can also be widely varied). This application would be novel for all binary and ternary combinations of:

Oleophilic groups such as (—$CH_2$)nH, tetramethylene oxide, isomeric hydrocarbon and hydrocarbon-halocarbon (—CHxCl)H, ketone containing, side chains Hydrophilic groups such as aforementioned oligomeric and polymeric ethylene oxide, alcohol, carboxylic acid, amine containing side chains Fluorous groups such as those aforementioned [e.g., —($CH_2$)n($CF_2$)mF, —($CH_2$)n($CF_2$)mH) where n is typically 1-10 and m is typically 1-12].

In view of the contemplation of use of molten salts as reaction media and other applications for amphiphilic (and even triphilic) molecules, molecules with cationic (typically alkyl ammonium) or anionic (typically carboxylate, sulfate, sulfonate, phophonate) functionality are readily envisaged and could be used in combination with oleophilic, hydrophilic, and fluorous groups described above.

Example 1

Homo- and copolymerization of BrOx and FOx monomers were carried out by a modification of the procedure reported by Malik. [Malik, A. A.; Archibald, T. G.; GenCorp: US, 2000.] Cationic ring opening polymerization was employed with $BF_3$ dietherate and 1,4-butanediol as catalyst and co-catalyst, respectively, to give the desired telechelic. A typical procedure follows.

Copolymerization of 3-trifluoroethoxy-3-methyloxetane (3FOx) and 3-bromomethyl-3-methyloxetane (BrOx) monomers were carried out by a modification of a published procedure. Cationic ring opening polymerization was employed using $BF_3OEt_2$ and 1,4-butanediol as catalyst and co-catalyst, respectively. Methylene chloride (5.54 ml) was poured into a round bottom flask under nitrogen. 1,4-butanediol (0.77 g, 8.54 mmol) and $BF_3OEt_2$ (2.45 g, 17.27 mmol) were added into reaction medium and stirred at room temperature for 45 min under nitrogen purge. Then the solution was cooled to −20° C. by using dry/aqueous isopropyl alcohol mixture. Mixture of 3FOx and BrOx monomers (e.g., total 30.09 g, 172.43 mmol) in methylene chloride (42.10 ml) was added drop wise with an addition rate of 170 drops/min. The reaction temperature was kept at −25 to −30° C. by addition of extra dry ice for 5 hrs. The reaction mixture was then brought to room temperature and quenched with 50 ml of water. The organic phase was separated, washed with 2 wt % aqueous HCl and NaCl solutions and then precipitated into methanol/water mixture (5:1). The precipitated macromonomer was placed into vacuum oven for overnight drying at 50° C., 4 Torr. The product was viscous, slightly opaque with more than 85% yield.

A number of FOx-BrOx telechelics were made by a similar procedure. The compositions and molecular weights are shown in Table 1 below:

TABLE 1

Compositions and molecular weights of telechelic poly(oxetanes).

| | Monomer feed ratio[a,b] | | | Poly(oxetane)telechelics | | |
|---|---|---|---|---|---|---|
| Telechelic | 3FOx | 5FOx | BrOx | FOx:BrOx[c] | $D_p^c$ | $MW^{c,d,e}$ |
| 3FOx | 1.0 | — | — | — | 18.5 | 3400 |
| 5FOx | — | 1.0 | — | — | 24.2 | 5660 |
| BrOx | — | — | 1.0 | — | 17.1 | 2820 |
| 3FOx:BrOx-1:1 | 1.0 | — | 1.0 | 1.2:1.0 | 27.0 | 4710 |
| 3FOx:BrOx-2:1 | 2.0 | — | 1.0 | 2.2:1.0 | 26.5 | 4700 |
| 3FOx:BrOx-1:2 | 1.0 | — | 2.0 | 1.0:1.7 | 19.6 | 3360 |
| 5FOx:BrOx-1:1 | — | 1.0 | 1.0 | 1.2:1.0 | 20.5 | 4085 |
| 5FOx:BrOx-2:1 | — | 2.0 | 1.0 | 1.9:1.0 | 11.9 | 2500 |
| 5FOx:BrOx-1:2 | — | 1.0 | 2.0 | 1.0:1.8 | 18.1 | 3400 |

[a]Monomer/catalyst ($BF_3$—$OEt_2$) mole ratio = 10.
[b]Catalyst ($BF_3$—$OEt_2$)/cocatalyst (1,4-butanediol) mole ratio = 2.02.
[c]Determined by $^1$H-NMR end group analysis.
[d]$M_n$ by GPC with PS standards (universal calibration): BrOx; 2600, 5FOx:BrOx-1:2; 5800, 3FOx:BrOx-1:2; 4100
[e]Polydispersities for these three telechelics by GPC were: BrOx1.58, 5FOx:BrOx-1:2; 1.35, 3FOx:BrOx-1:2; 2.04.

Molecular weights were obtained by integrating the high field methylene peaks next to the trifluoroacetyl group at 4.2-4.3 ppm and methyl peaks in FOx at 0.92 ppm ($CH_3$, FOx) and BrOx at 1.05 ppm ($CH_3$, BrOx). Table 1 lists telechelic molecular weights determined by end group analysis. In previous reports, homotelechelic molecular weights were determined by integrating the low field methyl peaks (due to terminal residues) and the main chain ones [Malik, A A.; Carlson, R. P. U.S. Pat. No. 5,637,772, 1997, which is herein incorporated by reference]. Molecular weights were determined by GPC (in THF compared to PS standards) for those telechelics not having a refractive index matching THF. The observed values for Mw and Mn (Table 1, fn.) values give the following polydispersities: 1.58 for BrOx, 2.04 for 3FOx:BrOx-1:2, and 1.35 for 5FOx:BrOx-1:2. These values are similar to those previously reported for 3FOx and 5FOx polyoxetane telechelics polymerized using the $BF_3$ THF/neopentyl glycol catalyst/co-catalyst system. [Kausch, C. M.; Leising, J. E.; Medsker, R. E.; Russell, V. M.; Thomas, R. R; Malik, A. A., Synthesis, characterization, and unusual surface activity of a series of novel architecture, water-dispersible poly(fluorooxetane)s, Langmuir, 2002, 18, 5933-38]

Thermal analysis. Standard and temperature modulated DSC (MDSC) starting from sub-ambient temperatures were used to measure the telechelic $T_g$ (Table 2). MDSC experiments were performed at a heating rate of 3° C./min with a modulation temperature of ±0.5° C./min. It is important to note that all telechelics have low glass transition temperatures characteristic of polyols used as soft blocks in polyurethanes.

TABLE 2

Measured and calculated glass transition temperatures of homo and co-telechelics.

| Homo or Co-telechelic Poly(oxetane) | $T_g$ (° C.) (DSC) | $T_2$ (° C.) (Calculated[a]) |
|---|---|---|
| BrOx | −24 | — |
| 3FOx | −51 | — |
| 5FOx | −48 | — |
| 3FOx:BrOx-1:2 | −33 | −32 |
| 3FOx:BrOx-1:1 | −37 | −36 |
| 3FOx:BrOx-2:1 | −38 | −39 |
| 5FOx:BrOx-1:2 | −34 | −33 |
| 5FOx:BrOx-1:1 | −36 | −36 |
| 5FOx:BrOx-2:1 | −39 | −39 |

([a] = from the Fox equation)

Polyurethanes containing FOx-BrOx soft blocks. A number of SM polyurethanes were synthesized. The compositions are summarized in Table 3. In designating compositions, such as IPDI-BD(40)/3FOx:BrOx-1:1(4700), the hard block composition is followed with hard block wt % in parentheses. The hard segment concentration was utilized was 40-45 wt %. PUs having lower hard block content (25-35%) are mechanically very soft while those with higher hard block content (45-60%) are rigid. The hard block content in an SM application could thus be varied to optimize compliance with the substrate polymer.

Representative FOx-BrOx polyurethane synthesis. A typical synthesis is represented by the synthesis for IPDI-BD(40)/3FOx:BrOx-1:1(4700). The polyurethane (PU) was synthesized in 3-neck round bottom flask. Oxetane polyol, 3FoxBrOx(1:1), (9.23 g, 1.92 mmol) was introduced into the flask with isophorone diisocyanate, IPDI, (4.44 g, 19.97 mmol). Dimethyl formamide, DMF, (3.13 g) was added into the reaction mixture as solvent. The initial % solid was 81%. The solution was heated and stirred with an over-head stirrer under nitrogen purge and with condenser. 7 drops of dibutyltin dilaurate catalyst, T-12, (1 wt % in toluene) was added to reaction medium when the reaction temperature was 65-70° C. The mixture was stirred for 3 hours at this temperature range. The reaction was followed by FT-IR. After 3 hours the prepolymer was ready for chain extension. 1,4 butane diol, BD, (1.61 g, 17.87 mmol) was used as chain extender. The reaction was frequently diluted with DMF as the polymer molecular weight increases. Chain extension took place at the same temperature range (65-70° C.). The reaction was followed with FT-IR. The reaction continued until all the isocyanate (NCO) was consumed. The final PU has slightly yellow color and the final concentration of the mixture was 43%. The resulting PU was then precipitated into methanol for purification. The solution cast PU films were prepared.

Table 3 provides compositions, molecular weights, and DSC information. We were not able to synthesize a 5FOx homo-telechelic polyurethane. The reaction mixture phase separated during the chain extension apparently due to the different solubility parameters of 5FOx.

TABLE 3

Molecular weights, and glass transition temperatures of polyurethanes

| Designation | | $M_n$ (×10³) | $M_w$ (×10³) | PD | $T_g^a$ (ss) | $T_g^b$ (hs) | Phase Sep[c] |
|---|---|---|---|---|---|---|---|
| IPDI-BD(50)/PTMO(2000) | Base PU | 23.3 | 52.5 | 2.26 | −46 | 38 | 0.76 |
| IPDI-BD(40)/BrOx(2800) | PU-1 | 19.4 | 42.9 | 2.21 | −10 | 56 | 0.81 |
| IPDI-BD(40)/3FOx(3400) | PU-2 | 17.5 | 37.4 | 2.14 | −37 | 46 | 0.84 |
| IPDI-BD(40)/3FOx:BrOx-2:1(4700) | PU-3 | 18.9 | 46.0 | 2.43 | −29 | 73 | 0.89 |
| IPDI-BD(40)/3FOx:BrOx-1:1(4700) | PU-4 | 17.9 | 36.8 | 2.05 | −29 | 62 | 0.90 |
| IPDI-BD(40)/3FOx:BrOx-1:2(3400) | PU-5 | 16.5 | 33.9 | 2.06 | −24 | 56 | 0.89 |
| IPDI-BD(40)/5FOx:BrOx-2:1(2500) | PU-6 | 18.9 | 40.1 | 2.12 | −27 | 57 | 0.88 |
| IPDI-BD(40)/5FOx:BrOx-1:1(4100) | PU-7 | 29.6 | 61.2 | 2.07 | −25 | 64 | 0.89 |
| IPDI-BD(40)/5FOx:BrOx-1:2(3400) | PU-8 | 16.6 | 33.8 | 2.04 | −29 | 64 | 0.89 |
| IPDI-BD | Hard Block | 17.2 | 31.8 | 1.85 | NA | 85 | na[d] |

[a]Soft segment (ss) glass transition temperature.
[b]Hard segment (hs) glass transition temperature.
[c]Weight fraction (±0.xx) soft block in the soft-segment phase, calculated by using the Fox equation.
[d]Not applicable.

soft block segmers are next, followed by their mole ratio and $M_n$ in parenthesis. The segmented PUs were synthesized in a conventional two-step procedure as shown in Scheme 2. First, an excess of IPDI was added to telechelic. When all the alcohol groups were consumed, BD chain extender was added until no isocyanate absorption was detectible by FT-IR. As the viscosity increased, DMF or THF/DMF was added so that the solution contained about 30-40% solids at the end of the reaction. PUs having different concentrations of soft block can be obtained simply by changing the ratio of telechelic to chain extender (1,4-butanediol) ratio.

Molecular weights. Molecular weights, and polydispersities of the new polyurethanes are shown in Table 3. GPC analyses gave $M_w$s in the range of 30-60,000. With one exception, $M_w$s for the FOx:BrOx polyurethanes have somewhat lower $M_w$s compared to the conventional PTMO analog. While molecular weights are modest, all the polyurethanes formed smooth, optically transparent coatings and freestanding films.

Wetting Behavior. Polyurethane wetting behavior was determined by the Wilhelmy plate method using a Dynamic Contact Angle Analyzer (DCA). The Wilhelmy plate experiment has been discussed in connection with the measurement of intrinsic contact angles for model PDMS networks. [Uilk, J. M.; Mera, A. E.; Fox, R. B.; Wynne, K. J., Hydrosilation-cured poly(dimethylsiloxane) networks: Intrinsic contact angles via dynamic contact angle analysis, Macromolecules, 2003, 36, 3689-3694.] Remarkably, all of the co-telechelic polyurethanes have higher $\theta_{adv}$ and lower $\theta_{rec}$ than the parent homo-telechelic PUs (Table 4).

TABLE 4

Advancing and receding contact angles for PUs.

| PU(ratio)[a] | Cycle-1 Adv/Rec | Cycle-2 Adv/Rec | Cycle-3 Adv/Rec | Cycle-4 Adv/Rec | Cycle-5 Adv/Rec | Water Con. |
|---|---|---|---|---|---|---|
| Base PU | 84/55 | 82/55 | 82/56 | 81/56 | 81/56 | No |
| PU-1 | 102/42 | 101/41 | 101/41 | 101/40 | 101/40 | No |
| PU-2 | 105/45 | 99/45 | 98/45 | 98/46 | 98/46 | Yes |
| PU-3 (2:1) | 108/35 | 108/35 | 108/35 | 108/34 | 108/34 | No |
| PU-4 (1:1) | 116/33 | 115/32 | 116/32 | | | No |
| PU-5 (1:2) | 104/34 | 102/34 | 102/34 | 102/34 | 102/34 | Yes |
| PU-6 (2:1) | 109/38 | 108/38 | 108/38 | 108/38 | 108/38 | No |
| PU-7 (1:1) | 109/35 | 109/35 | 109/35 | 109/35 | 109/35 | Yes |
| PU-8 (1:2) | 107/36 | 106/36 | 106/36 | 106/36 | 106/36 | Yes |

[a]Ratio of nFOx:BrOx. n = 3 for PU-3, 4, and 5. n = 5 for PU-6, 7, and 8.

The most surprising result for PU co-telechelics ($\theta_{adv}$, 116°; $\theta_{rec}$, 32°) is the wetting behavior of PU-4, IPDI-BD (40)/3FOx:BrOx-1:1(4700). These values are constant over three cycles and no water contamination is detected. The very stable contact angle hysteresis (84°) is noteworthy for topologically smooth surfaces (vida infra). Few polymers have $\theta_{adv}$ that exceed 116°.

Surface Modifying Behavior. IPDI-BD(40)/3FOx:BrOx-1:1(4700) (2%) was added to an ordinary IPDI-BD polyurethane containing a 2000 MW poly(tetramethylene oxide) soft block. X-ray photoelectron spectroscopy demonstrated surface concentration of the SM by virtue of Br and F analysis that was similar to IPDI-BD(40)/3FOx:BrOx-1:1(4700) alone. These results demonstrate the efficacy of surface concentration of the reactive C—Br function. That is, a function which contains a Br leaving group that allows modification of the polymer after formation of the polymeric article or coating.

Example 2

Monomer synthesis. 3-(Methoxyethoxyethoxymethyl)-3-methyloxetane (ME2Ox) was synthesized using phase transfer catalysis (PTC). A mixture of 2-(2-methoxyethoxy)ethanol (60.1 g, 0.5 mol), BrOx (82.5 g, 0.5 mol), TBAB (8.0 g, 0.025 mol) and water (20 ml) was stirred and heated to 75° C. Then, a solution of KOH (35.5 g, 87%, 0.55 mol) in water (50 ml) was added. The reaction mixture was stirred vigorously at 80-85° for 7 hrs. The mixture was cooled to room temperature, filtered, and diluted with water. The product was extracted with methylene chloride and distilled at 100° C./8 mmHg. ME2Ox monomer; 1H-NMR (CDCl$_3$) δ3.67 (—CH$_3$, 3H, s), δ3.39 (—OCH$_3$ 3H, s), δ3.55 (—OCH$_2$CH$_2$O—, 4H, m), δ3.67 (—OCH$_2$CH$_2$O—, 4H, and —CH$_2$—, 2H, m), δ4.35 (ring —CH$_2$—, 2H, d), δ4.52 (ring CH$_2$, 2H, d); $^{13}$C-NMR (CDCl$_3$) δ21.5 (—CH$_3$), δ40.0 (—C—), δ59.1 (—OCH$_3$), δ70.7, 71.1, and 72.1 (—OCH$_2$CH$_2$O—), δ76.6 (—CH$_2$—), δ80.2 (ring —CH$_2$—).

7FOx monomer was prepared from BrOx and 2,2,3,3,4,4,4-heptafluorobutanol by the same procedure used for ME2Ox monomer. 7-FOx monomer; $^1$H-NMR (CDCl$_3$) δ1.31 (—CH$_3$, 3H, s), δ3.67 (—CH$_2$—, 2H, s), δ3.99 (—CH$_2$CF$_2$—, 2H, t), δ4.34 (ring —CH$_2$—, 2H, d), δ4.50 (ring —CH$_2$—, 2H, d).

Homo- and Cotelechelic polyoxetane synthesis. Homo- and copolymerization of ME2Ox and FOx monomers were carried out by a modification of a published procedure for FOx and methyloxetane. [Malik, A. A.; Archibald, T. G.; GenCorp: US, 2000.] The ME2Ox homotelechilic has not been previously synthesized and is a new composition of matter. Of course, all co-telechelics are new compositions. Cationic ring opening polymerization 3-bromomethyl-3- was employed using BF$_3$ and 1,4-butanediol as catalyst and co-catalyst, respectively. Methylene chloride (10 ml) was poured into a round bottom flask under nitrogen. 1,4-butanediol (165 mg, 1.84 mmol) and BF$_3$—OEt$_2$ (520 mg, 3.67 mmol) in methylene chloride (10 ml) were added and stirred at room temperature for 45 min under nitrogen. Then the solution was cooled to 0-5° C. in ice bath, and a mixture of ME2Ox and FOx monomers (e.g., total 36.7 mmol) in methylene chloride (10 ml) was added dropwise at the rate of 0.5 ml/min. The reaction was kept at 0-5° C. for 4 hrs with stirring. The reaction mixture was then brought to room temperature and quenched with 30 ml of water. The organic phase was separated, washed with 0.2% HCl and NaCl aqueous solution and then solvent was evaporated. The product (a viscous, opaque liquid) was re-dissolved in acetone, and re-precipitated in water. The resulting viscous liquid was separated and dried in a vacuum oven at 70° C., 5 Torr overnight to give a transparent oily product with >80% yield.

ME2Ox homopolymer; $^1$H-NMR (CDCl$_3$) δ0.91 (—CH$_3$, 3H, s), δ3.19 (backbone —CH$_2$—, 4H, m), δ3.30 (—CH$_2$—, 2H, s), δ3.38 (—OCH$_3$ 3H, s), δ3.55 (—OCH$_2$CH$_2$O—, 4H, m), δ3.64 (—OCH$_2$CH$_2$O—, 4H, m); $^{13}$C-NMR (CDCl$_3$) δ17.3-17.9 (—CH$_3$), δ40.8-41.3 (backbone —C—), δ58.9 (—OCH$_3$), δ70.4 and 71.9 (—OCH$_2$CH$_2$O—), δ70.9-71.3 (—CH$_2$—), δ74.0 (backbone —CH$_2$—).

ME2Ox/5FOx (ME2Ox/7FOx) copolymer; $^1$H-NMR (CDCl$_3$) δ0.91 (—CH$_3$ for ME2Ox and FOx, 3H, s), δ3.19 (backbone —CH$_2$—, 4H, m), δ3.30 (—CH$_2$— for ME2Ox, 2H, s), δ3.38 (—OCH$_3$ 3H, s), δ3.44 (—CH$_2$— for FOx, 2H, s), δ3.55 (—OCH$_2$CH$_2$O—, 4H, m), δ3.64 (—OCH$_2$CH$_2$O—, 4H, m), 63.85 (—CH$_2$CF$_2$—, 2H, t); $^{13}$C-NMR (CDCl$_3$) δ16.9-17.8 (—CH$_3$ for ME2Ox and FOx), δ40.8-41.5 (backbone —C—), δ58.6 (—OCH$_3$), δ68.0 (—CH$_2$CF$_2$—, t), δ70.4 and 71.9 (—OCH$_2$CH$_2$O—), δ70.9-71.3 (—CH$_2$— for ME2Ox), δ73.4 (backbone —CH$_2$— for FOx), δ74.0 (backbone —CH$_2$— for ME2Ox), δ75.3 (—CH$_2$— for FOx), δ110.0-123.3 (—CF$_n$CF$_3$).

Table 5 lists the molar ratios of monomer feed as well as the compositions of polymers. Monomer/1,4-butanediol ratios were varied in order to make polyoxetanes with differing molecular weights. The degree of polymerization (D$_p$) and equivalent molecular weight are determined by end group analysis as described above. The BF$_3$—OEt$_2$/1,4-butanediol ratio was kept constant at 2.2/1, and in all compositions in Table 5, the reactions were done under nitrogen atmosphere with a temperature at 0-5° C. Monomer ratios in copolymer telechelics are very close to feed ratios.

GPC results are also listed in Table 5. The number average molecular weights (M$_n$) correlate well with end group analysis results for ME2Ox homo- and ME2Ox/FOx copolymers, but show higher values for 5FOx homopolymer. The molecular distribution has a trend that the polydispersity (M$_w$/M$_n$) decreases as monomer/co-catalyst ratio increases for all polymer series. When the monomer/co-catalyst ratio is above 22, the polydispersities are 1.9-2.2. As shown in Table 5, the $D_p$ of polymer is not directly related to the monomer/co-catalyst ratios.

Thermal analysis. Glass transition temperatures ($T_g$'s) of the polyoxetanes were measured using sub-ambient DSC. Table 6 shows $T_g$ of ME2Ox and FOx homopolymers and their copolymers. ME2Ox homopolymer has the lowest $T_g$ (−67° C.) close to the $T_g$ of PTMO (ca, −70° C.).

TABLE 6

Glass transition temperatures (Tg) for polyoxetanes

| Homo- or Copolymers | Tg (° C.) |
| --- | --- |
| ME2Ox | −67.3 |
| 5FOx | −43.5 |
| 7FOx | −52.7 |
| ME2Ox/5FOx (1/1) | −56.9 |
| ME2Ox/7FOx (1/1) | −55.6 |
| ME2Ox/7FOx (2/1) | −58.3 |

The Tg of 5FOx homopolymer is approximately −44° C. From a scan of physical mixture of ME2Ox and 5FOx homopolymers, it was observed that this mixture has two Tg's because the two homopolymers are completely immiscible. In contrast, ME2Ox/5FOx (1/1) copolymer gives one Tg at −57° C. in between the Tg's of the homopolymers. This result supports the composition study of the copolymer that indicates a random or alternating tendency but not blocky sequence. The Tg of copolymer can be estimated by the Fox equation using the T's of homopolymers:

$$T_{g(cal)}^{-1} = w_1 T_{g1}^{-1} + w_2 T_{g2}^{-1}$$

where $w_1$ and $w_2$ are weight fraction of each component. Using $w_{(ME2Ox)}$ and $w_{(5FOx)}$ and homopolymer $T_g$s, $T_{g(cal)}$ is −54° C. for ME2Ox/5FOx (1/1). Similarly, $T_{g(cal)}$ of ME2Ox/7FOx (1/1) and ME2Ox/7FOx (2/1) are −58 and −60° C., respectively. Calculated $T_g$s are close to those observed.

Example 3

As a further example for synthesis of telechelics, FOx-MEnOx telechelics were prepared where n=3 or 7. The purpose of this synthetic work was to provide F-2/F-3 groups that would have a more hydrophilic character. In short, using ring opening polymerization as described above, polyoxetane telechelics with hydrophobic semifluorinated and hydrophilic oligoalkylether pendant groups have been synthesized with random and block sequences. Polyurethanes incorporating these novel telechelics as soft blocks have also been prepared. For the first time, the effect of soft block sequence distribution on polyurethane surface morphology and wetting behavior has been demonstrated. TM-AFM reveals surface nanophase separation for the polyurethane containing a block-oxetane co-telechelic, while the polyurethane containing a random-oxetane soft block shows no surface microstructure. Wetting behavior is strongly influenced by the surface nanoscale morphology. This observation suggests that surface nanostructure must be taken into account for demanding applications such as those requiring biocompatibility or "smart" behavior.

The reaction mechanism of cationic ring-opening polymerization (ROP) of oxetane monomers using boron trifluoride ($BF_3$) has seen considerable study and the general features are known as described above. In the present work, modified reaction conditions were used to give telechelics having different monomer sequences. The goal of this work was to learn whether monomer sequence distribution would affect surface properties of derived polyurethanes.

The oxetane monomer 3-(2,5,8,11-tetraoxydodecyl)-3-methyloxetane (ME3Ox), a new compound, was synthesized from tri(ethylene glycol) monomethyether and 3-bromomethyl-3-methyloxetane (BrOx). Copolymerization of ME3Ox and 3-trifluoroethoxymethyl-3-methyloxetane (3FOx) were carried out by cationic ring opening polymerization using $BF_3$ and butane diol co-catalysts. For the preparation of block copolyoxetane ME3Ox-block-3FOx, ME3Ox monomer was added to catalyst at 0° C. for 4 hrs. Then a dilute solution ($CH_2Cl_2$) of 3FOx monomer was added dropwise slowly over 24 hrs. The reaction mixture was stirred more 12 hrs, then quenched with water and the product isolated.

To obtain a blocky-type copolymer, monomer addition order and addition speed were varied. When 3FOx monomer was polymerized first in the presence of $BF_3$—$OEt_2$ and butane diol (BD) cocatalysts and the second monomer ME3Ox was added, a mixture of homo-telechelics as a two-phase liquid mixture was obtained. Interestingly, when ME3Ox was added as the first monomer followed by 3FOx, the product was a one phase viscous liquid, indicating formation of a block copolymer (telechelic). After the reaction of first monomer ME3Ox, Mn determined by end group analysis with trifluoroacetic anhydride is 2,600. Then, after slow addition of second monomer 3FOx, Mn=4,200 for the final telechelic. A parallel increase in Mw by GPC was obtained. Table 7 contains compositions and characterization data.

GPC molecular weight determinations on telechelics usually showed the presence of a peak corresponding to cyclic tetramers. [Malik, A. A.; Archibald, T. G.; GenCorp: US, 2000] The percent cyclics present in the present work (0-20%) is not reproducible. Samples examined by DSC and $^{19}$F-NMR contained cyclics but the qualitative conclusions are deemed valid. Furthermore, once telechelics are used to prepare PUs, cyclics are removed by purification procedures, as the telechelics are nonfunctional and relatively nonpolar.

To investigate structural differences, $^{19}$F-NMR spectra were obtained. The 3FOx $CF_3$— peaks in block and random copolymers shift to low field relative to 3FOx homopolymer. A similar small chemical shift is observed when ME3Ox homopolymer is admixed with 3FOx homopolymer solutions, indicating the shift for copolymers is largely a solvent effect. A comparison of the relative peak shapes is revealing. Homo- and block-telechelics show a series of well-resolved peaks with $J_{1H-19F}$=8 Hz. In contrast, the random copolymer peak is broad with little resolvable structure. This observation supports the hypothesis that the random telechelic is comprised of random sequences with many sequence distributions. In contrast, the block co-telechelic contains (3-FOx)$_n$ sequences that mimic those in the homo-telechelic. Hence 3FOx and ME3Ox-block-3FOx telechelics have similar $^{19}$F-NMR spectra.

Polyurethanes were prepared using polyoxetane telechelics or a reference PTMO soft segment as described above for ME2Ox and FOx-BrOx telechelics. In brief, methylenediphenyldiisocyanate (MDI) and butane diol (BD) were used for hard segment with ME3Ox/3FOx copolymer soft segment. Polyurethanes were prepared via solution reaction in dimethylacetoamide (DMAc) using a two-step method (first, MDI plus soft block telechelic; second, BD chain extender). Poly(tetramethylene oxide) (PTMO), $M_n$=2,000, was used as soft block for a standard segmented polyurethane as a control sample.

Figure 8:
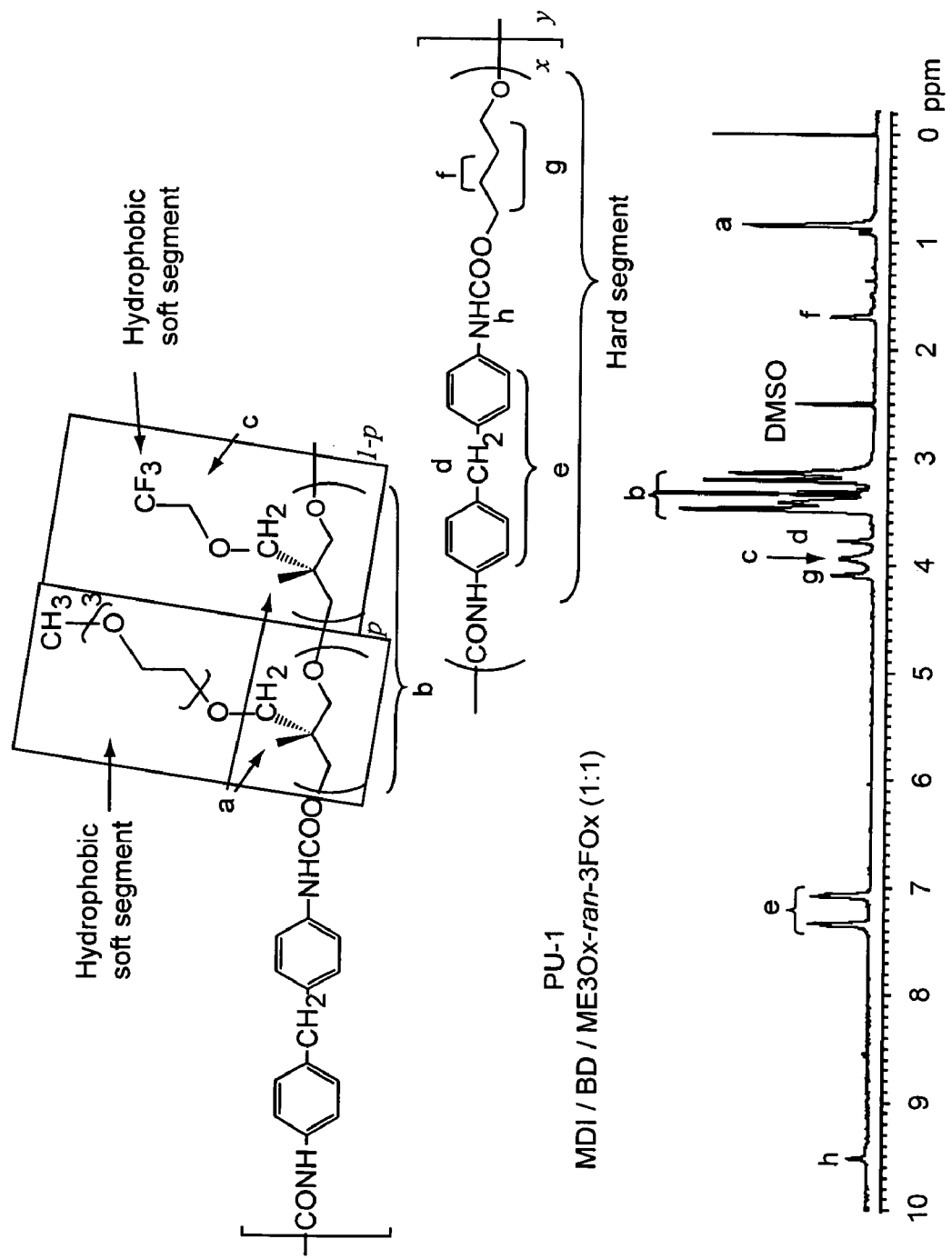
FIG. 8 shows the chemical structure and $^1$H-NMR spectrum of PU-1 containing ME3Ox-ran-3FOx copolymer soft segment in DMSO-d6.

FIG. 8 shows the structure and H-NMR spectrum of a representative PU, MDI/BD(27)/ME3Ox-ran-3FOx(1:1), PU-1 in DMSO-d6. Polyurethanes are designated: isocyanate/chain extender (hard segment wt %)/soft segment monomer 1-sequence-soft segment monomer 2 (mole ratio). Other compositions were also determined by $^1$H-NMR spectra: MDI/BD(32)/ME3Ox-block-3FOx(2:3), PU-2, and MDI/BD (36)/PTMO, PU-3. Glass slides were dip-coated from 20% DMAc solutions. The dip-coated PU films were prepared on glass slides from 20% dimethylacetamide (DMAC) at room temperature, dried at 60° C. for 5 h at ambient pressure, followed at 80° C. for 2 days under vacuum.

Figure 9:
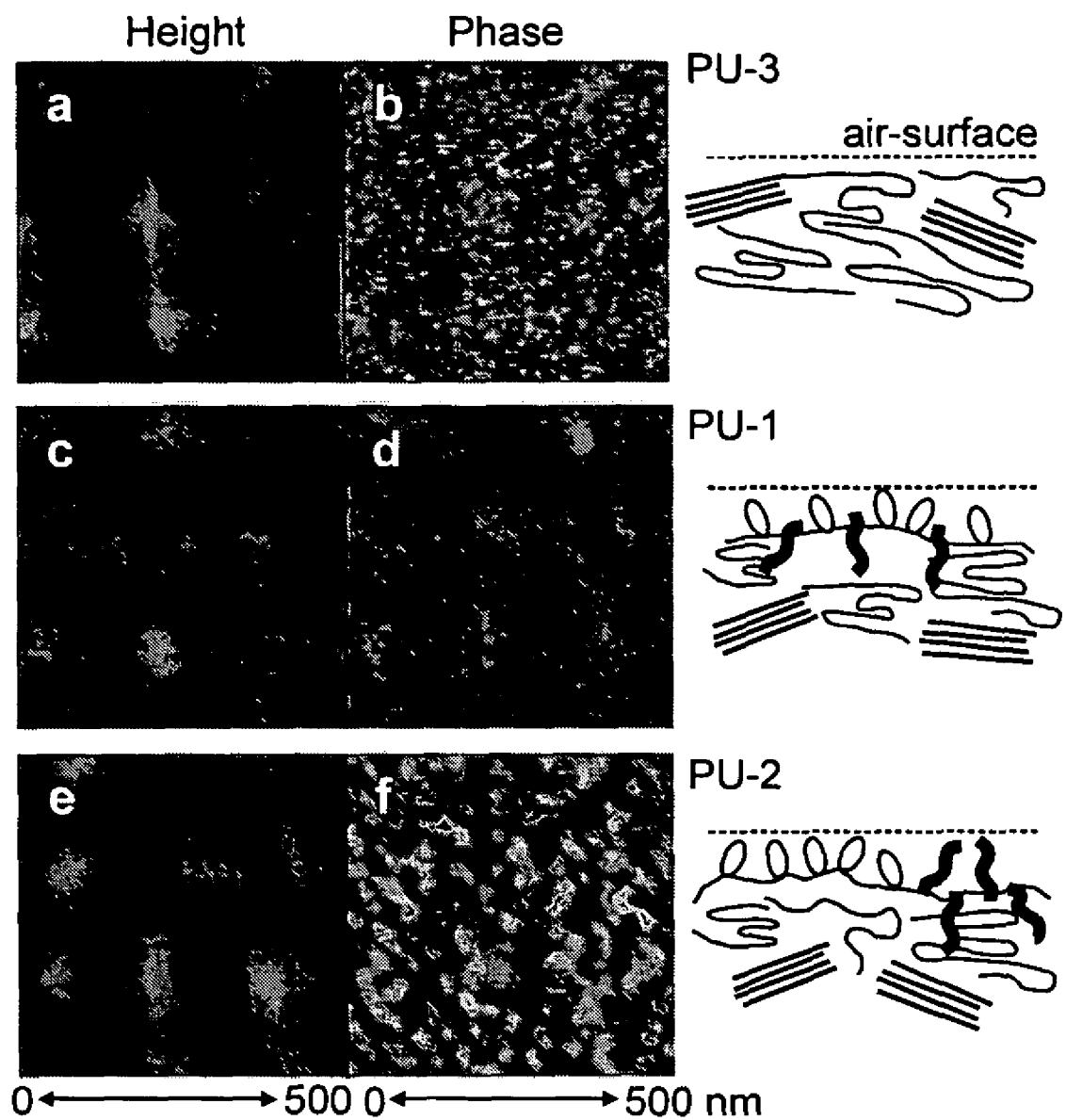
FIG. 9a-f show typical tapping-mode AFM images of polyurethane films. PU-3: containing PTMO (a,b), PU-1: containing ME3Ox-ran-3FOx (c,d), and PU-2: containing ME3Ox-block-3FOx (e,f); (a,c,e): height images at z=10 nm, and (b,d,f): phase images at z=20°; Rms: (a) 0.6 nm, (c) 0.3 nm, and (e) 0.9 nm; Tapping force (A/A$_0$): (a,b) 0.87, (c,d) 0.83, and (e,f) 0.92.

Tapping-mode AFM (TM-AFM) is a powerful method for evaluating polymer surface morphology. FIGS. 9a-f show TM-AFM images of PU films containing PTMO (PU-3), ME3Ox-ran-3FOx copolymer (PU-1), and ME3Ox-block-3FOx copolymer (PU-2). The surfaces of all films are topologically quite flat (FIG. 9a, c, e) with RMS roughness ($R_q$) less than 1 nm. Phase images of the three films are clearly different (FIG. 9b, d, f). Although tapping forces are relatively weak (A/A$_0$=0.83-0.92), phase images for PU-3 (FIG. 9b) and PU-2 (FIG. 9f) show strong contrast characteristic of nanoscale phase separation.

The surface of PU-3 (FIG. 9b) has phase separation on the order of 10 nm due to the hard and soft segments as shown schematically. This typical PU phase segregation has been observed previously. [Garrett, J. T.; Siedlecki, C. A.; Runt, J. Macromolecules 2001, 34, 7066-7070] The phase image of PU-1 containing the ME3Ox-ran-3FOx telechelic is featureless (FIG. 9d). This is consistent with a surface structure where the random-soft block predominates. With increased tapping force (A/A$_0$=0.5-0.6) a phase-separated structure appears in the phase image (data not shown), reflecting the presence of sub-surface hard blocks.

In contrast, TM-AFM of PU-2 containing the block-soft segment (FIG. 9f) shows strong nano-phase separation that is attributed to two block domains, viz., ME3Ox and 3FOx. We use a conventional interpretation of modulus-sensitive phase images at light tapping where the lighter color portions are assigned to the organized domain, in this case 3FOx. [Uilk, 2002 #533] The average domain size is about 20 nm in diameter, larger than the hard- and soft-segment segregation observed in PU-3 (FIG. 9b). The observed phase separation must reflect the immiscibility of the 3FOx and ME3Ox block segments in the liquid phase, as the blocks are 75° C. (3FOx) and 100° C. (ME3Ox) above $T_g$.

The interesting difference in nanoscale surface phase separation for PUs containing random and block co-telechelics is reflected in contrasting wetting behavior. For evaluation of surface wetting properties, dynamic contact angle (DCA) analysis by the Wilhelmy plate method was used as described in Uilk, J. M.; Mera, A. E.; Fox, R. B.; Wynne, K. J. Macromolecules 2003, 36, 3689-3694.] The RMS roughness, $R_q$, is less than 1 nm for all coatings. Thus surface roughness cannot contribute to advancing ($\theta_{adv}$) or receding ($\theta_{rec}$) contact angles or contact angle hysteresis (delta$\theta$).

As a point of reference, PU-3 containing the PTMO soft segment was examined. PU-3 has a $\theta_{adv}$ of 93° and $\theta_{rec}$ of 490. From previous work[Lamba, N. M. K.; Woodhouse, K. A.; Cooper, S. L. In Polyurethanes in Biomedical Applications; CRC Press: Boca Raton, Fla., 1998, p 15.] and our experience, $\theta_{adv}$, $\theta_{rec}$, and delta$\theta$. (44°) are fairly typical values for PTMO PUs. The moderate delta$\theta$.(44') is largely attributed to rapid surface reorganization of the low $T_g$ PTMO soft block, though TM-AFM suggests there may be a near-surface hard block contribution as well.

One approach to analysis of chemically heterogeneous surfaces using wetting behavior is to compare an "AB" surface to that of A and B alone. Several well-known methods exist to analyze nonideality responsible for surface behavior. Here, we use a qualitative comparison of cotelechelic PUs with corresponding homo-telechelic PUs. Homo-telechelic compositions and contact angles are: MDI/BD(29)/3FOx: $\theta_{adv}$, 110°, $\theta_{rec}$, 70°; MDI/BD(37)/ME3Ox; $\theta_{adv}$, 93°, $\theta_{rec}$, 32°.

Analysis of PU-1 containing the ME3Ox-ran-3FOx soft segment gave $\theta_{adv}$=104°, $\theta_{rec}$=39°, and delta$\theta$=65°. The PU-1 surface is hydrophobic in air due to fluorinated groups with $\theta_{adv}$ similar to the PU 3FOx homopolymer. However, PU-1 is hydrophilic in water ($\theta_{rec}$, 39°) with a receding contact angle closer to ME3Ox PU (32°) than to 3FOx PU (70°). Clearly, extensive surface reorganization occurs in water favoring hydrophilic ether side groups at the water polymer interface. The result is a very large contact angle hysteresis.

For PU-2 containing ME3Ox-block-3FOx, $\theta_{adv}$ (106°) is also close to $\theta_{adv}$ for the PU 3FOx homopolymer. In this regard, PU-2 and PU-1 are similar. However, $\theta_{rec}$ (56°) is 17° higher than PU-1 ($\theta_{rec}$, 39°) resulting in a smaller contact angle hysteresis for PU-2 (50°) compared to PU-1 (65°). This result indicates the PU-2 surface is hydrophobic in air like the PU 3FOx homopolymer and only moderately hydrophilic in water, more like the PU 3FOx homopolymer than PU ME3Ox. Clearly, the nanophase separated PU-2 surface structure is more hydrophobic overall than the corresponding random-soft block surface. This amplification of hydrophobicity occurs for PU-2 even though the fluorinated nanodomains do not cover the whole surface (TM-AFM, FIG. 9f). Over the limited time scale investigated thus far, the self-assembly responsible for fluorinated surface nanodomains apparently inhibits access of a significant fraction of near-surface, more hydrophilic polyether side chains to water.

This Example demonstrates for the first time, the effect of soft block sequence distribution on surface morphology and wetting behavior. Surface nanophase separation is observed for PU-2, which contains a block-oxetane co-telechelic, while PU-1, which contains a random oxetane co-telechelic, shows no surface microstructure. Interestingly, wetting behavior is strongly influenced by nanoscale surface morphology. This observation suggests that surface nanostructure must be taken into account for demanding applications such as those that require biocompatibility or "smart" behavior.

Surface Activity of MeNOx/FOx polyurethanes. While the surface properties of the SM's are interesting by themselves, a key question is "will surface properties be conferred to a substrate polymer". FIG. 10 shows a striking example of conferring surface properties to a substrate polymer. Here, only 2% MDI/BD/(ME3Ox-ran-3FOx)(1:1) (PU-1) and 2% MDI/BD/(ME3-block-3FOx)(1:1), PU-2 respectively are added to a typical base polyurethane, MDI/BD(36)/PTMO. FIG. 10 unequivocally shows that the phase separated nanoscale morphology of MDI/BD/(ME3Ox-block-3F)(1:1), PU-2 seen in FIG. 9f is conferred at a 2% loading level to the conventional MDI/BD(36)/PTMO polyurethane. Wetting behavior on the 2% modified material (shown only for the parent PU-2) is similar to the parent PU-2 and confirms that the SM PU-2 is surface concentrated. Furthermore, X-ray photoelectron spectroscopy confirms the presence of a high level of fluorine in the top 30 nm, consistent with a high 3FOx-like concentration.

In contrast, at a loading of 2% PU-1, MDI/BD/(ME3Ox-ran-3FOx)(1:1) loading level to the conventional MDI/BD (36)/PTMO polyurethane, a relatively featureless nanoscale morphology is seen, as for the parent MDI/BD(27)/ME3Ox-ran-3FOx(1:1), PU-1 (FIG. 9d). Wetting behavior on the 2% modified material (shown only for the parent PU-1) is similar to the parent PU-1 and confirms that the SM PU-1 is surface concentrated. Furthermore, X-ray photoelectron spectroscopy confirms the presence of an intermediate level of fluorine in the top 30 nm, consistent with a higher functional group (F2, hydrophilic MEnOx) concentration.

These results are of the utmost importance in demonstrating that the SM indeed modifies the surface of the commodity-like, conventional MDI/BD(36)/PTMO polyurethane. Importantly, the wetting behavior of the conventional MDI/BD(36)/PTMO polyurethane is modified by 2% incorporation of the SMs in the manner expected (data not shown).

Example 4

Reaction on polymer example: substitution of 5,5-dimethyl hydantoin (Hy) onto IPDI-BD(40)/3FOx:BrOx-1:1 (4700), PU-4, from Example 1, Table 3. The substitution reaction was carried out in dimethyl formamide (DMF). 5,5-Dimethyl hydantoin, DMH, (2.55 g, 19.90 mmol) was introduced into 3-neck round bottom flask with DMF (15.30 g). Then potassium carbonate, $K_2CO_3$, (11.06 g, 80.02 mmol) was added into the medium. $K_2CO_3$ is not soluble in DMF; it was suspended in the solvent. The mixture was heated and stirred (stirring bar) under nitrogen purge and with condenser for 1 hour. Then PU (12.27 g, 0.26 mmol) in DMF (21.01 g) was added to reaction medium drop wise. The reaction temperature was kept around 90-95° C. for 42 hours. The reaction was then terminated by cooling to room temperature. The mixture was precipitated into methanol/water (4:1) solution in order to get the final product. The resulting polyurethane was precipitated out of the solution. The degree of substitution and final yield was obtained by NMR (about 70%).

This polyurethane SM is designated 36 in FIG. 7. We refer to the material obtained by treatment of a coating of 36 alone with bleach as 36B. We refer to the composition obtained by adding 2% 36 to the bulk PU 42. First, we consider the remarkable properties of 36 alone.

Figure 11:
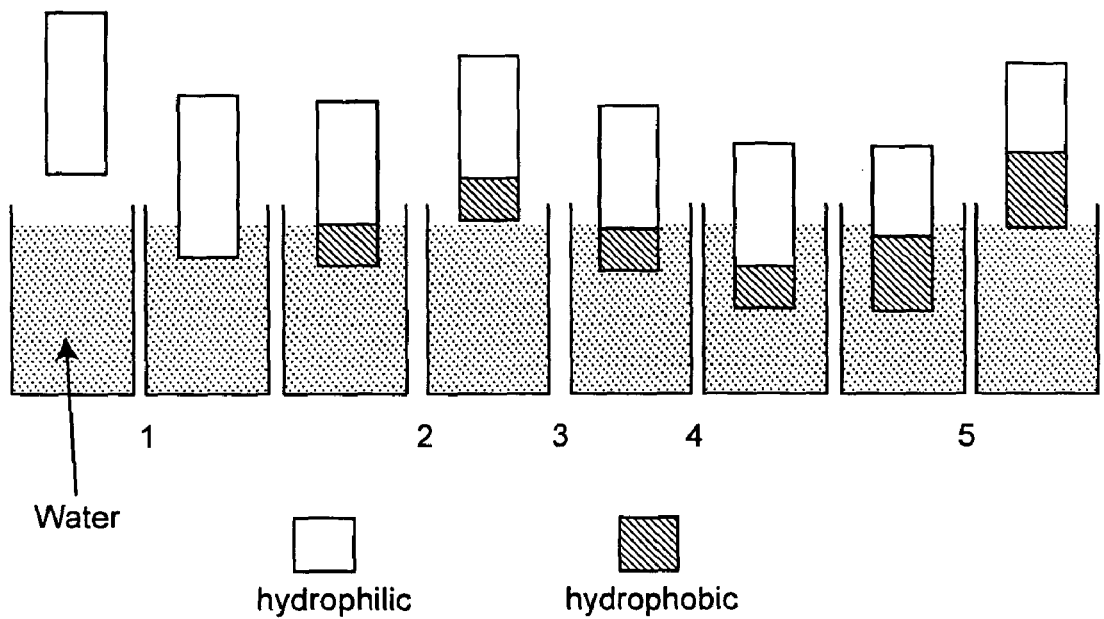
FIG. 11 is a schematic drawing showing the contraphilic properties of SMs of the present invention.

As shown in FIG. 11, coatings designated as 36 in FIG. 7 have unexpectedly unprecedented wetting behavior. All prior art demonstrates that polymers exposed to water either have no change in wetting behavior (e.g., polyethylene, polypropylene, poly(tetrafluoroethylene) due to total lack of interaction with water, or else become apparently more hydrophilic. The latter behavior is found for polymers that have some interaction with water such as nylons and polyurethanes. [Pike, J. K.; Ho, T.; Wynne, K. J., Water-induced surface rearrangements of poly(dimethylsiloxane-urea-urethane) segmented block copolymers, Chemistry of Materials, 1996, 8, 856-860.]

Figure 12:
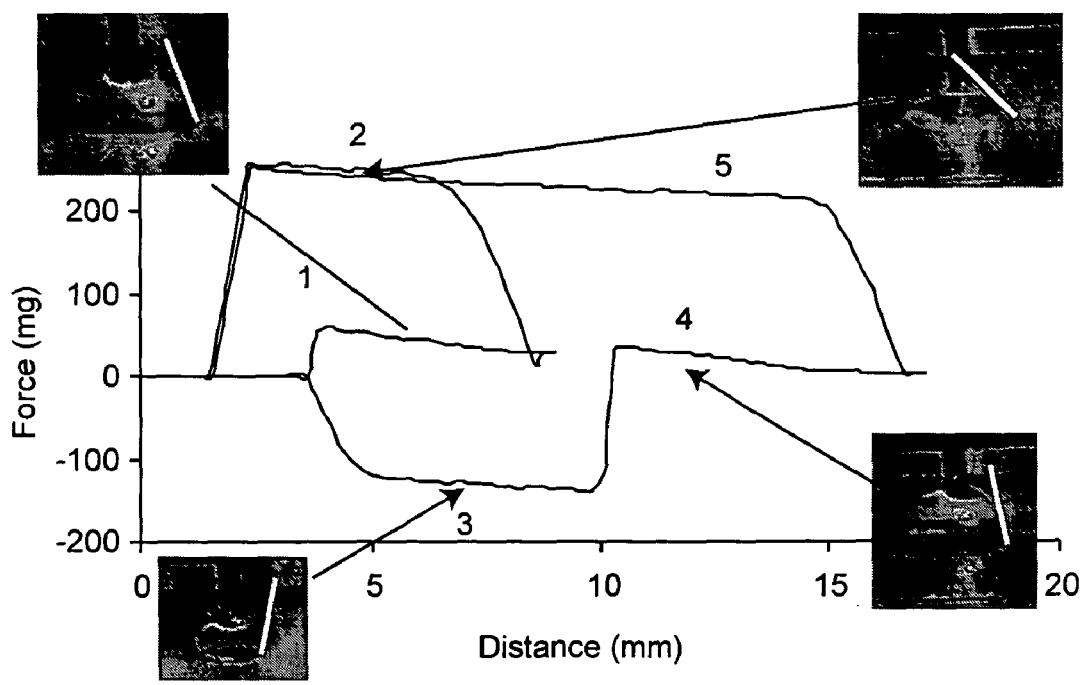
FIG. 12 is a composite of photographs and a graph showing force versus distance for contraphilic polyurethane containing hydantoin substituted poly(oxetane) soft blocks.

As shown in FIG. 11, a coating of 36 becomes more hydrophobic when dipped in water or, if dry initially, becomes more hydrophobic if exposed to a humid atmosphere. FIG. 11 shows a procedure devised to demonstrate the new "contraphilic" behavior. FIG. 12 shows the Wilhelmy plate data and, for simplicity, the visually determined wetting behavior using the conventional sessile drop method. In this case, a picture of the drop was taken (on a separate but identical sample) at important points in the procedure to illustrate the unprecedented contraphilic behavior.

Stage 1. With reference to FIGS. 11 and 12, Stage 1 is the first contact of water with the coating. Observation of the shape of the drop with the contact angle less than 90 degrees illustrates that the coating is hydrophilic. This is quantitatively determined (82 deg) from the Wilhelmy plate data and is obtained as shown in FIG. 11 from the first time the coating is immersed in liquid water.

Stage 2. The coating is withdrawn from water. The low receding contact angle ($\theta_{rec}$) that is seen visually as the drop is withdrawn into the syringe can be calculated quantitatively from the Wilhelmy receding force distance curve (about 40 deg).

Stage 3. The coating is re-immersed in water. Remarkably, the advancing contact angle ($\theta_{adv}$) has increased to over 100°. This is easily seen visually in the picture of the drop re-impinging on the same surface already wetted by water in Stage 1. The change in the wetting behavior is quantitatively measured by the Wilhelmy advancing force distance curve (108°). Again, a coating becoming more hydrophilic when simply immersed in ambient temperature water is unprecedented. Furthermore, the change is not just a few degrees but 10's of degrees and is clearly visible.

Stage 4. When the coated slide is immersed further than the original depth, the Wilhelmy plate curve suddenly changes. Suddenly, water is impinging on a surface that has not seen liquid water. The wetting behavior changes back to hydrophilic, as seen in Stage 1. This change is easily observed visually. When the circumference of the drop re-impinging on the surface exceeds the circumference originally wetted, the contact angle of the drop changes from greater than 90 degrees (hydrophobic) to less than 90° (hydrophilic).

If the coating is dried in an oven (60° C.), hydrophilic behavior is once more seen and the contraphilic behavior is reinstated. If the coating is kept at ambient humidity and temperatures, the wetting behavior depends on humidity.

Because the change in wetting behavior is observed by testing the coating in water, the receding contact angle is always the same.

Figure 28:
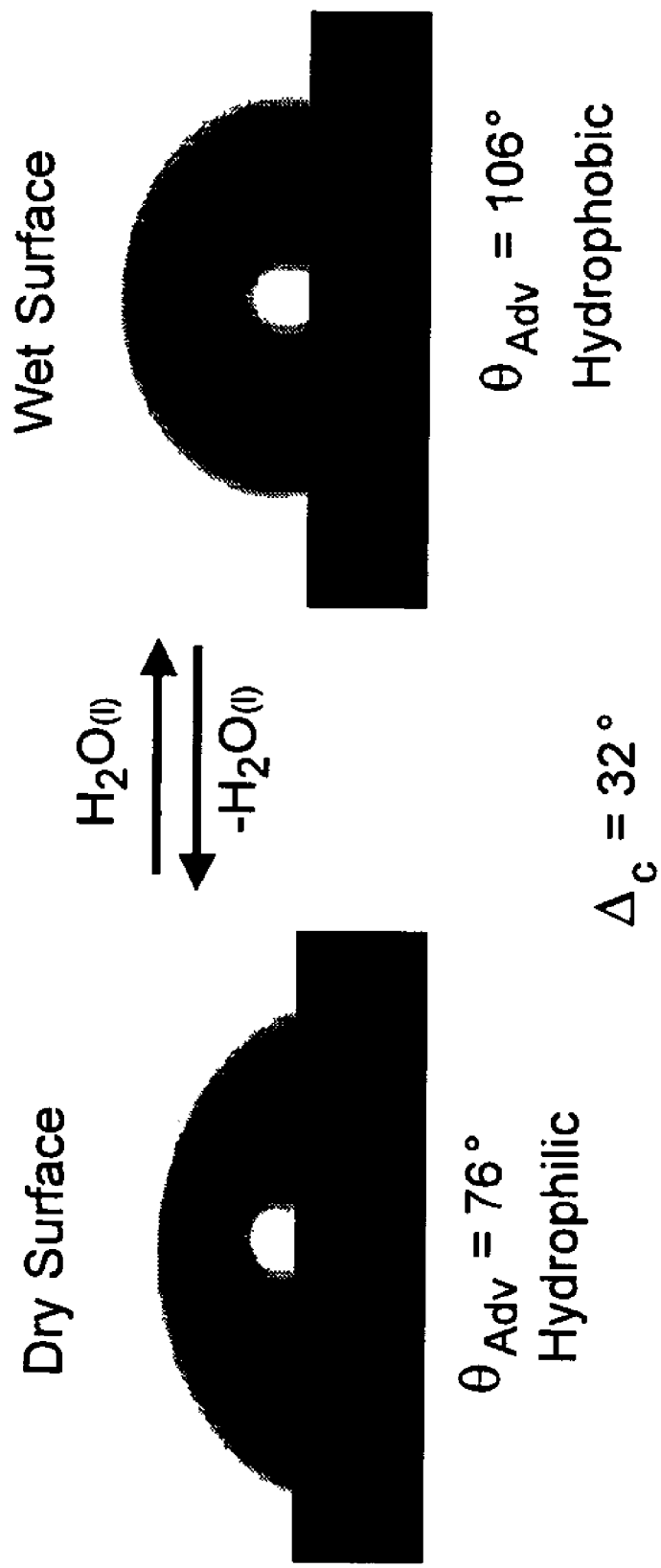
FIG. 28 includes photographs of water contact angles (Rame Hart instrument). Substrate is 98 wt % conventional IPDI-BD/PTMO PU, Hard Block (40 wt %) 2.0 wt % doped with IPDI-BD/P(3FOx:HyOx:BrOx) (1:0:0.65:0.35) PSM.

Contraphilic behavior is a completely new phenomenon. Again, surprisingly, preliminary evidence suggests that certain of the -HyOx-FOx polyurethanes are contraphilic, particularly polyurethanes modified with 2% HyOx-3FOx. FIG. 28 shows clearly the contraphilic behavior of 2.0 wt % (IPDI-BD/P(3FOx:HyOx:BrOx) (1.0:0.65:0.35) SM added to the conventional polyurethane (98 wt %) to the IPDI-BD/PTMO PU, Hard Block (40 wt %).

Example 5

Example 5 is an extension of the "reaction on polymer" approach of Example 4 to create a biocidal surface by means of an SM. In this example, SM 36 is added to a substrate polyurethane (sometimes referred to as a "base" PU), and the surface is exposed to hypochlorite (dilute bleach) as shown in FIG. 7. The resulting coating is biocidal by virtue of the presence of the biocidal SM.

Preparation of Blends and Biocidal Coatings. Polyurethane blends containing 2-wt % dimethylhydantoin (DMH) substituted PU (36) and 98-wt % conventional polyether (PTMO) PU were prepared in tetrahydrofuran (THF). The sample films for anti-bacterial tests were prepared by simply dip-coating glass cover slips (Corning, 24×40×1.2 mm) and distributing the polyurethane evenly over both sides. The samples were placed in an upright position at ambient conditions for 24 hours and in the oven overnight at 60° C. under reduced pressure. The resulting films were transparent with no visible roughness.

Anti-bacterial Tests: For anti-bacterial activity tests a modified version of AATCC 100 method was employed. FIG. 13 schematically shows the testing procedures. The coated cover glass slides were soaked into a solution of free chlorine (50% Clorox® solution containing 3% sodium hypochlorite) for 1 hour. Then they were rinsed with deionized (D.I.) water and placed into vacuum for overnight (60° C., 4 Torr). A known volume of inoculum containing bacteria (e.g., *E. Coli*) at a concentration of about $10^7$-$10^8$ CFU (Colony Forming Units)/ml was used for biocidal test. Slides of base PU (PTMO based PU) were used as control. The initial bacteria inoculum was diluted with saline solution (10 folds). So, this aqueous suspension contains 106-107 CFU/ml of bacteria. 1 microliter of this suspension was placed into surface of the coated glass slide. The slide was then sandwiched with an identical slide. For complete contact the "sandwich" was squeezed and a weight (beaker) was placed on the top. After different contact times (1, 1.5, and, 2 hours) the entire sandwich system was placed into aqueous sodium thiosulfate (10 ml, 0.03 wt %) solution. The resultant solution was then shaken for 5 min. An aliquot of the solution was then serially diluted (3 times) and 100 microliters of each dilution was plated on to a nutrient agar plate. Bacterial colonies on the agar plates were counted after incubation at 37° C. for 24 hours.

A typical test utilizing an *E. coli* challenge is shown in FIG. 14. In particular, the PU control had greater than 400 cfu's while the 98% PU, 2% biocidal SMA had 0 cfu's. All bacteria were killed in thirty minutes with a minimum of 99.9% or 3.6 log reduction.

Figure 15:
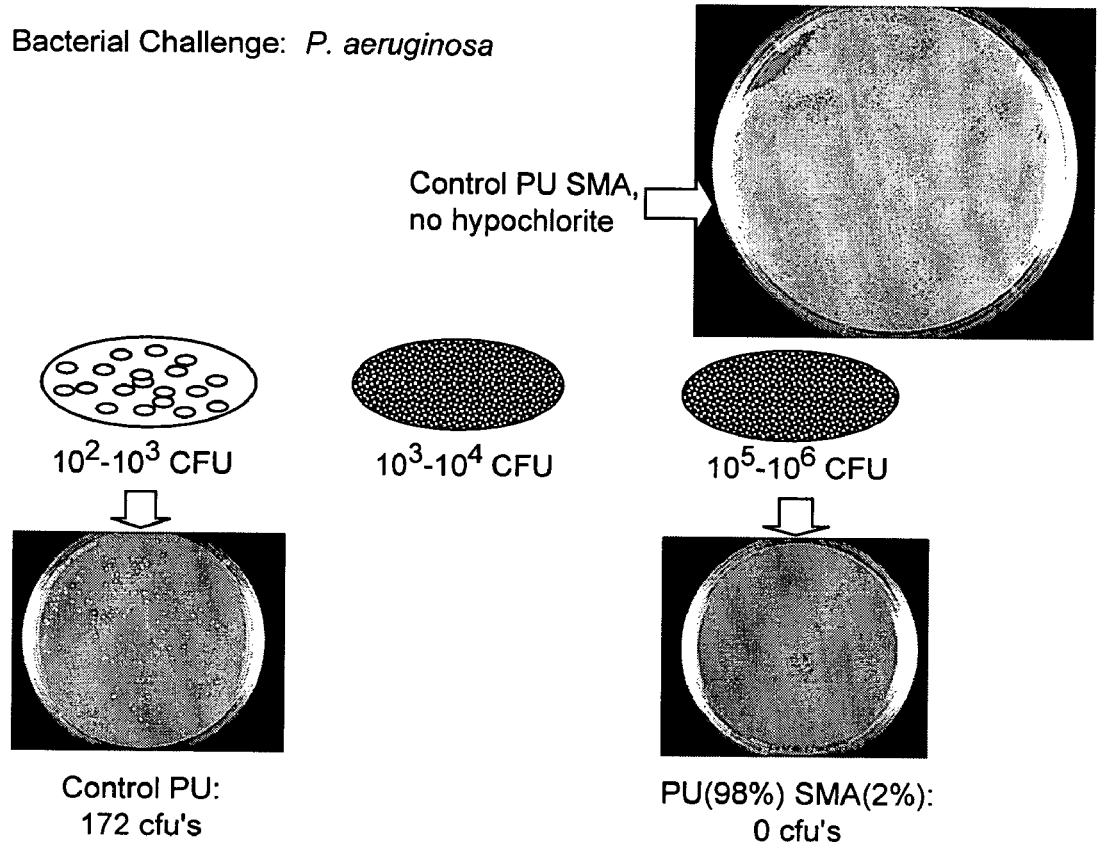
FIG. 15 shows the P. aeruginosa challenge results.

FIG. 15 summarizes a test challenge using a *Pseudomonas aeruginosa*. A modified AATCC-100 "sandwich" test was utilized wherein the bacterial challenge is confined between two coated surfaces as discussed above in connection with FIG. 8. To provide a more challenging challenge than the *E. coli* test, the bacterial stock solution was not diluted and a 10 times higher volume of test solution was used. With a challenge of $10^6$-$10^7$ CFUs for only 15 min, no surviving colony forming units (CFUs) were seen. In particular, the culture dish images of FIG. 10 demonstrate no surviving *P. aeruginosa* CFU's after a 30 min challenge to Gen-1 2% SMA-PU coating. The exponential growth after 24 hr development (upper right) is evident on the control pre-biocide SMA modified PU. In contrast, there are no surviving CFU's after N—Cl formation by bleach activation of the Gen-1 2% SMA-PU coating.

In a similar test, coatings were challenged against *Staphylococcus aureus*. Again, the modified AATCC-100 "sandwich" test was utilized (FIG. 8) wherein the bacterial challenge is confined between two coated surfaces. With a challenge of $10^6$-$10^7$ CFUs for only 30 min, no surviving colony forming units (CFUs) were seen.

While the SM concept was validated with a prebiocidal (Example 4) or biocidal (Example 5) moiety, 5,5-dimethyl-hydantoin, it will be understood by those who are skilled in the art that the functional groups surface-concentrated by the approach described above is broad. For example, the functional groups "F-3" shown in FIG. 5 may be a broad variety of hydantoin-like moieties that optimizes biocidal activity (e.g., those described in U.S. Pat. No. 6,469,177 to Worley which is incorporated by reference). Other moieties that could easily be envisaged include alkylammonium species that are known to have biocidal properties. [Tiller, J. C.; Lee, S. B.; Lewis, K.; Klibanov, A. M., Polymer surfaces derivatized with poly(vinyl-N-hexylpyridinium) kill airborne and waterborne bacteria, Biotechnology and Bioengineering, 2002, 79, 465471.]

Alternatively, F-3 could be a dye molecule that would protect the underlying polymer from UV degradation. F-3 could be a moiety such as —OSi(OR)$_3$ that would convert to siliceous functionalization in the presence of moisture. F-3 could be a bioactive moiety such as a peptide sequence that would favor biocompatibility. In this regard, F-3 could be the RGD peptide sequence that favors endothelialization.

The remarkable and unexpected surface properties of polymers containing soft blocks of the general structure shown in FIG. 2 demonstrates the non-obviousness of compositions employing this molecular architecture. The ability of polymers of the general structure shown in FIG. 2 is not completely understood and we are not bound by theory to explain the observed results. Nevertheless, it appears that the ability of polymers containing soft blocks of the general structure described in FIG. 2 to modify the surface behavior of a "base" polymer, even when present at low weight percent apparently stems from (a) the tendency of soft blocks to concentrate at the surface, (b) the presence of the surface-philic group, (c) the low glass transition temperature of soft block that facilitates (i) chemical modification (as in reaction on polymer shown in Example 4 or even reaction on polymer surface, as shown in Example 5) (ii) rapid surface reorganization that causes a kind of "compliance" to the medium to which the polymer is exposed (seen in high contact angle hysteresis), and facile, reversible interaction with a medium as seen in unprecedented "contraphilic" behavior discussed in Example 3, and (d) as yet little understood phenomena such as (i) described in Example 1, where the polyurethanes containing co-telechelics have higher $\theta_{adv}$ and lower $\theta_{rec}$ than the parent homo-telechelic PUs and (ii) where a new synthetic procedure in Example 2 led to the discovery of amplification of hydrophobicity, which occurred when the cotelechelic had a block structure of fluoro-groups (F1) rather than a random structure of F1 groups.

Referring to FIGS. 5A-5E, the circle represents a cyclic monomer substrate. R is a reagent that will produce a desired function. For example, R3 introduces function F3 into monomer, telechelic, or PSM. X represents reactive functional groups appropriate to synethesizing a particular polymer class. For polyurethanes, the telechelic has two terminal alcohol functions, that is $X^1$=—OH, $X^2$=—OCN (diisocyanate), $X^3$=—OH (diol chain extender). For polyurethane ureas, $X^1$=—OH, $X^2$=—OCN, $X^3$=—NH$_2$— "p" is the mole fraction of the segment containing function F1 (derived from monomer M-F1). For polyurethanes, A and B are polymer forming moieties such as isocyanates and alcohol terminated chain extenders. For polyurea urethanes, A and B are isocyanates and amine terminated chain extenders, respectively. For ester formation, only A could be a dicarboxylic acid and B a diol. Generally, A and B represent polymer forming moieties, one of which will react with a telechelic such as T[F1 F2].

Figure 5A:
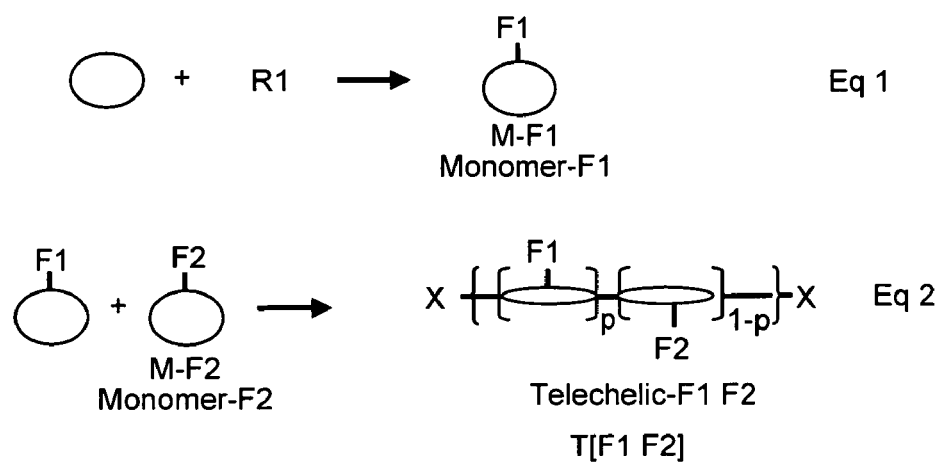
FIG. 5A is a schematic flow diagram showing monomer synthesis.
Figure 5B:
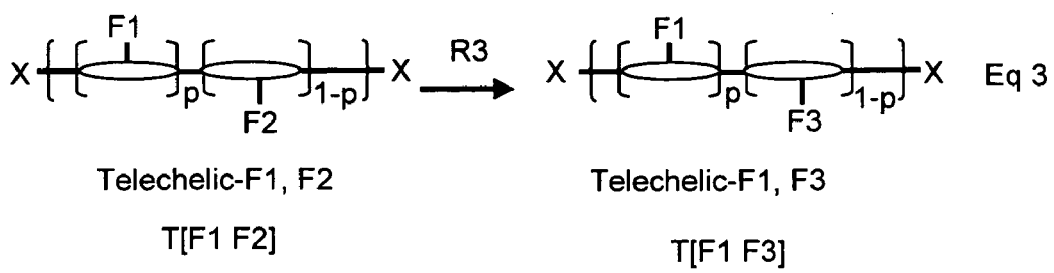
FIG. 5B is a schematic flow diagram showing synthesis of a new telechelic.

Referring to FIGS. 5A-5B, methods may be appreciated for introducing at least two segments so as to generate a functional telechelic for uses such as making a PSM or for use by itself as a detergent or surfactant.

PSM from monomer. Monomers M-F1 and M-F2 are synthesized (FIG. 5A, Eq 1) and copolymerized to generate functional telechelic T[F1 F2] (FIG. 5A, Eq 2). Subsequently, T[F1 F2] is used to generate polyurethane PSM AB-T[F1 F2] as shown in FIG. 2B, Equation 3. Here, the combination of properties of segmers F1 and F2 in the soft block gives a desirable PSM. The ratio of F1 and F2 are controlled by the M-F1 and M-F2 feed in generating T[F1 F2]. This ratio may be varied to optimize the activity of the PSM and to control physical properties such as the glass transition temperature of the soft block. The method of FIG. 5A and/or the method of FIG. 5B may be used to prepare new 3,3-substituted 1,3-propylene oxide telechelics.

Modification of a telechelic. It may not always be possible to prepare a monomer that will be adaptable to the polymerization reaction of choice. By the reaction of a reagent R3 with telechelic T[F1 F2] a new telechelic T[F1 F3] is generated by reagent R3. Complete change of F2 to F3 is shown in FIG. 5B, Eq 3. Partial change of F2 to F3 may be adequate depending on the application.

Figure 5E:
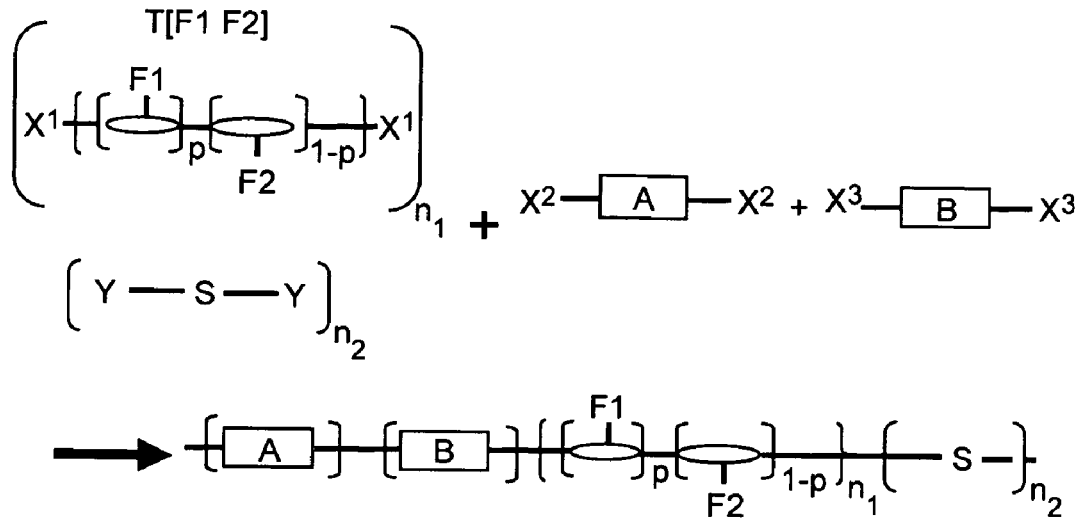
FIG. 5E is a schematic flow diagram showing the simultaneous incorporation of respective soft blocks into a polyurethane. Surface modification of a polyurethane may be accomplished by the "mixed soft block" method shown in FIG. 5E. The method of FIG. 5E provides a new material, a modified PU.

Referring to FIGS. 5C-5E, methods may be appreciated for introducing a functional telechelic so as to generate a polyurethane PSM.

Incorporation by conventional polyurethane chemistry. FIG. 5C shows the reaction of telechelics T[F1 F2], T[F1 F3] (or, if desired, telechelics with multiple segmers F1, F2, F3, etc.) with isocyanates and chain extenders, that is, by well known polyurethane chemistry, to generate polyurethane PSMs.

Modification of an existing PSM. An existing PSM may be modified according to the scheme shown in FIG. 5D. Here, a desired functionality F-3 is introduced by reaction of a PSM with R3 to give a new PSM polymer AB-T[F1 F2 F3]. If the reaction with R3 is complete, q (FIG. 5D, Eq. 5) is zero. If the reaction with R3 is incomplete, q (FIG. 5C, Eq. 4) is finite and the soft block of the PU PSM contains three functional repeat units F-1, F-2, and F-3.

Mixed soft blocks. In a preferred embodiment, the above method is varied by the use of a modified such as T[F 1 F2] along with standard telechelics such as polyethers, polyesters, and polycarbonates (FIG. 5E). Such a method may be used in a manufacturing environment wherein a small amount of T[F1 F2] could be included in the feed, for example in a twin screw extruder. The product is a "mixed soft block" polyurethane (or polyester, nylon, or other polymer incorporating alcohol functionalized telechelic) where the surface active soft block T[F1 F2] concentrates at the surface. Typical "S" soft blocks in polyurethane chemistry are derived from polyalcohols such as dihydroxy polyethyleneglycol, dihydroxy polytetramethylene oxide, hydroxyl terminated polyisobutylenes, and hydroxyl terminated polyesters.

Example 6

New Monomers

Example 6A

New Monomer Hy4Ox

A 5,5-hydantoin containing monomer 1 (Hy4Ox) was synthesized according to the scheme in FIG. 17. This 5,5-hydantoin containing monomer 1 was used to make telechelics, which were in turn used to prepare pre-biocidal PSMs.

Preparation of 2-((3-methyloxetan-3-yl)methoxy)ethanol (HE1Ox, 5). Ethylene glycol (26.25 g, 0.42 mol) and KOH (19.45 g, 0.35 mol) were added to a round-bottom flask equipped with a magnetic stirrer and a reflux condenser. When all KOH had dissolved the 3-bromomethyl-3-methyloxetane (4) (46.30 g, 0.28 mol) was added. The system was heated to 70° C. for 3 hours. The reaction material was then distilled under vacuum (10 Torr) and collected as a single fraction. The distilled material was then extracted with diethyl ether and water. The water fraction was then extracted with CHCl$_3$ multiple times to obtain 11.98 g (29.2% yield) of the final product, though analysis of the water phase indicated a significant amount of HE1Ox was unextracted. H$^1$ NMR (CDCl$_3$): δ 1.31 ppm (—CH$_3$, 3H, s), δ 2.63 ppm (—OH, 1H, t), δ 3.54 ppm (—CH$_2$—, 2H, s), δ 3.60 ppm (—OCH$_2$—, 2H, t), δ 3.76 ppm (HOCH$_2$—, 2H, q), δ 4.38 ppm (oxetane CH$_2$, 2H, d), δ 4.55 ppm (oxetane CH$_2$, 2H, d).

Preparation of 2-((3-methyloxetan-3-yl)methoxy)ethyl 4-methylbenzenesulfonate (TE1Ox, 6). HE1Ox (15.20 g, 0.10 mol) and pyridine (17.93 g, 0.23 mol) were added to a round-bottom flask equipped with a magnetic stirrer and a drying tube and placed in an ice bath. Once chilled, p-toluenesulfonyl chloride (23.53 g, 0.12 mol) was added to the flask and the ice bath was maintained for 30 minutes. The ice bath was then removed and the system was vigorously mixed for another 3.5 hours. The flask was then returned to the ice bath and 1.0 M HCl (35 mL) was added to the flask. The product was then extracted with CHCl$_3$ and vacuum dried. A colorless liquid (26.44 g, 84.6% yield) was obtained. H$^1$ NMR (CDCl$_3$): δ 1.24 ppm (—CH$_3$, 3H, s), δ 2.45 ppm (—CH$_3$, 3H, s), δ 3.46 ppm (—CH$_2$—, 2H, s), δ 3.68 ppm (—OCH$_2$—, 2H, t), δ 4.18 ppm (—CH$_2$OTs, 2H, t), δ 4.30 ppm (oxetane CH$_2$, 2H, d), δ 4.42 ppm (oxetane CH$_2$, 2H, d), δ 7.35 ppm (aromatic CH, 2H, d), δ 7.80 ppm (aromatic CH, 2H, d).

Preparation of 5,5-dimethyl-3-(2-((3-methyloxetan-3-yl)methoxy)ethyl)-imidazolidine-2,4-dione (Hy4Ox, 1). Ethanol (7.9 mL), KOH (2.27 g, 0.040 mol), and 5,5-dimethylhydantoin (5.60 g, 0.044 mol) were added to a flask equipped with a magnetic stir bar and reflux condenser. When dissolved, TE1Ox (9.99 g, 0.033 mol) in ethanol (8.8 mL) was added and the mixture was heated to reflux with a heating mantle. After heating overnight (~15 h), the reaction mixture was allowed to cool to room temperature. The ethanol was mostly removed by rotary evaporation and then extracted with CHCl$_3$. Vacuum drying yielded 8.52 g (100% yield) of a pale yellow, viscous oil. H$^1$-NMR (CDCl$_3$): δ 1.28 ppm (—CH$_3$, 3H, s), δ 1.41 ppm (—CH$_3$, 6H, s), δ 3.50 ppm (—OCH$_2$—, 2H, s), δ 3.70 ppm (—NCH$_2$CH$_2$O—, 4H, m), δ 4.30 ppm (oxetane CH$_2$, 2H, d), δ 4.48 ppm (oxetane CH$_2$, 2H, d), δ 6.71 ppm (amide NH, 1H, s).

Example 6B

New Monomer, MOx

The new monomer 2 (MOx) was synthesized according to the following scheme:

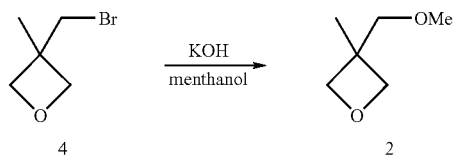

Preparation of 3-methoxymethyl-3-methyloxetane (MOx, 2)

KOH (52.30 g, 0.93 mol) was added to methanol (113 mL) in a 250 mL flask. When the KOH had dissolved, the flask was placed in an ice bath and 3-bromomethyl-3-methyloxetane (118.51 g, 0.72 mol) was slowly added dropwise. When the addition was complete, the ice bath was maintained until the exotherm subsided. Then the ice bath was replaced with a heating mantle and the mixture was heated to reflux (65° C.) for 30 min. The KBr precipitate was filtered, methanol was removed under vacuum, and the product was distilled at 37° C. and 10 torr. A colorless liquid (65.08 g, 78.1% yield) was obtained. H$^1$ NMR (CDCl$_3$): δ 1.29 ppm (—CH$_3$, 3H, s), δ

3.38 ppm (—OCH$_3$, 3H, s), δ 3.42 ppm (—CH$_2$O—, 2H, s), δ 4.33 ppm (oxetane CH$_2$, 2H, d), δ 4.48 ppm (oxetane CH$_2$, 2H, d).

Example 6C

New Monomer, Alkylammonium Tosylate, N611E1Ox

A new monomer: alkylammonium tosylate, N611E1Ox, 7, was synthesized according to the following scheme:

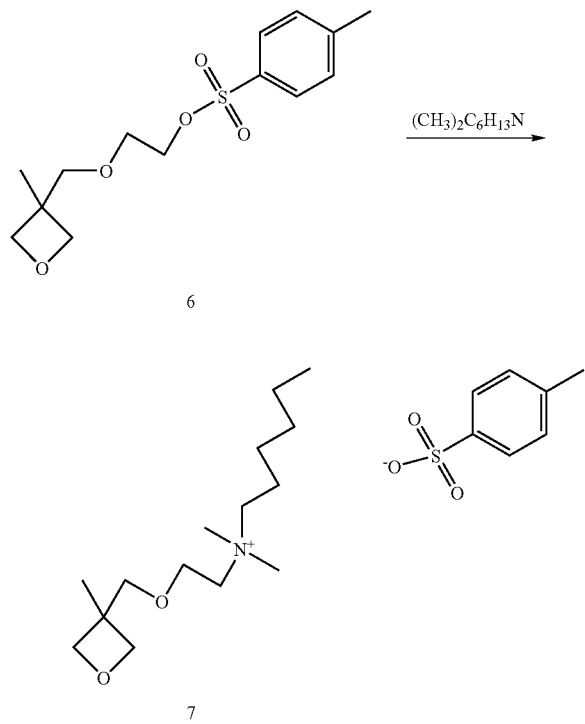

2-((3-methyloxetan-3-yl)methoxy)ethyl 4-methylbenzenesulfonate (6) was synthesized according to Grunzinger, 2005. 6 was quaternized by adding N,N-dimethylhexan-1-amine (0.57 g, 4.4 mmol) to 6 (1.32 g, 4.4 mmol) in 5 mL anhydrous toluene and letting them react at 80° C. for 18 hours under nitrogen purge. The mixture was cooled down to room temperature. The solvent was evaporated with Bucher rotavap. The white solid product was washed with ether 3 times and dried under vacuum for 24 hours. The final product was white solid. H$^1$ NMR (CDCl$_3$): δ 0.96 ppm (—CH$_3$, 3H, s), 1.24 ppm (—CH$_3$, 3H, s), 1.35 (—CH$_2$—, 6H, broad), 1.80 ppm (—CH$_2$—, 2H, m), 2.35 ppm (—CH$_3$, 3H, s), 3.35 ppm (—N$^+$(CH$_3$)$_2$ 6H, s) 3.46 ppm (—CH$_2$—N$^+$—CH$_2$—, 4H, s), 3.50 ppm (—OCH$_2$—, 2H, s) 3.68 ppm (—OCH$_2$—, 2H, t), 4.30 ppm (oxetane CH$_2$, 2H, d), 4.42 ppm (oxetane CH$_2$, 2H, d), 7.35 ppm (aromatic CH, 2H, d), 7.80 ppm (aromatic CH, 2H, d).

Example 7

New 3,3,-Substituted 1,3-propylene Oxide Telechelics

Example 7A1

Hydantoin Containing Telechelics

Telechelic P(Hy4Ox:MOx-16:84) was prepared by the general method shown in FIG. 5A. A solution of Hy4Ox (2.73 g, 10.7 mmol) and MOx (4.32 g, 37.2 mmol) was prepared in methylene chloride (9.41 g) and dried over 4 Å molecular sieves. A 100 mL three-necked, round-bottom flask equipped with a 50 mL addition funnel and sealed with rubber septa was charged with BD (0.4163 g, 4.62 mmol) and methylene chloride (0.74 g). The monomer solution was transferred to the addition funnel and the system was purged with N$_2$ for 30 min at room temperature then placed in an ethylene glycol/water (50/50 v/v) bath at −5° C. Once the flask was chilled, BF$_3$ etherate (2.07 g, 14.6 mmol, 48 wt % BF$_3$) was added and the system was allowed to stand for 30 min. The contents for the addition funnel were then added slowly over a period of one hour. The bath temperature was maintained for an additional four hours then allowed to warm to room temperature. Water (5 mL) was added to quench the reaction. The reaction mixture was extracted with water and chloroform. The solvent was removed yielding the telechelic P(Hy4Ox:MOx-16:84), H-3, Table 8, as a viscous oil. Telechelics of other Hy4Ox:MOx ratios (H-2, H-4, H-5, Table 8) were prepared in the same manner. A control telechelic, P(MOx), H-1 was also prepared similarly using only monomer 2. (In Table 8, error for telechelic content of Hy4Ox is ±6%.

TABLE 8

Calculated values for Hy4Ox incorporation in the telechelic, number-average molecular weight, and T$_g$ of the telechelics.

|  | Ref | Hy4Ox$^a$ (mol %) | M$_n$ (g/mol) | T$_g$ (° C.) Onset | T$_g$ (° C.) Inflection | T$_g$ (° C.) End |
|---|---|---|---|---|---|---|
| P(MOx) | H-1 | 0 | 1.36 × 10$^3$ | −52.5 | −49.8 | −47.5 |
| P(Hy4Ox:MOx-8:92) | H-2 | 0.083 | 1.95 × 10$^3$ | −39.3 | −35.4 | −32.2 |
| P(Hy4Ox:MOx-16:84) | H-3 | 0.163 | 2.03 × 10$^3$ | −46.2 | −42.2 | −35.6 |
| P(Hy4Ox:MOx-39:61) | H-4 | 0.386 | 2.68 × 10$^3$ | −9.0 | −4.5 | 4.7 |
| P(Hy4Ox) | H-5 | 1 | 2.51 × 10$^3$ | 7.0 | 17.7 | 29.7 |

Example 7A2

Alkylammonium Telechelic

An alkylammonium telechelic was prepared by the method of FIG. 5A.

Polymerization of N611E1Ox (7) to telechelic P(N611E1Ox): Under nitrogen purge, 154 mmol), 1,4-Butanediol (0.01 g, 0.10 mmol) and BF$_3$—OEt$_2$ (0.03 g, 0.20 mmol) were reacted in 2 mL anhydrous CH$_2$Cl$_2$ at ambient temperature for 45 minutes. Reaction mixture was cooled down to 0° C. Through an additional funnel, N611E1Ox (6) dissolved in 7 ml CH$_2$Cl$_2$ was added drop wise to the solution. The mixture was reacted for 15 hours. Then, it was warmed up to ambient temperature and quenched with 10 ml H$_2$O. The organic part was washed with water (20 mL×3) and solvent was evaporated under vacuum at 60° C. Calculation using end group analysis method with trifluoroacetic anhydride showed molecular weight of the resulting product, P(N611E1Ox), to be 2400 g/mole. Thermal analysis with MDSC gave the value of −24° C. for $T_g$ of P(N611E1Ox).

The structure for telechelic P(N611E1Ox) is as follows:

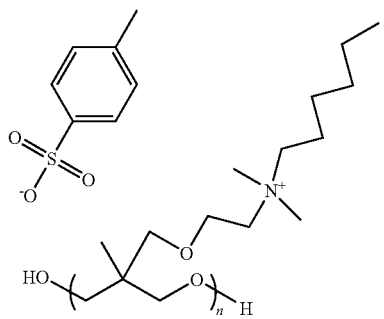

Example 7B

Alkylammonium telechelics were prepared by the method of FIG. 5B. 3FOx containing telechelics were prepared.

(i) Preparation of the BBOx-3FOX Telechelic 10 where m=0.2.

BBOx oxetane monomer was prepared according to Kawakami, Y., Takahashi, K., Hibino, H, Macromolecules 1991, 24, 4531-4537. 3FOx:alkylammonium butoxymethyl telechelic 11 was prepared from precursor bromobutoxy-trifluoroethoxy telechelic 10 according to the reaction:

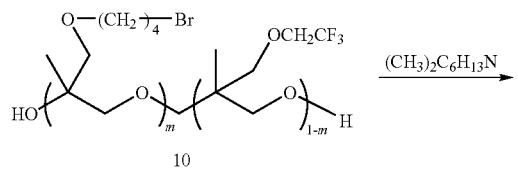

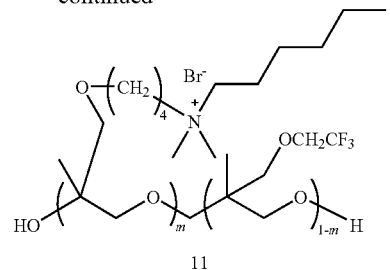

To a 50 mL addition funnel were added 3Fox (14.95 g, 81 mmol), BBOx (6.4 g, 27 mmol), 1,4-butanediol (90 µL, 1 mmol) and 20 mL anhydrous CH$_2$Cl$_2$. This mixture solution was added drop wise to a two-necked 100 ml flask with 0.25 mL BF$_3$.OEt$_2$ in 25 mL anhydrous CH$_2$Cl$_2$ at 0° C. within 3 hour. The reaction system was stirred and maintained at 0° C. for another 15 hours. 5 mL H$_2$O was added in and stirred at room temperature for 0.5 hour to stop the reaction. The CH$_2$Cl$_2$ solution was washed by H$_2$O (40 mL×3) and the solvent was evaporated and the residue was dried at 80° C. under vacuum for 48 hours to afford 19.54 g copolymer. $^1$HNMR (CDCl$_3$): δ 0.91 ppm (—CH$_3$, 3H, s), 1.68 ppm (—CH$_2$— for BBOx, 2H), 1.92 ppm (—CH$_2$— for BBOx, 2H), 3.19 ppm (backbone —CH$_2$—, 4H, m), 3.4 ppm (—CH$_2$Br—, 2H), 3.45 ppm (—OCH$_2$—, 2H, s), 3.75 ppm (—CH$_2$CF$_3$—, 2H, m). $M_n$ by end group analysis using trifluoroacetic anhydride was 13,000 g/mole.

(ii) Preparation of the Alkyl Ammonium Functionalized Telechelic 11.

Telechelic 10 (4.4 g) and N,N-dimethylhexylamine (1.5 mL, 8.8 mmol) were dissolved in 20 mL acetonitrile. The mixture was heated to reflux and stirred for 15 hours under nitrogen. The solvent and excess N,N-dimethylhexylamine was evaporated under vacuum to give a sticky liquid product. δ0.91 ppm (—CH$_3$, 3H, s), 1.35 ppm (—CH$_2$—, 6H, broad), 1.68~1.92 ppm (—CH$_2$—, 2H, m), 3.19 ppm (backbone —CH$_2$—, 4H, m), 3.4 ppm (—CH$_2$N—, 2H, CH$_3$—N—CH$_3$, 6H), 3.45 ppm (—OCH$_2$—, 2H, s), 3.75 ppm (—CH$_2$CF$_3$—, 2H, m). By $^1$H NMR, the bromomethyl group was converted to the alkylammonium bromide, quantitatively. Telechelic 11 was water-soluble.

(iii) Preparation of the BBOx-3FOx Telechelic 12 with m=0.125.

Under nitrogen purge, 1,4-Butanediol (0.45 g, 5 mmol) and BF$_3$—OEt$_2$ (1.42, 10 mmol) were reacted in 20 mL anhydrous CH$_2$Cl$_2$ at ambient temperature for 45 minutes. Reaction mixture was cooled down to 0° C. Through an additional funnel, a mixture of 3FOx (16.56 g, 90 mmol) and BBOx (2.37 g, 10 mmole) dissolved in 20 ml CH$_2$Cl$_2$ was added drop wise to the solution. The mixture was reacted for 15 hours. It was warmed up to ambient temperature and quenched with 40 ml H$_2$O. The organic part was washed first with 30 mL 3% wt HCl solution, then with 30 mL 3% wt NaCL solution. The solution was precipitated in 400 mL water. Solvent was evaporated under vacuum at 60° C. $^1$HNMR spectra showed that m=0.125. $^1$HNMR (CDCl$_3$): δ 0.91 ppm (—CH$_3$, 3H, s), 1.68 ppm (—CH$_2$— for BBOx, 2H), 1.92 ppm (—CH$_2$— for BBOx, 2H), 3.19 ppm (backbone —CH$_2$—, 4H, m), 3.4 ppm (—CH$_2$Br—, 2H), 3.45 ppm (—OCH$_2$—, 2H, s), 3.75 ppm (—CH$_2$CF$_3$—, 2H, m). $M_n$ by end group analysis using trifluoroacetic anhydride was 8400 g/mole.

Figure 18:
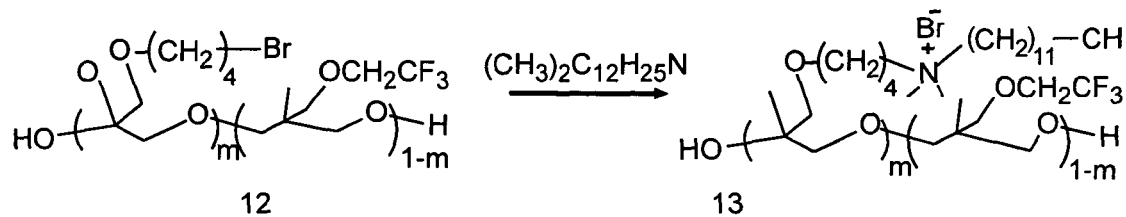
FIG. 18 shows preparation of ME2Ox:hexylammonium butoxymethyl telechelic from precursor bromobutoxy-ME2Ox telechelic.

FIG. 18 shows preparation of ME2Ox:hexylammonium butoxymethyl telechelic 13 from precursor bromobutoxy-ME2Ox telechelic 12.

(iv) Preparation of the Dodecyl Ammonium Functionalized Telechelic 13 with m=0.125.

Telechelic 12 (3.38 g) and N,N-dimethyldodecylamine(1.5 mL, 8.8 mmol) were dissolved in 20 mL acetonitrile. The mixture was heated to reflux and stirred for 15 hours under nitrogen. The solvent and excess N,N-dimethylhexylamine was evaporated under vacuum. δ 0.91 ppm (—$CH_3$, 3H, s), 1.35 ppm ($CH_2$—, 18H, broad), 1.68~1.92 ppm (—$CH_2$, 6H, broad), 3.19 ppm (backbone —$CH_2$—, 4H, m), 3.4 ppm (—$CH_2N$—, 2H, $CH_3$—N—$CH_3$, 6H), 3.45 ppm (—$OCH_2$—, 2H, s), 3.75 ppm (—$CH_2CF_3$—, 2H, m). By $^1$H NMR, the bromomethyl group was converted to the alkylammonium bromide, quantitatively. Mn value obtained from $^1$H-NMR was 8,700 g/mole.

ME2Ox containing telechelics were prepared.

Figure 19:
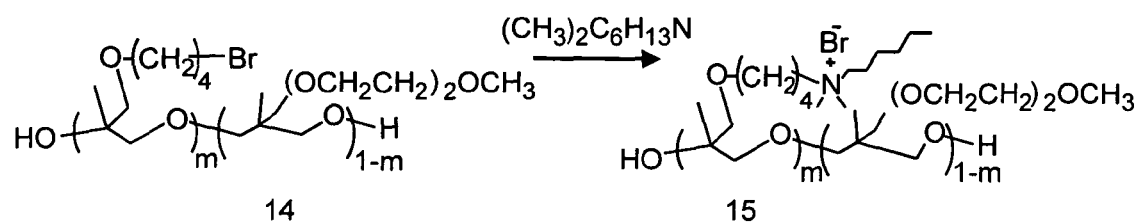
FIG. 19 shows preparation of ME2Ox:hexylammonium butoxymethyl telechelic from precursor bromobutoxy-ME2Ox telechelic.

FIG. 19 shows preparation of ME2Ox:hexylammonium butoxymethyl telechelic 15 from precursor bromobutoxy-ME2Ox telechelic 14.

(i) Preparation of the BBOx-ME2Ox Telechelic 14 with m=0.25.

BBOx oxetane monomer was prepared according to Y. Kawakami, et al., supra. ME2Ox oxetane was synthesized as follows: A mixture of 2-(2-methoxyethoxy)ethanol (20 g, 0.17 mol) and NaH (4 g, 0.17 mol) in 50 mL anhydrous tetrahydrofuran (THF) was stirred vigorously at room temperature until no more $H_2$ released from the system. The system was cooled to 0° C. by ice-water bath and 3-bromomethyl-3-methyloxetane (BrOx) (27 g, 0.17 mol) was added drop wisely within 2 hours. The reaction mixture was brought to room temperature and stirred over night. After filtration 100 mL $H_2O$ was added and the product was extracted by $CH_2Cl_2$ and distilled with $CaH_2$. $^1$HNMR ($CDCl_3$): δ 1.32 ppm (—$CH_3$, 3H, s), 3.39 ppm (—$OCH_3$, 3H, s), 3.55 ppm (—$OCH_2CH_2O$—, 4H, m), 3.67 ppm (—$OCH_2CH_2O$—, 4H, m, and —$CH_2$—, 2H, m), 4.35 ppm (ring —$CH_2$—, 2H, d), 4.52 ppm (ring $CH_2$, 2H, d).

Through an additional funnel a mixture of BBOx (4.23 g, 18 mmol), ME2Ox (12.0 g, 154 mmol), 1,4-Butanediol (59 μL, 0.66 mmol) and 50 mL anhydrous $CH_2Cl_2$ was added to the two-necked 100 ml flask containing $BF_3$—$OEt_2$ and 25 mL anhydrous $CH_2Cl_2$ under nitrogen purge within 3 hours. The reaction system was stirred for 15 hours at 0° C. The reaction was quenched with addition and stirring of $H_2O$ for 0.5 hour. Organic solution was washed by water (40 mL×3). The solvent was evaporated and the residue was dried at 80° C. under vacuum for 48 hours to obtain 15.77 g copolymer. $^1$HNMR ($CDCl_3$): δ 0.91 ppm (—$CH_3$, 3H, s), 1.68 ppm (—$CH_2$— for BBOx, 2H), 1.92 ppm (—$CH_2$— for BBOx, 2H), 3.19 ppm (backbone —$CH_2$—, 4H, m), 63.30 ppm (—$CH_2$, 2H, s), 3.38 ppm (—$OCH_3$ 3H, s), 3.4 ppm (—$CH_2Br$—, 2H), 3.55 ppm (—$OCH_2CH_2O$—, 4H, m), 3.64 ppm (—$OCH_2CH_2O$—, 4H, m).

(ii) Preparation of the Hexyl Ammonium Functionalized Telechelic 15 with m=0.25.

Telechelic 14 (10.8 g) and N,N-dimethylhexylamine (2.02 mL, 11.9 mmol) were dissolved in 20 mL acetonitrile. The mixture was heated to reflux and stirred for 15 hours under nitrogen. The solvent and excess N,N-dimethylhexylamine was evaporated under vacuum to give a sticky liquid product. δ 0.91 ppm (—$CH_3$, 3H, s), 1.35 (—$CH_2$—, 6H, broad), 1.68~1.92 ppm (—$CH_2$—, 6H, broad), 3.19 ppm (backbone —$CH_2$—, 4H, m), 3.30 ppm (—$CH_2$, 2H, s), 3.38 ppm (—$OCH_3$ 3H, s), 3.4 ppm (—$CH_2N$—, 2H, $CH_3$—N—$CH_3$, 6H), 3.55 ppm (—$OCH_2CH_2O$—, 4H, m), 3.64 ppm (—$OCH_2CH_2O$—, 4H, m). By $^1$H NMR, the bromomethyl group was converted to the alkylammonium bromide, quantitatively. Telechelic 15 is water-soluble.

(iii) Preparation of the Dodecyl Ammonium Functionalized Telechelic 16 with m=0.25.

Figures 20, 21:
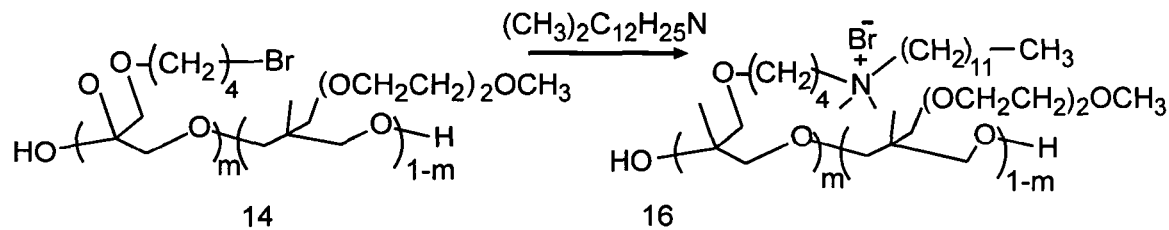
FIG. 20 shows preparation of ME2Ox:dodecyl ammonium butoxymethyl telechelic from precursor bromobutoxy-ME2Ox telechelic.
FIG. 21 is a table of calculations of number average molecular weight by $^1$HNMR and glass transition temperatures of telechelics obtained by modulated DSC.

FIG. 20 shows preparation of ME2Ox:dodecyl ammonium butoxymethyl telechelic 16 from precursor bromobutoxy-ME2Ox telechelic 14.

Telechelic 14 (6.24 g) was dissolved in 5 mL acetonitrile. The solution was heated to reflux. N,N-dimethyldodecylamine (6.15 g, 28.9 mmol) was added slowly to the mixture, and was stirred for 15 hours under nitrogen. The solvent and excess N,N-dimethyl dodecylamine was evaporated under vacuum to give a sticky liquid product. δ 0.91 ppm (—$CH_3$, 3H, s), 1.35 (—$CH_2$—, 8H, broad), 1.68~1.92 ppm (—$CH_2$—, 18H, broad), 3.19 ppm (backbone —$CH_2$—, 6H, m), 3.30 ppm (—$CH_2$, 2H, s), 3.38 ppm (—$OCH_3$ 3H, s), 3.4 ppm (—$CH_2N$—, 2H, $CH_3$—N—$CH_3$, 6H), 3.55 ppm (—$OCH_2CH_2O$—, 4H, m), 3.64 ppm (—$OCH_2CH_2O$—, 4H, m). By $^1$H NMR, the bromomethyl group was converted to the alkyl ammonium bromide, quantitatively.

Example 8

New polyurethane polymeric surface modifying additives were prepared, as more particularly set forth in the following Examples 8A etc.

Example 8A

Hydantoin-Containing PSMs

To a 100 mL round-bottom flask was added H-2, P(Hy4Ox:MOx-16:84) (0.96 g, 0.47 mmol), BD (0.14 g, 1.5 mmol), dibutyltin dilaurate (3 drops, 10 wt % in THF), dimethylformamide (0.74 mL). An addition funnel was attached and HMDI (0.61 g, 2.3 mmol) and DMF (2.45 mL) were added. The system was heated to 70° C. and purged with $N_2$ for 20 min. The contents of the addition funnel were added rapidly. The extent of reaction was determined by removing small aliquots and observing the decrease of the 2268 $cm^{-1}$ isocyanate peak in the FT-IR spectrum. 1,4-Butanediol in DMF was added to the reaction mixture until the isocyanate was consumed (32.8 mg, 0.36 mmol BD and 2 mL DMF). The product (PU-C) was precipitated in $H_2O$, dried, dissolved in THF, and reprecipitated in $H_2O$. Polyurethanes using other P(Hy4Ox:MOx) telechelics (Table 8, supra) were prepared in a similar manner. The compositions and physical properties are set forth in FIG. 21. FIG. 22 shows characterization data for HMDI-BD (wt %)/P(Hy4Ox:MOx) polyurethanes.

Example 8B

Hydantoin-Containing Polyurethane PSMs: Contraphilic Materials Prepared via Substitution on Polymer) (FIG. 5E)

A group of contraphilic polyurethanes (PU s) were prepared with different soft block compositions.

The interesting discovery has been made that soft blocks with higher ratios of fluorinated segments to hydantoin segments are (initially, when dry) more hydrophilic compared to ones with lower ratios of semifluorinated to hydantoin segments.

Materials. 3-(2,2,2-Trifluoroethoxymethyl)-3-methyloxetane (3FOx), 3-(2,2,3,3,3-pentafluoropropoxymethyl)-3-methyloxetane (5FOx), and 3-bromomethyl-3-methyloxetane (BrOx) were synthesized following published procedures [Malik, 2000 #278] (polymer paper) or were provided by Gencorp Aerojet (Sacramento, Calif.) or OMNOVA Solutions (Akron, Ohio). Monomers were distilled under vacuum before use: 3FOx and 5FOx close to 100° C./5 mmHg; BrOx at 85° C./5 mmHg. Boron trifluoride dietherate ($BF_3O(C_2H_5)_2$), was used as received. 5,5-Dimethylhydantoin (Aldrich, 97%), potassium carbonate, $K_2CO_3$, (Acros Chemicals, ACS), and sodium thiosulfate, $Na_2S_2O_3$, (99%) were used as received. Methylene chloride (anhydrous), tetrahydrofuran (THF, ACS), dimethylformamide (DMF, anhydrous), and methanol (ACS) were either used as received or dried and stored over 4 Å molecular sieves. Isophorone diisocyanate (IPDI, 98%), poly(tetramethylene oxide) (PTMO-2000) and dibutyltin dilaurate catalyst (T-12) were obtained from Aldrich. 1,4-Butanediol (BD) was purchased from Acros Chemicals.

Synthesis. The synthesis and characterization of the P(FOx:BrOx) telechelics and IPDI-BD/P(FOx:BrOx) polyurethanes have been reported in detail. [Makal, 2005 #1543] IPDI-BD/P(FOx:BrOx) polyurethanes were typically purified by reprecipitation (THF solutions into deionized water/methanol). Without adequate purification, coatings can contaminate the water surface thereby changing the surface tension (and contact angle). Such contamination is difficult to detect by sessile drop methods. [Uilk, 2003 #639]

$^1$H NMR for a representative precursor PU, IPDI-BD/P(FOx:BrOx-1:1) is given in FIG. 17A. The spectrum was taken in CDCl$_3$. The 1:1 composition is confirmed by the ratio of "a" (1.07 ppm, $CH_3$, BrOx) to "b" (0.88 ppm, $CH_3$, 3FOx). Other peaks (ppm vs. TMS) with assignments according to the structure in FIG. 17A: 0.8-0.9 ppm (m, n, $CH_3$, IPDI); 1.7 ppm (h, —$OCH_2CH_2CH_2CH_2O$—); 3.1-3.3 ppm (f, $CH_2$ methylenes for the three segmers); 3.45 ppm (e, $CH_2$—Br); 3.48 ppm (d, —$OCH_2CF_3$); 3.7-3.8 ppm (c, —$CH_2$—O—$CH_2CF_3$); 4.0-4.1 ppm (g, —$OCH_2CH_2CH_2CH_2O$—).

5,5-Dimethylhydantoin substitution on precursor PU was carried out in DMF in the presence of $K_2CO_3$. In a typical procedure, 5.32 g (38.50 mmol) $K_2CO_3$ was dispersed in 12.80 g DMF with 0.98 g (7.65 mmol) 5,5-dimethylhydantoin in a 100 ml flask. 5,5-dimethylhydantoin was soluble in DMF. The mixture was heated to 65° C. under nitrogen purge with condenser. Precursor PU solution containing 4.12 g (0.61 mmol soft block) precursor PU in 9.25 g DMF was dripped into the flask and the temperature was increased and kept at 90-95° C. range. After 72 h, the reaction was quenched by decreasing the temperature to ambient. The product was precipitated into deionized water, filtered, and dried at 60° C. under vacuum.

The structure of the 5,5-dimethylhydantoin substituted PUs and degree of 5,5-dimethylhydantoin substitution is verified by $^1$H NMR. $^1$H NMR spectrum of a representative hydantoin-substituted PU, IPDI-BD(40)/P(3FOx:HyOx:BrOx-1.0:0.65:0.35), is shown in FIG. 17B. The spectrum was taken in DMSO, d$_6$. The ratio of the peak "h" (1.23 ppm ($CH_3)_2$, 5,5-dimethylhydantoin) to "b" (0.8-0.9 ppm, $CH_3$, 3FOx) was used to determine extent of hydantoin substitution. Other peaks (ppm vs. TMS) with assignments according to the structure in FIG. 17B: 0.7-0.8 ppm (c, $CH_3$, 5,5-dimethylhydantoin containing segmer); 0.9-1.0 ppm (a, m, n, $CH_3$, BrOx; $CH_3$, IPDI); 1.55 ppm (1, $OCH_2CH_2CH_2CH_2O$—); 3.0-3.4 ppm (d, f, g, j, methylenes for the three segmers); 3.46 ppm (e, —$OCH_2CF_3$); 3.9-4.0 ppm (k, —$OCH_2CH_2CH_2CH_2O$—); 8.2 ppm (p, CONH, 5,5-dimethylhydantoin).

Characterization. Polyurethane (D$_6$-DMSO) $^1$H NMR spectra were recorded using a Varian Spectrometer (Inova 400 MHz) operating at 400 MHz. FT-IR spectra were obtained using a Nicolet 400 FT-IR spectrometer using solution cast films on KBr discs. Differential Scanning Calorimetry (DSC) was done with a TA-Q 1000 Series™ instrument (TA Instruments). Unless otherwise noted, measurements were carried out at a heating rate of 10° C./min from −75° C. under inert atmosphere. Indium metal was used for calibration. In addition to standard DSC, temperature modulated DSC (MDSC) with modulation amplitude of ±0.5° C., modulation period of 60 seconds, and heating rate of 3° C./min was also carried. DSC samples were directly deposited on the DSC pan.

Molecular Weight Determination. Polyurethane molecular weights were measured using a Viscotek TriSEC triple detector GPC system (THF) with sample concentrations of 5-15 mg/mL and a flow rate of 1 mL/min. Universal calibration by polystyrene standards was used for calculation of molecular weight ($M_n$, $M_w$) and polydispersity.

Wetting behavior. Dynamic contact angle (DCA) analysis based on the Wilhelmy plate method [Wilhelmy, 1863 #1464] was carried out with a Cahn Model 312 Analyzer (Cerritos, Calif.). The surface tension quantification limit of the instrument is 0.1 dyne/cm. The probe liquid was ~18 MΩ·cm deionized water from a Barnstead (Dubuque, Iowa) Nanopure system. The surface tension of the probe liquid was checked daily and was typically 72.6±0.5 dynes/cm. Beakers used for DCA analysis were cleaned by soaking in an isopropanol/potassium hydroxide base bath for at least 24 h, rinsed for 30 sec with hot tap water and then rinsed another 30 sec with nanopure water.

In a typical determination, a coated slide was attached to the electrobalance via a clip and the stage with the beaker of water was automatically raised and lowered to allow water to impinge upon the slide. By analyzing the resulting force versus distance curves (fdc's), advancing ($\theta_{adv}$) and receding ($\theta_{rec}$) contact angles were obtained. Unless otherwise noted, the stage speed was 100 µm/sec and dwell times between advancing and receding test segments was 10 sec.

The static contact angles and the image profiles were obtained by using a Rame-Hart goniometer with a camera attached. The contact angles were measured using Drop image 1.4.11 version.

Precursor PUs. Co-polymerization of 3FOx and BrOx was carried out by a modification of a procedure by Malik, 2000 #278; Makal, 2005 #1543. Cationic ring opening polymerization of 3FOx and BrOx with calculated feed ratio using $BF_3$ etherate catalyst and BD as co-catalyst gave the desired telechelic, P(3FOx:BrOx-m:n), where the segmer ratio follows the designation of 3FOx and BrOx repeat units. Isophorone diisocyanate (IPDI), 1,4-butanediol (BD) and P(3FOx:BrOx-m:n) gave IPDI-BD(40)/P(3FOx:BrOx-m:n) polyurethane, as previously described. [Makal, 2005 #1543] IPDI-BD(40)/P(3FOx:BrOx-m:n) polyurethanes were used for hydantoin PU synthesis as described below. Precursor polyurethanes with varying hard block content were obtained. The optimum hard block content was 40-45 wt %. The polyurethanes with lower hard segment content (25-35%) are mechanically weak while those having higher hard block content (45-60%) are rigid.

Hydantoin PUs. The 5,5-dimethylhydantoin containing polyurethanes were obtained via substitution reaction on IPDI-BD(40)/P(3FOx:BrOx-m:n) PUs. The reaction mechanism is shown in the following scheme:

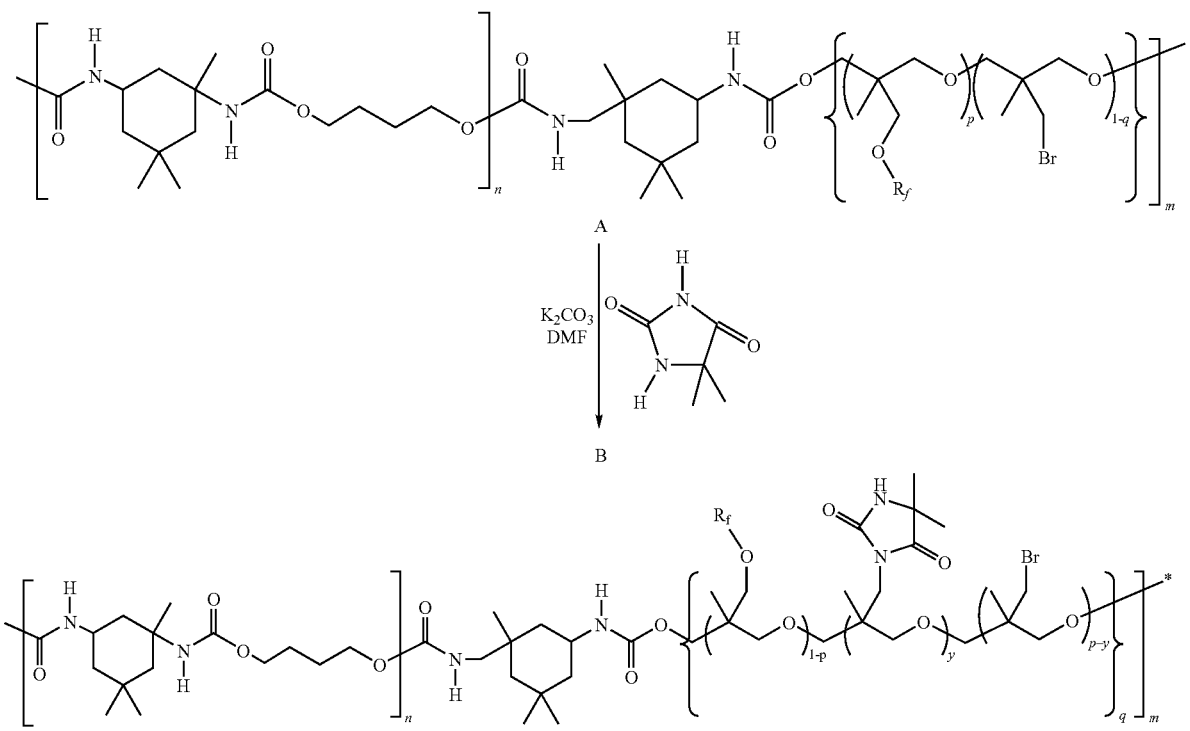

which is a 5,5-Dimethylhydantoin substitution reaction. (A) is precursor polyurethane and (B) is 5,5-Dimethylhydantoin substituted polyurethane (B). The compositions of the resulting 5,5-dimethylhydantoin substituted polyurethanes are designated

TABLE 9

Soft block compositions and degree of 5,5-dimethylhydantoin substitution.

| Soft segment composition | Initial FO$x$/BrO$x$ | % Br replaced | (FO$x$)$_x$(HyO$x$)$_y$(BrO$x$)$_z$ | | |
|---|---|---|---|---|---|
| | | | x | y | z |
| 3FO$x$:BrO$x$ | 2/1 | 60 | 2.0 | 0.6 | 0.4 |
| | 1/1 | 65 | 1.0 | 0.65 | 0.35 |
| | 1/2 | 45 | 1.0 | 0.9 | 1.1 |
| 5FO$x$:BrO$x$ | 2/1 | 68 | 2.0 | 0.32 | 0.68 |
| | 1/1 | 60 | 1.0 | 0.6 | 0.4 |
| | 1/2 | 55 | 1.0 | 1.1 | 0.9 |

IPDI-BD(40)/P(3FOx:BrOx:HyOx-p:q:t), where HyOx is the 5,5-dimethylhydantoin containing segmer. The final soft block compositions and degree of 5,5-dimethylhydantoin substitution is given in Table 9. Referring to Table 9, the degree of hydantoin substitution was obtained by comparing the ratio of the peak for the methyl groups on the semifluorinated segmer (0.86 ppm, DMSO-$d_6$) to the dimethyl peaks of 5,5-dimethylhydantoin (1.23 ppm, DMSO-$d_6$). The complete NMR characterization of a representative precursor and 5,5-dimethylhydantoin containing PU is given in FIG. 23. The optimum reaction time was about 72 h (60-65% substitution). Makal, U.; Wood, L.; Ohman, D.; Wynne, K. J., Polyurethane Biocidal Polymeric Surface Modifiers, *Biomaterials*, 2005, doi:10.1016/j.biomaterials.2005.08.038.

Longer reaction times resulted in only modest increases in substitution (e.g. 96 h, 66-70%). Furthermore, longer reaction times resulted in degradation as the reaction mixture turned a dark brown color. The slow rate and incomplete substitution of $CH_2$—Br by hydantoin is likely due to steric hindrance at the neopentyl carbon site.

Figure 23A:
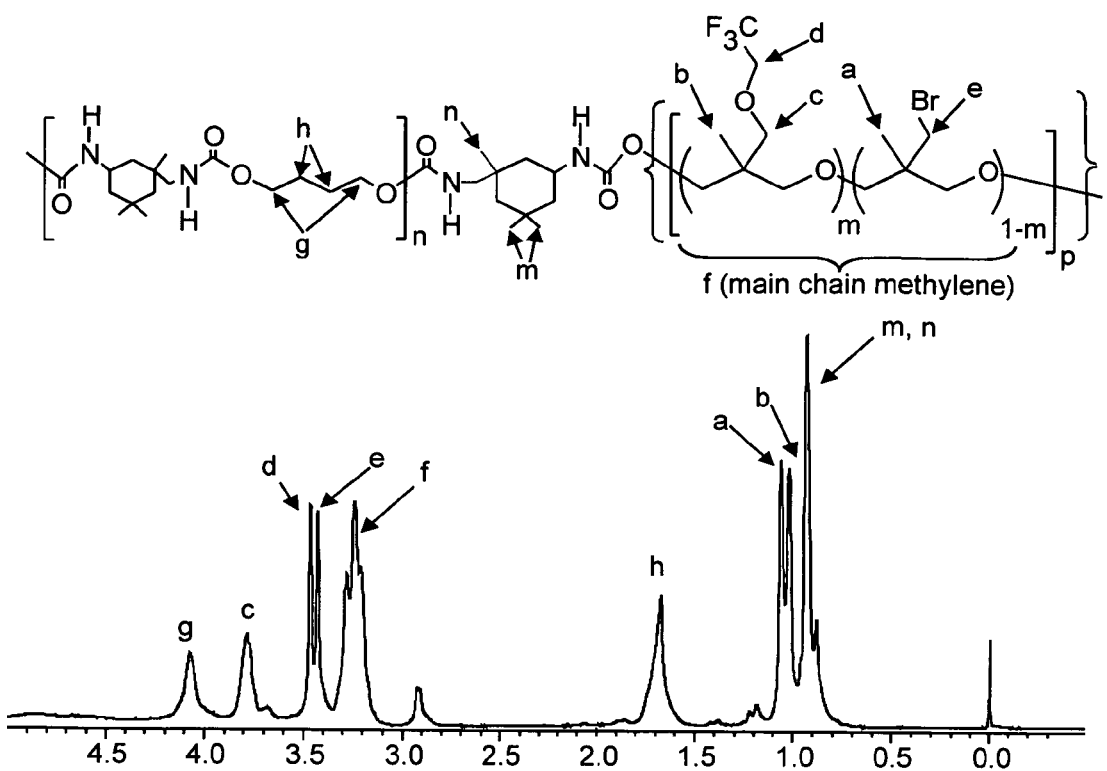
FIG. 23A, B are $^1$H NMR spectra.
Figure 23B:
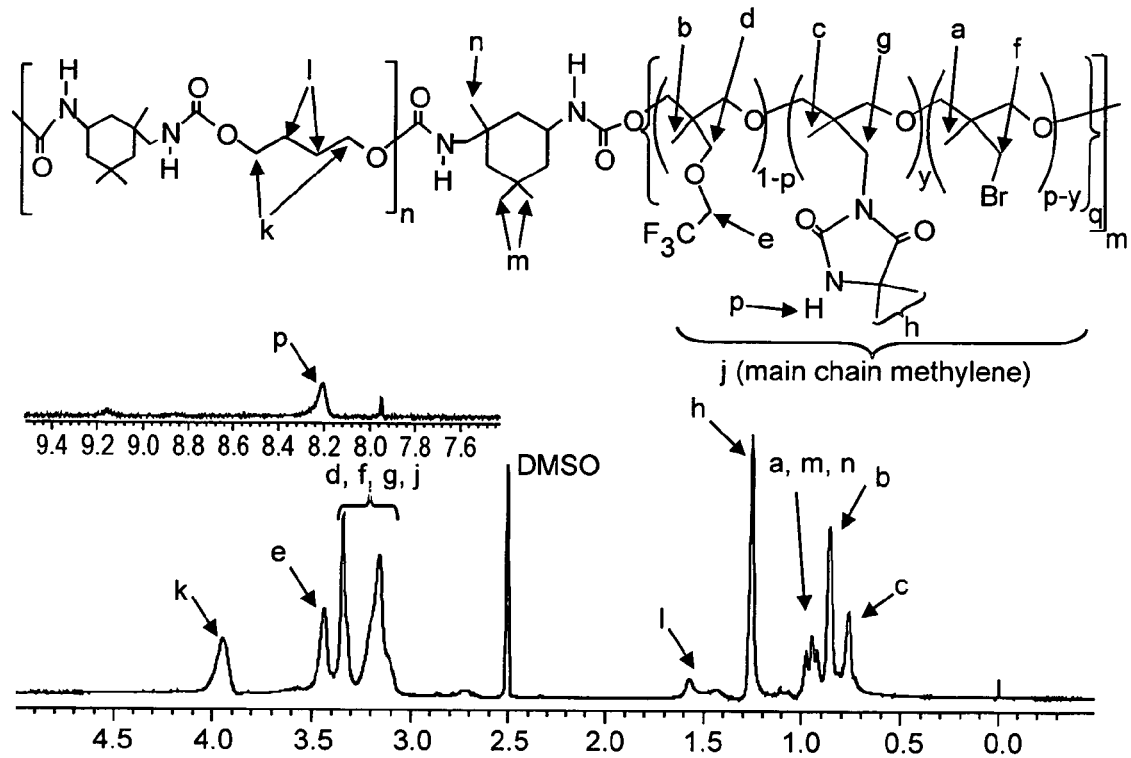

$^1$H NMR. The $^1$H NMR spectra of a representative precursor, IPDI-BD(40)/P(3FOx:BrOx-1:1), and 5,5-dimethylhydantoin-substituted polyurethane, IPDI-BD(40)/P(3FOx:HyOx:BrOx-1.0:0.65:0.35), PU-2 are shown in FIG. 23. The additional methyl and amide proton peaks on PU-2 at 1.23 ppm and 8.21 ppm are due to the 5,5-dimethylhydantoin moieties, respectively. Methylene peaks due to the HyOx segmer are not well resolved due to overlap with methylene protons on other segmers. The degree of hydantoin substitution was obtained by comparing the ratio of the peak for the methyl groups on the semifluorinated segmer (0.86 ppm, DMSO-$d_6$) to the dimethyl peaks of 5,5-dimethylhydantoin (1.23 ppm, DMSO-$d_6$).

Molecular weights. Soft block compositional designations and molecular

TABLE 10

Molecular weights of precursor and 5,5-dimethylhydantoin-substituted polyurethanes by GPC.

| | Before 5,5-Dimethylhydantoin substitution | | After 5,5-Dimethylhydantoin substitution | |
|---|---|---|---|---|
| Precursor PU soft segment composition | $M_n$ (×10$^3$ g/mol) | $M_w$ (×10$^3$ g/mol) | $M_n$ (×10$^3$ g/mol) | $M_w$ (×10$^3$ g/mol) |
| P(3FOx:BrOx-2:1) | 19 | 46 | 15 | 36 |
| P(3FOx:BrOx-1:1) | 18 | 37 | 18 | 39 |
| P(3FOx:BrOx-1:2) | 17 | 34 | 15 | 27 |
| P(5FOx:BrOx-2:1) | 19 | 40 | 19 | 33 |

TABLE 10-continued

Molecular weights of precursor and 5,5-dimethylhydantoin-substituted polyurethanes by GPC.

| Precursor PU soft segment composition | Before 5,5-Dimethylhydantoin substitution | | After 5,5-Dimethylhydantoin substitution | |
|---|---|---|---|---|
| | $M_n$ (×10³ g/mol) | $M_w$ (×10³ g/mol) | $M_n$ (×10³ g/mol) | $M_w$ (×10³ g/mol) |
| P(5FOx:BrOx-1:1) | 16 | 29 | 13 | 25 |
| P(5FOx:BrOx-1:2) | 17 | 34 | 25 | 38 |

TABLE 11

Soft block Tg's before and after 5,5-dimethylhydantoin substitution.

| Polyurethane | Soft segment $T_g$ Before (° C.) | Soft segment $T_g$ After (° C.) |
|---|---|---|
| PU-1 | −29 | 11 |
| PU-2 | −29 | 17 |
| PU-3 | −24 | 2 |
| PU-4 | −29 | 16 |
| PU-5 | −25 | 13 |
| PU-6 | −27 | 10 | weights of both precursor and 5,5-dimethylhydantoin-substituted polyurethanes are given in Table 10. The GPC analysis gave $M_w$'s in the range of 30-47K for the precursor, and 25-40K for hydantoin-substituted polyurethanes. The molecular weights of precursor and hydantoin substituted PUs are similar within the experimental error. The soft block molecular weight is increased by substitution of Br (80 g/mol) by 5,5-dimethylhydantoin (128 g/mol). But this increase was not measured with GPC. Probably, slight chain cleavage in the precursor PU structure during the substitution reaction compensated this increase in the molecular weight.

DSC. Polyurethanes have two $T_g$'s due to the soft and hard blocks in their structure. The thermal analysis of the polyurethanes was performed using both temperature modulated (MDSC) and conventional DSC. The lower soft block $T_g$'s are easily measured by conventional DCS. Whereas, MDSC was employed for measuring the hard segment $T_g$. The DCS scans were performed form −70° C. to 150-170° C. previously, we have reported the lower and upper Tg's for precursor PUs. [Makal, 2005 #1543] the phase separation in these PU systems were calculated using the DCS data and the Fox equation. [Makal, 2005 #1543] For the substituted PUs, we were not able to detect hard segment Tg using both conventional or MDSC probably due to extensive phase mixing. Therefore, no phase separation calculations were performed for the hydantoin-substituted PUs.

The soft block $T_g$'s before and after 5,5-dimethylhydantoin substitution are shown in Table 11. Soft block $T_g$ of precursor PUs increased substantially after 5,5-dimethylhydantoin substitution. The increase is in the range of 29-46°. For example, soft block Tg of IPDI-BD(40)/P(3FOx:BrOx-1:1) (−29°) increased 46° after 5,5dimethylhydantoin substitution (17°). The polar nature of heterocyclic 5,5-dimethylhydantoin, is no doubt responsible for increase in Tg's.

Wetting behavior. The wetting behavior of the polyurethanes was determined by the Wilhelmy plate method using a Dynamic Contact Angle Analyzer (DCA). [Wilhelmy, 1863 #1464; Hogt, 1985 #258; Adamson, 1997 #398] The Wilhelmy plate method has been employed for the measurement of intrinsic contact angles for model PDMS networks. [Uilk, 2003 #639] Several advantages for the Wilhelmy plate method have been noted. [Lander, 1993 #257] A large polymer surface is interrogated in the DCA experiment compared to the sessile drop method. [Uilk, 2003 #639] Another feature is facile testing of water surface tension after sample analysis. [Uilk, 2003 #639] This important control is performed by using a glass cover slip (flamed to remove organic contaminants) to analyze water surface tension before and after evaluating a polymer coating. A decrease in post-use water surface tension indicates water surface contamination by surface-active materials such as oils and/or amphiphiles leached from the coating. The ready qualitative detection of water insoluble leached species is of particular importance to biomedical, electronic, and space applications.

Cover glass slides were dip-coated from THF solutions of polyurethanes (15-20% solids). The coatings were kept in upright position under the hood for 2 h. Then the coatings were placed in a vacuum oven at 50° C. for 24 h. Before any DCA measurements all the coatings were annealed for another 24 h under vacuum at 85° C. We favor dip

TABLE 12

Soft block composition and advancing and receding contact angles for 5,5-dimethylhydantoin substituted polyurethanes.

| Soft Block Composition | Polyurethane Designation | Dynamic Contact Angle (°)* | | | | | | | | | |
|---|---|---|---|---|---|---|---|---|---|---|
| | | Cycle1 | | Cycle2 | | Cycle3 | | Cycle4 | | Cycle5 | |
| | | $\theta_{adv}$ | $\theta_{rec}$ | $\theta_{adv}$ | $\theta_{rec}$ | $\theta_{adv}$ | $\theta_{rec}$ | $\theta_{adv}$ | $\theta_{rec}$ | $\theta_{adv}$ | $\theta_{rec}$ |
| P(3FOx:HyOx:BrOx-2.0:0.60:0.40) | PU-1 | 72 | 32 | 101 | 34 | 100 | 34 | | | | |
| P(3FOx:HyOx:BrOx-1.0:0.65:0.35) | PU-2 | 70 | 35 | 104 | 37 | 101 | 38 | 101 | 38 | 101 | 38 |
| P(3FOx:HyOx:BrOx-1.0:0.9:1.1) | PU-3 | 93 | 28 | 104 | 34 | 104 | 36 | | | | |
| P(5FOx:HyOx:BrOx-1.0:1.1:0.9) | PU-4 | 93 | 42 | 105 | 42 | 104 | 42 | 104 | 42 | 104 | 42 | coating over spin casting because Wilhelmy plate analysis requires entire coverage of both sides of the glass slide. The resulting coatings were transparent. Some coatings had slightly yellow color. The coloring was observed after 5,5-dimethylhydantoin substitution.

Advancing ($\theta_{adv}$) and receding ($\theta_{rec}$) contact angles are given in Table 12. After the synthesis, each precursor polyurethane was precipitated into methanol/water mixture at least once for purification. After running 5,5-dimethylhydantoin substituted PUs with DCA, the water surface tension was also checked using flamed plain glass slide. No water contamination was observed.

The goal in this Example regarding polymeric surface modifiers (SM) was to alter the surface characteristics of a macroscopically thick coating. SMs are employed to bring the desired functionality to the surface. Because a very small amount of PSM is used for surface modification, the mechanical bulk properties of the coating remain intact. Modification of surfaces using a PSM approach has been employed before, in certain examples. For example, the surfaces made hydrophobic using PDMS PSMs[Ho, 1994 #658; Ratner, 1986 #702; Tezuka, 1986 #518], hydrophobic and oleophobic with fluorinated PSMs. [Malik, 1997 #280; Thomas, 1997 #123; Thomas, 2000 #281; Thomas, 1998 #209] PSM approach has also been employed for surface concentration of UV absorbers[Vogl, 1994 #678], and fullerenes. [Chen, 1999 #454]

The inventive SMs of this Example have soft segments containing pendant semifluorinated and functional $CH_2$—Br group. Replacing the —Br with a different functionality results in new SMs. For comparison purposes, a conventional base was referred to for which the wetting behavior was previously reported. [Makal, 2005 #1545] These comparison precursor PUs were used as PSM (0.5 wt %) for surface modification of a conventional base polyurethane. Surface enrichment of these PSM PUs was investigated by XPS, TM-AFM, and DCA. We observed that 0.5 wt % was sufficient for the altering the wetting characteristics of base PU. The PSM covered the entire top surface of the composite coating when used 1 wt %.

Upon conversion of amide functionality to chloramide simply by exposing the surface to dilute hypochlorite solution, the surface becomes highly effective contact biocide. [Eknoian, 1998 #161; Worley, 1996 #170] We have verified the biocidal activity of PU coatings containing 2 wt % biocidal PSM against both Gram-positive (*S. aureus*) and Gram-negative (*P. aeruginosa*, and *E. coli*) type bacteria. [Makal, 2005 #1437]

In preparing biocidal PU coatings, 5,5-dimethylhydantoin substitution was the intermediate step. During the surface characterization of these intermediate products, 5,5-dimethylhydantoin substituted PUs, it was observed that dry coating becomes more hydrophobic as it gets wet (so-called "contraphilic wetting," thus named because the behavior is opposite to expected amphiphilic surface response).

Contraphilic wetting behavior of IPDI-BD(40)/P(5FOx: HyOx:BrOx-2.0:0.7:0.3) (PU-6) has been observed. [Makal, 2005 #1542] DCA measurements of this PU gave $\theta_{adv}$ of 83° for the first immersion/emersion cycle and $\theta_{adv}$ increased to 110° for the rest of the cycles. Contraphilic behavior has been observed for polyurethanes with different compositions. Table 12 shows the soft block composition of PUs and dynamic contact angle data. The precursor PUs contain either trifluoroethoxy (3FOx) or pentafluoropropoxy (5FOx) pendant semifluorinated and —$CH_2$—Br (BrOx) side chains in their soft segments with different ratios.

The $\theta_{adv}$ and $\theta_{rec}$ for each cycles (3 or 5) for the PUs is shown in Table 12. The percent hydantoin substitution is given in Table 9.

Previously, we have reported dry PU-6 surface has $\theta_{adv}$ of 83° and once hydrated the contact angle increased to 110°. After annealing the coating at 85° for overnight under vacuum, we observed $\theta_{adv}$ of 68° for the dry coating and once the surface hydrated the contact angle increases to 106° (Table 12). The effect is perfectly reversible for 4 cycles. Thus, these processing conditions were used for each coating in this Example.

PU-4, -5, and -6 contain 5FOx as the semifluorinated pendant group. Within this series the PU coating having the greatest semifluorinated to 5,5-dimethylhydantoin ratio has the smallest initial contact angle and the contraphilic effect is maximized for this composition. The contraphilic effect is defined as the difference between the advancing contact angles for the second and the first immersion/emersion cycle. For example, PU-6 has the largest semifluorinated/5,5-dimethylhydantoin ratio (~2.9). Dry PU-6 has $\theta_{adv}$ of 68° and the contraphilic effect is 38°. PU-4 has the smallest semifluorinated/5,5-dimethylhydantoin ratio (~0.9). Dry PU-4 has $\theta_{adv}$ of 93° and the contraphilic effect is only 12°. Whereas, PU-5 has an intermediate semifluorinated/5,5-dimethylhydantoin (~1.7) ratio and the dry PU-5 surface has an intermediate $\theta_{adv}$ of 83° with contraphilic effect of 25°. Although one might expect the PU coating with the highest semifluorinated/5,5-dimethylhydantoin ratio to have the most hydrophobic surface, the opposite was actually observed. This kind of trend is not observed for the 3FOx containing series, PU-1, -2, and -3. The dry PU-1 (72°) and PU-2 (70°) coatings gave similar initial $\theta_{adv}$ values. The contraphilic effect for PU-1 (29°) is not significantly different from PU-2 (34°). The same trend is observed if PU-1, and PU-2 is compared to PU-3. The semifluorinated/5,5-dimethylhydantoin ratio for PU-1 (~3.3) and PU-2 (~1.5) is greater than that of PU-3 (1.1). Dry PU-3 coating has $\theta_{adv}$ of 93° and 12° of contraphilic effect. Again the coatings with higher semifluorinated/5,5-dimethylhydantoin ratio have more hydrophilic surface when dry.

FIG. 24 shows the actual DCA fdc's and goniometer drop profiles for a representative PU coating for each series, PU-6 (FIG. 24B) for 5FOx and PU-2 (FIG. 24A) for 3FOx series. The force readings for the first fdc are positive (apparent mass gain) for both PU-6 and PU-2 indicating hydrophilic character. After the first immersion emersion cycle the coating was completely wetted. This time negative force readings (apparent mass loss) were obtained indicating hydrophobic surface. In addition to Wilhelmy plate analysis, the static contact angles and actual drop profiles for these representative PUs are shown in FIG. 24. The static contact angles measured from goniometer for each profile is reported in the figure. The switching of the surface from hydrophobic to hydrophilic with water can easily be seen from the actual drop images.

Surface switching between hydrophilic/hydrophobic states is a well-known phenomenon in the literature. In a series of papers, Tsukruk reported "Y" shaped nano brushes. These "Y" shaped molecules have two incompatible arms. One arm consists of hydrophilic poly(acrylic acid) and the other arm is made of hydrophobic poly(styrene). Depending on the polarity of the contacting medium, one of these arms dominates the air-polymer interface changing the wetting characteristics of the surface. For example, if the brushes are treated with toluene non-polar poly(styrene) arm covers the surface giving water contact angle of 73°. After water treatment of the same surface polar poly(acrylic acid) arm dominates the air polymer interface resulting 53° of water contact angle. [Julthongpiput, 2003 #1433; Julthongpiput, 2003 #1435; Luzinov, 2004 #1471] In both cases the surface tries to minimize overall free energy. The lower critical solution temperature (LCST) behavior of poly(isopropyl acrylamide) is coupled with surface roughness. The resulting surface thermally switches between ultrahyrdophilic (0°) and ultrahydrophobic (150°) below and above the LSCT, respectively. [Sun, 2004 #717]

The inventive coatings of this Example switch in the exact opposite way than any surface that becomes hydrophilic when exposed to water and hydrophobic when exposed to organic solvent. In other words, the inventive coatings of this Example behave in a way opposite to anticipated amphiphilic response. Thus, the inventive coatings of this Example are "contraphilic".

Most of the polymers having modestly hydrophilic character, such as PUs, become more hydrophilic with immersion in water, [Tingey, 1991 #600; Andrade, 1985 #403; Pike, 1996 #26] or polymers having polar functionality become more hydrophilic as function of water immersion time. [Tretinnikov, 1994 #598; Holmes-Farley, 1985 #271] Surface reorganization of polymers in water or polar environment is driven thermodynamically. The enthalphic driving force due to the hydrogen bonding of surface polar functionalities with water easily overcomes the entropy trying to form more ordered molecular structure. Upon exposure to water polymer surfaces rearrange in order to open paths for the polar hydrophilic moieties to migrate water-polymer interface. Concentration of polar moieties at the surface gradually decreases the advancing contact angle. [Russell, 2002 #1467; Senshu, 1999 #1457; Lemieux, 2003 #1434] The inventive PU surfaces of this Example display the opposite anticipated wetting behavior: for the Example surfaces, the dry PU surface becomes more hydrophobic with water. Upon dehydration of the wetted surface, the initial hydrophilic character is restored.

The contraphilic effect is believed to be driven enthalpically (like amphiphilic response). The soft segment in the polyurethanes contains semifluorinated and 5,5-dimethylhdantoin pendant groups. In other words, the soft block has both fluorinated and amide groups. The role of a surface amide group is well known. The hydrogen bonding of amide groups with water and with each other below and above the LCST, respectively is responsible for the hydrophilic/hydrophobic switching for poly(N-isopropylacrylamide) surface [Sun, 2004 #1507] having amide and semifluorinated side chain on a relatively flexible backbone may result rapid hydration of the surface.

FIG. 25 demonstrates the proposed mechanism which the present inventors have previously reported for contraphilic behavior. [Makal, 2005 #1542] For the dry surface (FIG. 25A), the enthalpically driven hydrogen bonding of amide groups of 5,5-dimethylhydantoin moieties to acidic methylene hydrogens of semifluorinated groups prevents the surface concentration of semifluorinated groups. In addition, the polar N—H is more available for water resulting hydrophilic surface. Upon exposure to water (FIG. 25B), amide groups prefer to hydrogen bond with water rather than the methylene hydrogens releasing the semifluorinated moieties as a result surface becomes hydrophobic. If the surface is dehydrated, the initial hydrophilic wetting character is restored and the surface switches hydrophilic to hydrophobic with dehydrating and hydrating the surface, respectively. [Makal, 2005 #1542]

Certain examples of contraphilic-like wetting has been reported previously. Ferguson reported oxidized 1,2-polybutadiene surfaces become more hydrophobic against hot water. [Carey, 2000 #272; Khongtong, 2002 #1431] This is an entropically driven process. The entropic loss due to the stretched chains translates into elastic restoring force as the temperature increases. Thus, the polar groups are pulled away from water-polymer interface gradually increasing the hydrophobicity of the surface. But the change in the wetting behavior of oxidized 1,2-polybutadine surface is damped after successive cycles. In contrast, the contraphilic wetting is observed with cycling between dry and wet states.

Example 8C

Hydantoin-Containing Polyurethane PSMs: Contraphilic Materials Prepared Via Mixed Soft Blocks: Poly(Ethylene Oxide)-(FOx:BrOx) Co-Soft Block Containing Polyurethanes Mixed soft block polyurethanes were prepared according to the general example shown in FIG. 5E. Equation 6 (FIG. 5E) is for a general example of "mixed soft blocks" which is a convenient industrial approach as surface properties can be tuned without making a separate polyurethane SM. In the example below, a polyethylene oxide soft block-hydantoin soft block composition is prepared. One goal of this work was to increase the wettability. In this example, in order to enhance wetting by water, the surface tension (hydrophilicity) of the coating was increased by incorporating a poly(ethylene oxide) (PEO) soft block as co-soft segment in polyurethane.

Synthesis of polyurethane having poly(ethylene oxide)-(3FOx:BrOx-1:2) soft block (PU-PEO/3A) (PEO is the acronym for polyethylene oxide soft block; "3A" connects the composition of this soft block to the "1:2 3FOx:BrOx soft block".)

A 250 mL three-neck round-bottomed flask equipped with a mechanical stirrer, nitrogen inlet, and condenser was charged with 7.49 g (33.69 mmol) IPDI, 6.06 g (4.04 mmol) and 8.70 g (3.48 mmol) P(3FOx:BrOx-1:2) co-telechelic so that the molar feed ratio of PEO/P(3FOx:BrOx-1:2) was close to 1.0. The reaction was started in DMF with an initial 85-90 wt % concentration of reactants. After addition of dibutyltin dilaurate catalyst (0.15-0.20 weight % of the total reaction mixture in THF), the reactants were kept at 65-70° C. for 3 h. The preparation of diisocyanate-terminated prepolymer was confirmed by FT-IR spectroscopy (urethane carbonyl, 1724 cm$^{-1}$, and N—H, 3346 cm$^{-1}$, absorbances).

In the second stage, BD was added and heating was continued (65° C.) until all isocyanate groups were consumed (ca. 5 h). The course of the chain extension reaction was monitored with FT-IR by following the disappearance of sharp isocyanate band at 2267 cm$^{-1}$. As the viscosity increased during the chain extension reaction, DMF or DMF/THF was added to dilute the reaction mixture. The final solids content of the polymer solution was 50-60%. The product was precipitated into methanol or methanol/water for purification.

Figure 26:
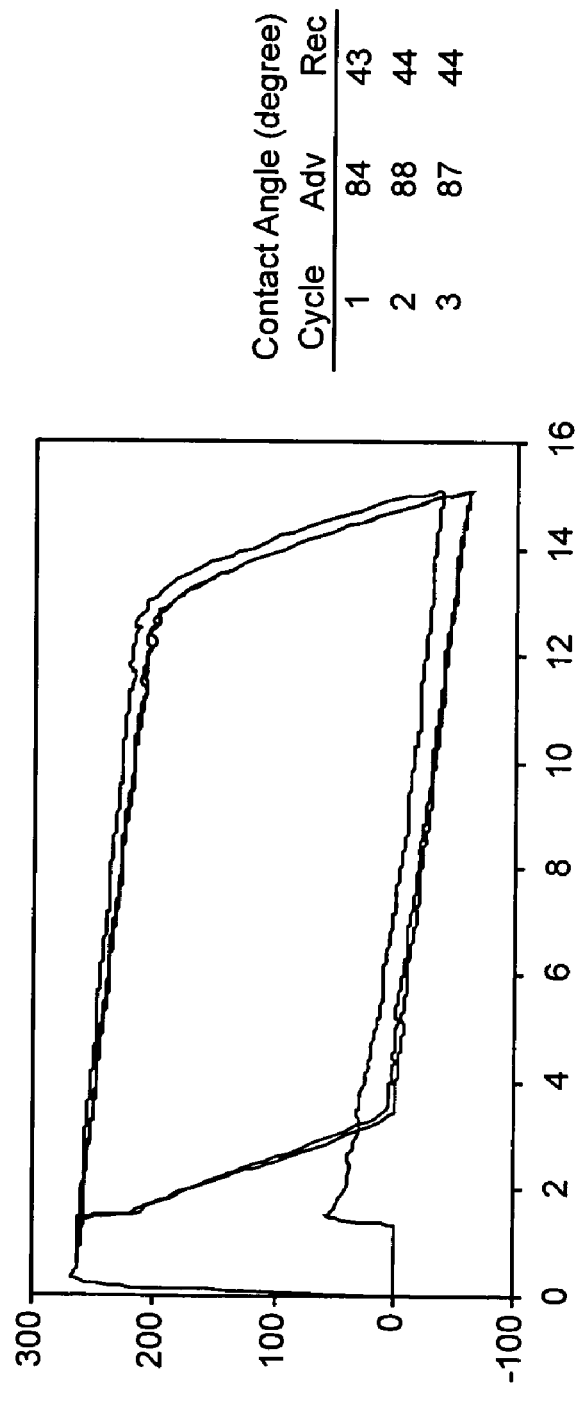
FIG. 26 shows force versus distance curves and dynamic contact angles for bulk IPDI-BD-PTMO coating doped with 10 wt % PU-2: Co-Soft Block: [PEO]1-[3FOx:BrOx-1:2]1 with 5,5-dimethylhydantoin (~55% substitution of C—Br by Hy); Hard Block: IPDI-BD (40%), solvent cast film from THF dried at 60° C., 4 Torr overnight.

Preparation of PU-2 by 5,5-dimethylhydantoin substitution onto PU-1. Replacement of Br with 5,5-Dimethylhydantoin substitution reaction was carried out in DMF in the presence of $K_2CO_3$. The reaction conditions were as in the above Example. FIG. 26 shows force versus distance curves and dynamic contact angles for bulk IPDI-BD-PTMO coating doped with 10 wt % PU-2: Co-Soft Block: [PEO]1-[3FOx:BrOx-1:2]1 with 5,5-dimethylhydantoin (~55% substitution of C—Br by Hy); Hard Block: IPDI-BD (40%), solvent cast film from THF dried @60 C, 4 Torr overnight.

Surface characterization of pure PU-1, PU-2 and polyurethane coatings doped with PU-2: Polyurethane wetting behavior was determined by the Wilhelmy plate method using a Dynamic Contact Angle (DCA) analysis. Glass cover slips were dip coated using THF solutions. The solvent was removed at 50° C. in vacuo. PU-2 was used as PSM (10 wt %) for surface modification of base PU (PTMO based PU). FIG. 26 shows the fdc's and DCA data for an IPDI-BD-PTMO polyurethane doped with 10% hydantoin containing, mixed soft block, surface modifying additive, PU-2. The coating had $\theta_{adv}$ of 84° for the first cycle and increased to 88° for the second cycle. The observed contact angles were not significantly different than that of pure base PU (88°) but the observation of contraphilic effect suggested the presence of PSM at the air-polymer interface. As further evidence for the existence of the SMA at the surface, the chlorinated surface displayed $\theta_{adv}$ of 96°. Conversion of near surface N—H to N—Cl decreased the polarity of the surface resulting increased advancing contact angle. $\theta_{adv}$ for the corresponding chlorinated coating (without PEO) was 102°. Hence, the incorporation of PEO as co-soft block along with P(3FOx:HyOx:BrOx) co-telechelic increased the hydrophilicity of the surface.

Example 9

Inventive Polyurethane/Polymeric Surface Modifier (PSM) Technology

Figure 27:
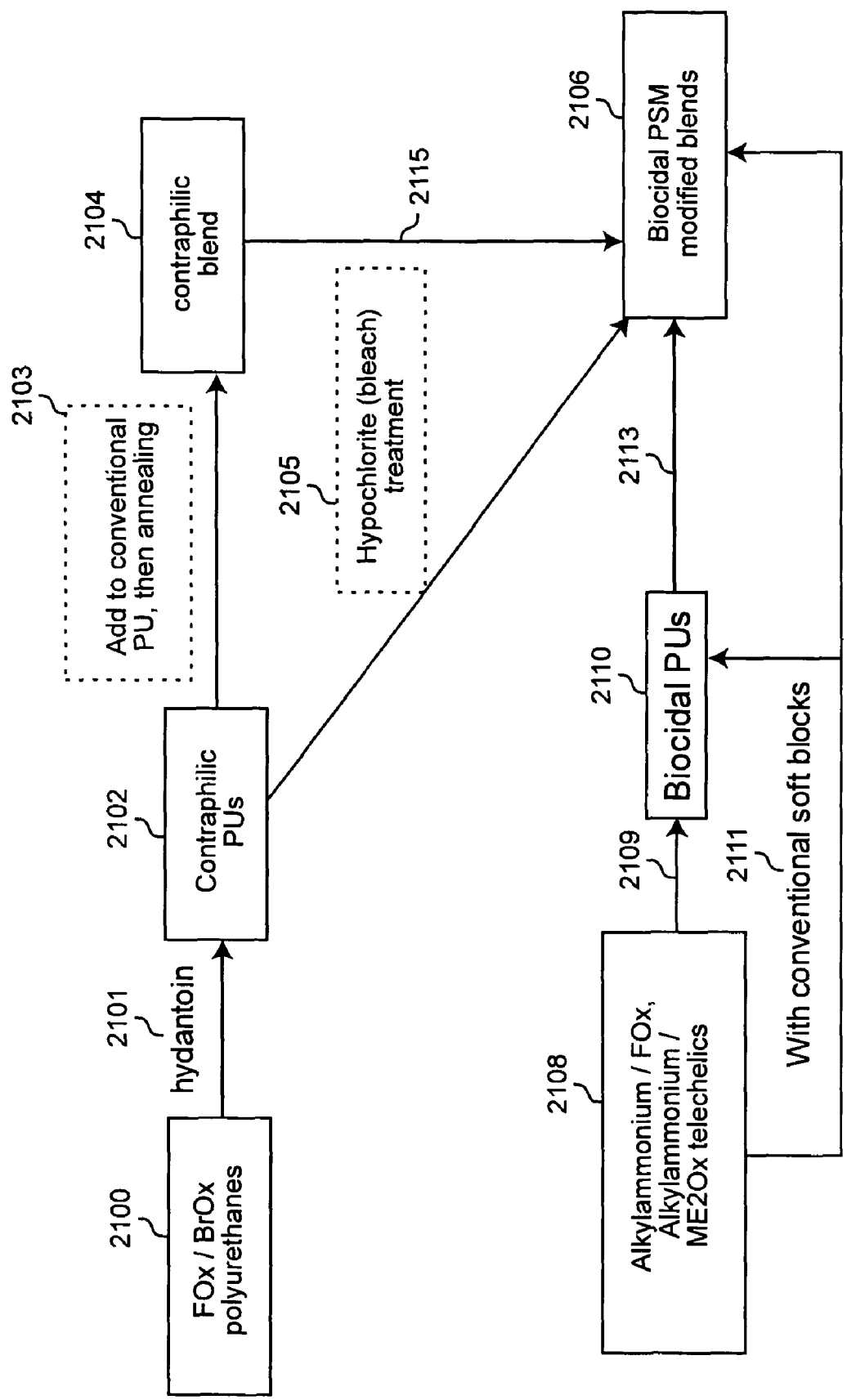
FIG. 27 is a block diagram that is exemplary of inventive polymeric surface modifier (PSM) technology as applied to polyurethanes.

Referring to FIG. 27, an example may be appreciated of using at least one polymeric surface modifier (PSM) with at least one polyurethane according to the present invention. FOx and/or BrOx polyurethanes (2100) are processed (2101) with a hydantoin to produce contraphilic polyurethanes (2102).

A contraphilic polyurethane (2102) may be added (2103) to a conventional polyurethane, followed by annealing, to produce a contraphilic blend (2104). A preferred example of a contraphilic blend (2104) comprises about 2% PSM and about 98% polyurethane.

A contraphilic blend (2104) may be processed (2115) into a biocidal PSM modified blend (2106).

A contraphilic polyurethane (2102) may be subjected to hypochlorite (bleach) treatment (2105) to produce a biocidal PSM modified blend (2106). A preferred example of a biocidal PSM modified blend (2106) comprises about 2% PSM and about 98% polyurethane.

A biocidal PSM modified blend (2106) may be produced by other processes, also as shown in FIG. 27.

A starting product (2108) which is selected from an alkylammonium/FOx mixture, an alkylammonium/ME2Ox mixture, and telechelics may be processed (2109) into a biocidal polyurethane (2110). Alternately, a starting product (2108) may be processed (2111) with conventional soft blocks into a biocidal polyurethane (2110).

A biocidal polyurethane (2110) may be processed (2113) into a biocidal PSM modified blend (2106). As previously mentioned, a preferred example of a biocidal PSM modified blend (2106) comprises about 2% PSM and about 98% polyurethane.

The present inventors have made the surprising discovery that a fluorinated segment is not required for surface activity, such as, e.g., biocidal C-12 alkylammonium SMs (the C-12 alkylammonium side chain and to a lesser extent a C-6 alkylammonium side chain act as their own "chaperones"), and the biocidal "Hy4Ox/MOx" polyurethane SMs. Thus, it should be appreciated that in the processing (2101), (2103), (2105), (2109), (2111), (2113), (2115) shown on FIG. 27, using a fluorinated segment is not required to produce a product which exhibits surface activity. In the starting reagents (2108), the biocidal polyurethanes (2110) and the biocidal PSM modified blends (2106), a fluorinated segment is not required for surface activity, but desired surface function may be enhanced by the presence of a fluorinated segment.

While FIG. 27 highlights a biocidal example, it should be appreciated that, alternately (or additionally) to a biocidal function the present invention also may be used for many other desirable functions such as, e.g., control of wetting behavior, incorporation of indicators or sensors, incorporation of dyes, incorporation of adhesion promoting groups, etc.

Example 10

Preparation Via Adding a Small Amount of Contraphilic PSM to a Conventional Polyurethane A solution of 98 wt % conventional IPDI-BD/PTMO PU, Hard Block (40 wt %) and 2.0 wt % IPDI-BD/P(3FOx:HyOx:BrOx) (1.0:0.65:0.35) PSM was prepared in THF. Coverslips were coated in the way described above. After drying overnight at 50° C. in vacuum, no contraphilic behavior was noted. However, after annealing near 90° C. overnight the wetting behavior shown in FIG. 28 was observed. The difference between the first advancing contact angle for the dry coating and the second advancing contact angle for the wet coating was 32°. This result shows that through processing, the contraphilic effect of pure BD/P(3FOx:HyOx:BrOx) (1.0:0.65:0.35) was displayed with fidelity at only 2 wt % in the test polyurethane coating. This is an important result in amplifying the contraphilic effect at such a small weight percent.

Example 11

Alkylammonium Containing PSMs made from Telechelic P(N611E10x), 11, 13, 15 and 16

Synthesis of a PU PSM containing a soft block with alkylammonium side chains via the route is shown in FIGS. 5B and 5C.

(i) P(N611E1Ox) (2.07 g) in 1.17 g DMF was heated under nitrogen purge in three-necked round bottom flask. At 70° C. 4,4'-methylenebis(cyclohexylisocyanate) (HMDI) was added via syringe. Three drops of 10% wt dibutyltin dilaurate in DMF was added as the catalyst. Prepolymer completion was observed by stabilization of C=O peak at 1720 cm$^{-1}$ in FTIR spectrum. After prepolymerization (3 hrs) 1,4-butanediol (0.17 g, 1.89 mmol) in 2.0 g DMF was added dropwise. The mixture reacted until complete disappearance of NCO peak at 2267 cm$^{-1}$ (ca. 4 hours). The polymer (H$_{12}$MDI (30%)-BD-P(N611E1Ox) was cooled down to room temperature and precipitated in 100 mL water. Solvent was evaporated under vacuum at 60° C. for 48 hours. The structure of H$_{12}$MDI (30%)-BD-P(N611E1Ox) is shown in FIG. 29.

Figure 30:
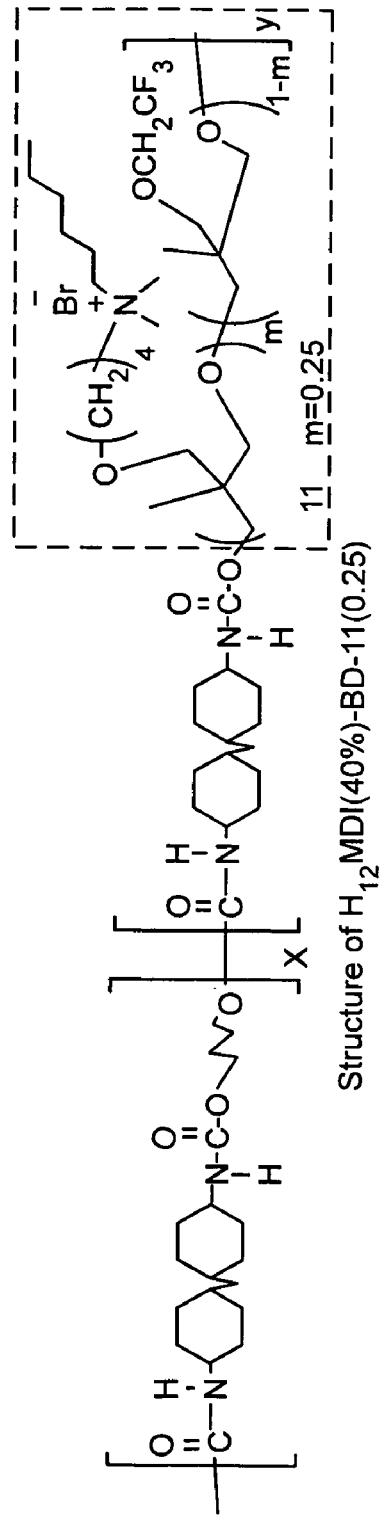
FIG. 30 shows the structure of H$_{12}$MDI(40%)-BD-11 (0.25).

(ii) The hexyl ammonium functionalized telechelic 11 (4.6 g) and 4,4'-methylenebis(cyclohexylisocyanate) (HMDI) (1.00 g, 3.4 mmol) were dissolved in a mixture solution of 10 mL anhydrous tetrahydrofuran and 10 mL anhydrous DMF in a 50 mL round-bottom flask with ten drops of 10% dibutyltin dilaurate as the catalyst. The system was heated to 60° C. for 4 hours and cooled to room temperature. 1,4-butanediol (0.2 g, 2.23 mmol) was added and the mixture was heated to 60° C. with stirring for another 4 hours. The product, H$_{12}$MDI (40%)-BD-11(0.25), was precipitated by adding diethyl ether and dried under vacuum for 3 days. The structure of H$_{12}$MDI (40%)-BD-11(0.25) is shown in FIG. 30.

Figure 31:
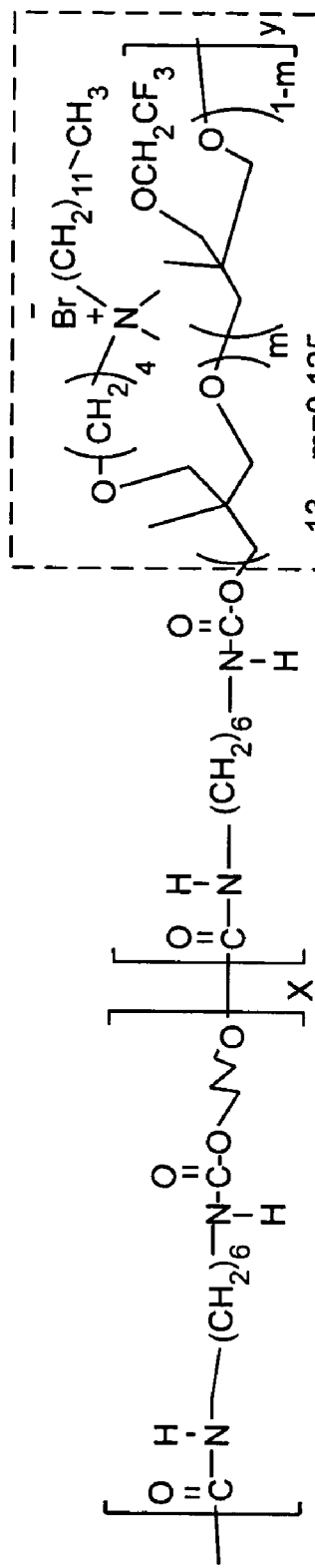
FIG. 31 shows the structure of HDI(20%)-BD-13(0.125).

(iii) The dodecyl ammonium functionalized telechelic 13 (1.06 g, 0.12 mmol) was added to a three-necked round bottom flask and heated to 70° C. under nitrogen purge. 1,6-hexamethylene diisocyanate (HDI) was added to the flask with 0.6 g DMF. Two drops of 10% wt dibutyltin dilaurate in DMF were added as the catalyst. Prepolymer completion was observed by stabilization of C=O peak at 1720 cm$^{-1}$ in FTIR spectrum. When the prepolymer was ready, 1,4-butanediol (0.09 g, 0.94 mmol) in 0.5 g DMF was added dropwise. The mixture reacted until complete disappearance of NCO peak at 2267 cm$^{-1}$ (ca. 4 hours) The polymer (HDI (20%)-BD-13 (0.125) was cooled down to room temperature and precipitated in 50 mL diethyl ether. Solvent was evaporated under vacuum at 60° C. for 48 hours. The structure of HDI (20%)-BD-13(0.125) is shown in FIG. 31.

Figure 29:
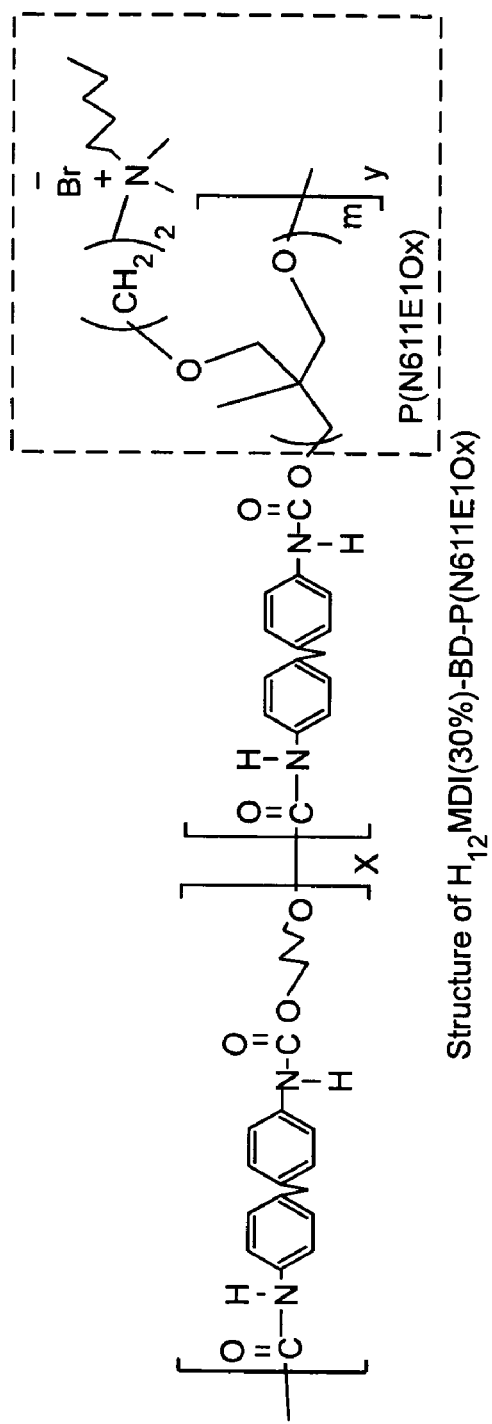
FIG. 29 shows the structure of H$_{12}$MDI (30%)-BD-P(N611E1Ox).

(iv) The alkyl ammonium functionalized telechelic 15 was used to prepare H$_{12}$MDI(40%)-BD-15(0.25) by a method similar to that was described for the H$_{12}$MDI(40%)-BD-11 (0.25), polyurethane shown in FIG. 29. The structure of H$_{12}$MDI(40%)-BD-15(0.25) is shown in FIG. 32.

Figure 33:
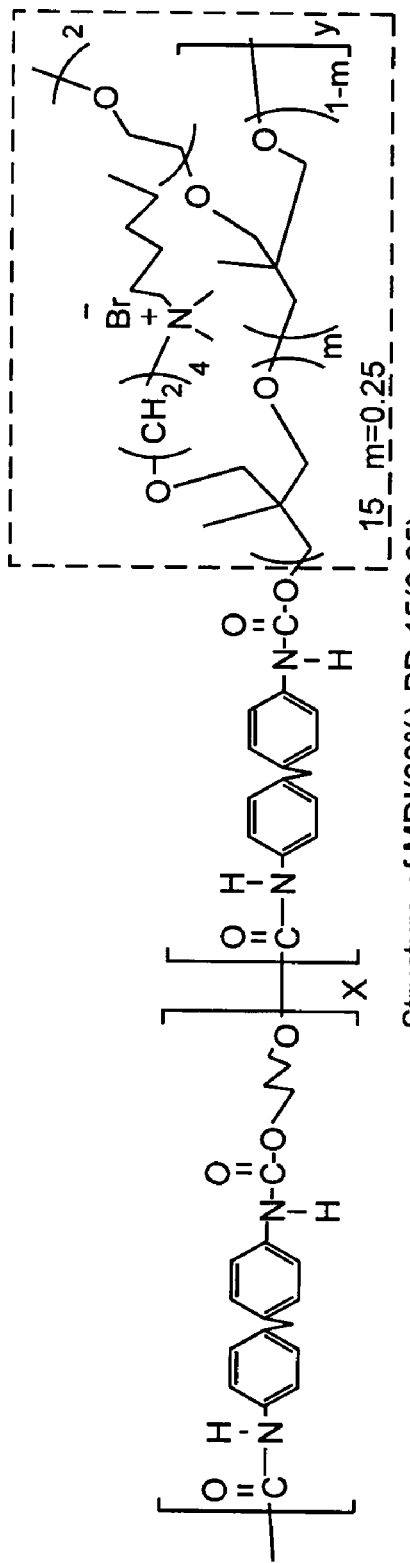
FIG. 33 shows the structure of MDI (30%)-BD-15(0.25).

(v) Telechelic 15 was used to prepare a polyurethane by using methylene bis (phenyl isocyanate) (MDI). Telechelic 15 (1.73 g), MDI(0.56 g, 2.24 mmol) and 3.0 g DMF were added to a three-necked round bottom flask and heated under nitrogen purge. Five drops of 10% wt dibutyltin dilaurate in DMF were added as the catalyst. Following prepolymer completion, 1,4-butanediol (0.20 g, 2 mmol) in 1.5 g DMF was added dropwise. The mixture reacted until complete disappearance of NCO peak at 2267 cm$^{-1}$ (ca. 4 hours). The polymer (MDI (30%)-BD-15(0.25) was cooled down to room temperature and precipitated in 100 mL water. Solvent was evaporated under vacuum at 60° C. for 48 hours. The structure of MDI (30%)-BD-15(0.25) is shown in FIG. 33.

Figure 32:
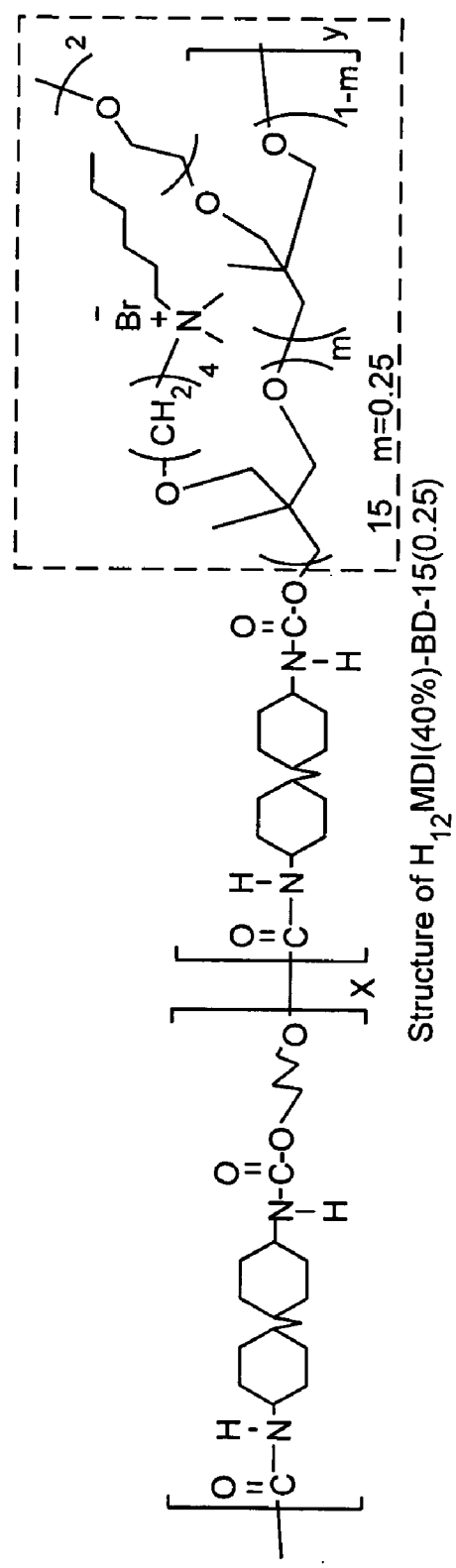
FIG. 32 shows the structure of H$_{12}$MDI(40%)-BD-15 (0.25).
Figure 34:
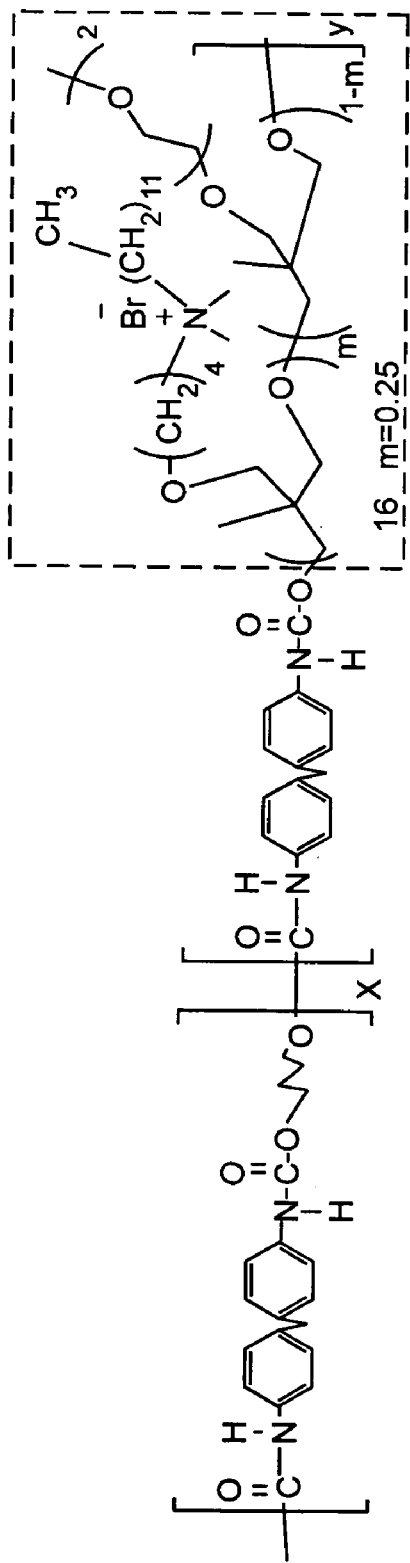
FIG. 34 shows the structure of MDI (30%)-BD-16(0.25).

(vi) Polyurethane with telechelic 16 (MDI (30%)-BD-16 (0.25)) was synthesized following a similar method to that described for telechelic 15 in FIG. 32. The structure of MDI (30%)-BD-16(0.25) is shown in FIG. 34.

While the invention has been described in terms of its preferred embodiments, those skilled in the art will recognize that the invention can be practiced with modification within the spirit and scope of the appended claims.

What we claim as our invention is:

1. A method of producing a polymeric article or coating with a surface active property, comprising the steps of: forming a surface active polymer from a telechelic having at least one segmer which enables an activity of interest; and combining said surface active polymer with bulk polymer to produce a polymeric article or coating having the surface active polymer concentrated primarily on a surface of said bulk polymer, wherein, to enable said activity of interest, said telechelic is comprised of segmers one of which has quaternary ammonium side chains and one of which has polyethylene glycol side chains.

2. The method of claim 1, wherein the polymeric article or coating with the surface active property has a combination function selected from the group consisting of biocidal activity and contraphilic activity.

3. The method of claim 2, wherein the polymeric article or coating is produced with adding a minimal amount of surface modifier of not more than 5 weight %.

4. The method of claim 1 wherein said at least one segmer is present on a soft block.

5. The method of claim 4, wherein the soft block contains no fluorinated segment.

6. The method of claim 1, wherein said telechelic is

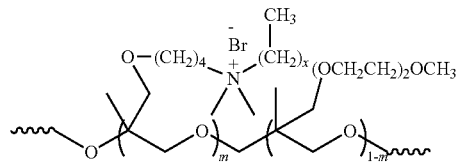

and wherein x=1-20.

7. The method of claim 1, wherein said telechelic is

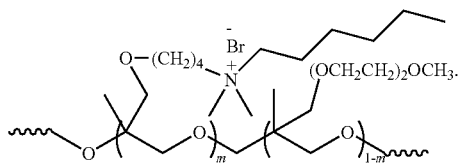

8. The method of claim 1, wherein said telechelic is

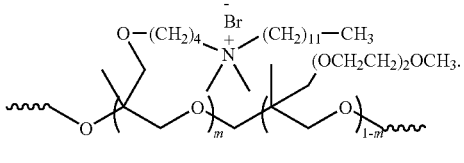

* * * * *